(12) United States Patent
Chen et al.

(10) Patent No.: US 11,312,766 B2
(45) Date of Patent: Apr. 26, 2022

(54) ANTIBODIES AGAINST GROWTH DIFFERENTIATION FACTOR 15 AND USES THEREOF

(71) Applicant: NOVARTIS AG, Basel (CH)

(72) Inventors: Hong Chen, Newton, MA (US); Rajiv Chopra, Andover, MA (US); Seung Wan Hahm, Newton, MA (US); Norio Hamamatsu, Belmont, MA (US); Ryan Scott Streeper, Needham, MA (US); Mei Xu, Arlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/096,579

(22) PCT Filed: Apr. 26, 2017

(86) PCT No.: PCT/US2017/029636
§ 371 (c)(1),
(2) Date: Oct. 25, 2018

(87) PCT Pub. No.: WO2017/189724
PCT Pub. Date: Nov. 2, 2017

(65) Prior Publication Data
US 2019/0135908 A1 May 9, 2019

Related U.S. Application Data

(60) Provisional application No. 62/328,564, filed on Apr. 27, 2016.

(51) Int. Cl.
| | | |
|---|---|---|
| A61K 39/00 | (2006.01) |
| A61K 39/395 | (2006.01) |
| C07K 16/22 | (2006.01) |
| C12N 15/11 | (2006.01) |
| C12N 15/13 | (2006.01) |
| C12N 15/63 | (2006.01) |
| C12N 1/21 | (2006.01) |
| C12N 5/10 | (2006.01) |

(52) U.S. Cl.
CPC ........ *C07K 16/22* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/92* (2013.01)

(58) Field of Classification Search
None
See application file for complete search history.

(56) References Cited

U.S. PATENT DOCUMENTS

2014/0193427 A1* 7/2014 Lerner ............... A61P 3/02
424/158.1

FOREIGN PATENT DOCUMENTS

| JP | 2015-532271 A | 11/2015 |
|---|---|---|
| JP | 2016-508984 A | 3/2016 |
| WO | WO 2010/048670 A1 * | 5/2010 |
| WO | 2014/049087 A1 | 4/2014 |
| WO | 2014/100689 A1 | 6/2014 |
| WO | 2015/144855 A1 | 10/2015 |
| WO | 2016/049470 A1 | 3/2016 |

OTHER PUBLICATIONS

Paul, Fundamental Immunology, Raven Press, New York, 1993, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
Kempf et al. (2006, Cir. Res. 98:351-350).*
Breit et al. (2012, Nephrol. Dial. Transplant. 27:70-75).*
Ho et al. (2013, Clin. Chem. 59:1613-1620).*
Abulizi et al. (2017, Sci. Rep. 7(1):1037; pp. 1-10).*
Zimmers et al. (2005, Shock 23(6):543-548.*
Mazagova et al. (2013, Am. J. Physiol. Renal Physiol. 305:F1249-F1264).*
Johnen et al., "Tumor—induced anorexia and weight loss are mediated by the TGF-beta superfamily cytokine MIC-1", Nature Medicine, 13(11):1333-1340 (2007).

* cited by examiner

*Primary Examiner* — Elizabeth C. Kemmerer
(74) *Attorney, Agent, or Firm* — Meghan S. Adams

(57) ABSTRACT

Provided herein are monoclonal antibodies (e.g., human antibodies) binding to human Growth Differentiation Factor 15 protein (hereinafter, sometimes referred to as "GDF15"), and pharmaceutical compositions and methods of treatment comprising the same.

20 Claims, 10 Drawing Sheets
Specification includes a Sequence Listing.

| Abs | Epitope | hGDF15 | rodent GDF15 | Cyno GDF15 | N-truncated hGDF15 (211-308) | Knuckle | | | Wrist | | | Finger tip | Back-of-hand |
|---|---|---|---|---|---|---|---|---|---|---|---|---|---|
| | | | | | | L294R | I285R | S231R | Q247R | W228R | M253R | Q295R | D289R | S278R |
| ABGDF15-A, D, E, F, G | Knuckle | | | | | | | | | | | | | |
| ABGDF15-B, C | Knuckle | | | | | | | | | | | | | |
| Hu01G06 | Knuckle | | | | | | | | | | | | | |

Legend: Loss-of-binding / No effect by mutation / Inhibited

Heavy Chain CDRs

| Candidate | Germline VH | HCDR1 | | | | | | | | | | | HCDR2 | | | | | | | | | | | | | | | | | HCDR3 | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| ABGDF15-C | VH1-69 | G | G | T | F | R | S | - | Y | A | V | S | G | I | - | I | P | I | F | G | T | A | N | Y | A | Q | K | F | Q | G | G | P | - | - | - | - | Y | F | Q | F | G | L | F | - | - | - | D | H |
| ABGDF15-B | VH1-69 | G | G | T | F | R | S | - | Y | A | V | S | G | I | - | I | P | I | F | G | T | A | N | Y | A | Q | K | F | Q | G | G | P | - | - | - | - | Y | F | Q | F | G | L | F | - | - | - | D | H |
| ABGDF15-A | VH5-51 | G | Y | S | F | T | D | - | Y | W | I | G | I | - | - | D | P | S | G | S | Y | T | I | - | Y | S | P | S | F | Q | G | V | S | - | - | - | - | Y | F | - | - | - | - | - | - | - | D | I |
| ABGDF15-F | VH5-51 | G | Y | S | F | T | S | - | Y | W | I | G | I | - | - | D | P | S | G | S | Y | T | I | - | Y | S | P | S | F | Q | G | Y | - | - | - | G | T | Y | F | - | - | - | - | - | - | - | D | Y |
| ABGDF15-E | VH5-51 | G | Y | S | F | T | S | - | Y | W | I | G | I | - | - | D | P | G | G | S | Y | T | I | - | Y | S | P | S | F | Q | G | Y | - | - | - | G | R | Y | F | - | - | - | - | - | - | - | D | Y |
| ABGDF15-G | VH1-69 | G | G | T | F | S | S | - | H | Y | I | G | G | I | - | - | P | A | F | G | G | A | N | Y | A | Q | K | F | Q | G | F | G | S | V | Y | W | R | Y | S | S | Y | Y | H | M | D | V |
| ABGDF15-D | VH5-51 | G | Y | S | F | T | S | - | Y | W | I | G | V | I | - | D | P | D | G | S | Y | T | I | - | Y | S | P | S | F | Q | G | Y | - | - | - | G | R | Y | F | - | - | - | - | - | - | - | D | Y |

Light Chain CDRs

| Candidate | Germline VL | LCDR1 | | | | | | | | | | | | LCDR2 | | | | | | | LCDR3 | | | | | | | | | |
|---|---|---|---|---|---|---|---|---|---|---|---|---|---|---|---|---|---|---|---|---|---|---|---|---|---|---|---|---|---|---|
| ABGDF15-C | VL3-3r | S | G | D | N | I | G | S | - | H | Y | V | S | D | K | S | N | R | P | S | Q | T | W | D | S | I | G | S | V | V |
| ABGDF15-B | VL3-3j | S | G | D | N | I | G | S | - | H | Y | V | S | D | K | S | N | R | P | S | Q | T | W | D | S | I | G | S | V | V |
| ABGDF15-A | VK1-O12 | R | A | S | Q | S | I | - | S | N | L | Y | N | A | A | S | N | L | Q | S | F | Q | L | D | H | S | P | - | F | T |
| ABGDF15-F | VL1-1e | S | G | S | S | S | N | I | G | V | L | Y | N | S | N | D | N | R | P | S | Q | S | W | D | S | S | S | N | Y | V |
| ABGDF15-E | VL1-1e | S | G | S | S | S | N | I | G | V | L | Y | N | S | N | D | N | R | P | S | Q | S | W | D | S | S | S | N | Y | V |
| ABGDF15-G | VK1-O12 | R | A | S | Q | T | I | - | Y | - | R | S | L | A | G | A | S | I | L | Q | S | L | Q | R | Y | T | S | P | - | F | T |
| ABGDF15-D | VL-1e | S | G | S | S | S | N | I | G | V | L | Y | I | N | S | N | D | N | R | P | S | Q | S | W | D | S | S | S | N | Y | V |

SEQUENCE LISTING

```
<160> NUMBER OF SEQ ID NOS: 199

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
```

290                 295                 300

Cys His Cys Ile
305

<210> SEQ ID NO 2
<211> LENGTH: 1220
<212> TYPE: DNA
<213> ORGANISM: Homo sapiens

<400> SEQUENCE: 2

| | | | | |
|---|---|---|---|---|
| agtcccagct | cagagccgca | acctgcacag | ccatgcccgg | gcaagaactc | aggacggtga | 60 |
| atggctctca | gatgctcctg | gtgttgctgg | tgctctcgtg | gctgccgcat | ggggcgccc | 120 |
| tgtctctggc | cgaggcgagc | cgcgcaagtt | cccgggacc | ctcagagttg | cactccgaag | 180 |
| actccagatt | ccgagagttg | cggaaacgct | acgaggacct | gctaaccagg | ctgcgggcca | 240 |
| accagagctg | ggaagattcg | aacaccgacc | tcgtcccggc | ccctgcagtc | cggatactca | 300 |
| cgccagaagt | gcggctggga | tccggcggcc | acctgcacct | gcgtatctct | cgggccgccc | 360 |
| ttcccgaggg | gctccccgag | gcctcccgcc | ttcaccgggc | tctgttccgg | ctgtccccga | 420 |
| cggcgtcaag | gtcgtgggac | gtgacacgac | cgctgcggcg | tcagctcagc | cttgcaagac | 480 |
| cccaggcgcc | cgcgctgcac | ctgcgactgt | cgccgccgcc | gtcgcagtcg | gaccaactgc | 540 |
| tggcagaatc | ttcgtccgca | cggccccagc | tggagttgca | cttgcggccg | caagccgcca | 600 |
| gggggcgccg | cagagcgcgt | gcgcgcaacg | gggaccactg | tccgctcggg | cccgggcgtt | 660 |
| gctgccgtct | gcacacggtc | cgcgcgtcgc | tggaagacct | gggctgggcc | gattgggtgc | 720 |
| tgtcgccacg | ggaggtgcaa | gtgaccatgt | gcatcggcgc | gtgcccgagc | cagttccggg | 780 |
| cggcaaacat | gcacgcgcag | atcaagacga | gcctgcaccg | cctgaagccc | gacacggtgc | 840 |
| cagcgccctg | ctgcgtgccc | gccagctaca | atccatggt | gctcattcaa | aagaccgaca | 900 |
| ccggggtgtc | gctccagacc | tatgatgact | tgttagccaa | agactgccac | tgcatatgag | 960 |
| cagtcctggt | ccttccactg | tgcacctgcg | cggaggacgc | gacctcagtt | gtcctgccct | 1020 |
| gtggaatggg | ctcaaggttc | ctgagacacc | cgattcctgc | ccaaacagct | gtatttatat | 1080 |
| aagtctgtta | tttattatta | atttattggg | gtgaccttct | tggggactcg | ggggctggtc | 1140 |
| tgatggaact | gtgtatttat | ttaaaactct | ggtgataaaa | ataaagctgt | ctgaactgtt | 1200 |
| aaaaaaaaaa | aaaaaaaaaa | | | | | 1220 |

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Tyr Ser Phe Thr Asp Tyr Trp Ile Ser
1               5                   10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 4

Ile Ile Asp Pro Ser Gly Ser Tyr Thr Ile Tyr Ser Pro Ser Phe Gln
1               5                   10                  15

Gly

<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Ser Tyr Tyr Gly Gly Tyr Phe Asp Ile
1               5                   10

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Tyr Trp Ile Ser
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ile Ile Asp Pro Ser Gly Ser Tyr Thr Ile Tyr Ser Pro Ser Phe Gln
1               5                   10                  15

Gly

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Val Ser Tyr Tyr Gly Gly Tyr Phe Asp Ile
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 9

Gly Tyr Ser Phe Thr Asp Tyr
1               5

<210> SEQ ID NO 10
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asp Pro Ser Gly Ser Tyr
1               5

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Ser Tyr Tyr Gly Gly Tyr Phe Asp Ile
1               5                   10

<210> SEQ ID NO 12
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Trp Ile Ser Trp Val Arg Gln Met Pro Gly Lys Gly Leu Glu Trp Met
            35                  40                  45

Gly Ile Ile Asp Pro Ser Gly Ser Tyr Thr Ile Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Tyr Tyr Gly Gly Tyr Phe Asp Ile Trp Gly Gln Gly
                100                 105                 110

Thr Leu Val Thr Val Ser Ser
            115

<210> SEQ ID NO 13
<211> LENGTH: 357
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 13

```
gaagtgcaac tcgtgcagtc cggagccgaa gtgaaaaagc caggagagtc cctgaagatc      60
agctgcaagg gatccggata ctccttcacc gactactgga tttcgtgggt ccgccagatg     120
cccgggaagg gcctggagtg gatggggatc atcgatccgt ctggttccta cactatctac     180
tcgccgtcgt tccaaggaca ggtcaccatc tccgccgaca gtccattag caccgcgtat     240
ctgcagtgga gctcactgaa ggcctccgac accgcaatgt actactgcgc gcgggtgtca     300
tactacggcg gttactttga tatttggggc caggggactc tggtcactgt gtcgtcc       357
```

<210> SEQ ID NO 14
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Trp Ile Ser Trp Val Arg Gln Met Pro Gly Lys Gly Leu Glu Trp Met
        35                  40                  45

Gly Ile Ile Asp Pro Ser Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Tyr Tyr Gly Gly Tyr Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 15
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
gaagtgcaac tcgtgcagtc cggagccgaa gtgaaaaagc caggagagtc cctgaagatc    60
agctgcaagg gatccggata ctccttcacc gactactgga tttcgtgggt ccgccagatg   120
cccgggaagg gcctggagtg gatggggatc atcgatccgt ctggttccta cactatctac   180
tcgccgtcgt tccaaggaca ggtcaccatc tccgccgaca gtccattagc accgcgtat   240
ctgcagtgga gctcactgaa ggcctccgac accgcaatgt actactgcgc gcgggtgtca   300
tactacggcg gttactttga tatttggggc caggggactc tggtcactgt gtcgtccgct   360
agcaccaagg gcccaagtgt gtttcccctg gccccagca gcaagtctac ttccggcgga   420
actgctgccc tgggttgcct ggtgaaggac tacttccccg agcccgtgac agtgtcctgg   480
aactctgggg ctctgacttc cggcgtgcac accttcccg ccgtgctgca gagcagcggc   540
ctgtacagcc tgagcagcgt ggtgacagtg ccctccagct ctctgggaac ccagacctat   600
atctgcaacg tgaaccacaa gcccagcaac accaaggtgg acaagagagt ggagcccaag   660
agctgcgaca gaccccacac ctgcccccc tgcccagctc cagaactgct gggagggcct   720
tccgtgttcc tgttccccc caagcccaag gacaccctga tgatcagcag gacccccgag   780
gtgacctgcg tggtggtgga cgtgtcccac gaggacccag aggtgaagtt caactggtac   840
gtggacggcg tggaggtgca caacgccaag accaagccca gagaggagca gtacaacagc   900
acctacaggg tggtgtccgt gctgaccgtg ctgcaccagg actggctgaa cggcaaagaa   960
```

```
tacaagtgca aagtctccaa caaggccctg ccagccccaa tcgaaaagac aatcagcaag   1020
gccaagggcc agccacggga gccccaggtg tacaccctgc cccccagccg ggaggagatg   1080
accaagaacc aggtgtccct gacctgtctg gtgaagggct tctacccag cgatatcgcc    1140 gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagtccctga gcctgagccc cggcaag                                      1347
```

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

```
Arg Ala Ser Gln Ser Ile Ser Asn Asn Leu Asn
1               5                   10
```

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

```
Ala Ala Ser Asn Leu Gln Ser
1               5
```

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

```
Phe Gln Leu Asp His Ser Pro Phe Thr
1               5
```

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

```
Arg Ala Ser Gln Ser Ile Ser Asn Asn Leu Asn
1               5                   10
```

<210> SEQ ID NO 20
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ala Ala Ser Asn Leu Gln Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Phe Gln Leu Asp His Ser Pro Phe Thr
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gln Ser Ile Ser Asn Asn
1               5

<210> SEQ ID NO 23
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ala Ala Ser
1

<210> SEQ ID NO 24
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Leu Asp His Ser Pro Phe
1               5

<210> SEQ ID NO 25
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Leu Asp His Ser Pro Phe
                85                  90                  95

Thr Phe Gly Gln Gly Thr Lys Val Glu Ile Lys
            100                 105

<210> SEQ ID NO 26
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
gacattcaga tgacccagag cccttcctcc ctgtccgcct ccgtgggaga tcgcgtgacc      60
atcacttgcc gggccagcca gtcgatttca aacaacctga actggtacca gcagaaaccg     120
ggaaaggccc ccaagctgtt gatctacgcg gccagcaatc tccagtccgg cgtgccgtca     180
agattctccg ggagcggttc gggcactgac ttcaccctga ccatctcctc gctgcaaccc     240
gaagatttcg caacctacta ctgtttccaa ctggaccact ctccattcac atttgggcag     300
ggcaccaagg tcgagatcaa g                                               321

<210> SEQ ID NO 27
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Leu Asp His Ser Pro Phe
                85                  90                  95

```
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 28
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
gacattcaga tgacccagag cccttcctcc ctgtccgcct ccgtgggaga tcgcgtgacc    60
atcacttgcc gggccagcca gtcgatttca aacaacctga actggtacca gcagaaaccg   120
ggaaaggccc ccaagctgtt gatctacgcg gccagcaatc tccagtccgg cgtgccgtca   180
agattctccg ggagcggttc gggcactgac ttcaccctga ccatctcctc gctgcaaccc   240
gaagatttcg caacctacta ctgtttccaa ctggaccact ctccattcac atttgggcag   300
ggcaccaagg tcgagatcaa gcgtacggtg gccgctccca gcgtgttcat cttcccccccc  360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga gaagcataag gtgtacgcct gcgaggtgac ccaccagggc   600
ctgtccagcc ccgtgaccaa gagcttcaac aggggcgagt gc                      642
```

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

```
Gly Gly Thr Phe Ser Ser His Tyr Ile Asn
1               5                   10
```

<210> SEQ ID NO 30
<211> LENGTH: 17
<212> TYPE: PRT
<213> ORGANISM: Artificial Sequence
<220> FEATURE:

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Gly Ile Ile Pro Ala Phe Gly Gly Ala Asn Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Phe Gly Ser Val Tyr Val Ser Arg Tyr Ser Ser Tyr Tyr His Met Asp
1               5                   10                  15

Val

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Ser His Tyr Ile Asn
1               5

<210> SEQ ID NO 33
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Gly Ile Ile Pro Ala Phe Gly Gly Ala Asn Tyr Ala Gln Lys Phe Gln
1               5                   10                  15

Gly

<210> SEQ ID NO 34
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

Phe Gly Ser Val Tyr Val Ser Arg Tyr Ser Ser Tyr Tyr His Met Asp
1               5                   10                  15

Val

<210> SEQ ID NO 35

-continued

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Gly Thr Phe Ser Ser His
1               5

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ile Pro Ala Phe Gly Gly
1               5

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Phe Gly Ser Val Tyr Val Ser Arg Tyr Ser Ser Tyr Tyr His Met Asp
1               5                   10                  15

Val

<210> SEQ ID NO 38
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Tyr Ile Asn Trp Val Arg Gln Ala Pro Gly Gln Gly Leu Glu Trp Met
        35                  40                  45

Gly Gly Ile Ile Pro Ala Phe Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Ser Val Tyr Val Ser Arg Tyr Ser Ser Tyr Tyr His
                100                 105                 110

Met Asp Val Trp Gly Gln Gly Thr Leu Val Thr Val Ser Ser
```

<210> SEQ ID NO 39
<211> LENGTH: 378
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
caagtgcaac tcgtgcagtc gggagccgaa gtcaagaagc cggggagctc ggtgaaagtg    60
tcctgcaagg cctccggggg aactttcagc tcccactaca tcaactgggt cagacaggcg   120
cccggacagg ggttggaatg gatgggcgga atcatcccgg cgtttggcgg cgcgaactac   180
gcccagaagt tccagggtcg ggtcaccatt accgccgacg agtccacttc cactgcatac   240
atggagctgt cctcactgcg gagcgaagat accgccgtgt attactgcgc ccgcttcgga   300
tctgtgtacg tgtcccgcta ctcctcatac taccatatgg acgtctgggg acagggcacc   360
ctggtcacgg tgtcgtcc                                                 378
```

<210> SEQ ID NO 40
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Tyr Ile Asn Trp Val Arg Gln Ala Pro Gly Gln Gly Leu Glu Trp Met
        35                  40                  45

Gly Gly Ile Ile Pro Ala Phe Gly Gly Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Ser Val Tyr Val Ser Arg Tyr Ser Ser Tyr Tyr His
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205
```

| | | | | | | | | | | | |
|---|---|---|---|---|---|---|---|---|---|---|---|
| Cys | Asn | Val | Asn | His | Lys | Pro | Ser | Asn | Thr | Lys | Val | Asp | Lys | Arg | Val |
| | 210 | | | | 215 | | | | | 220 | |

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 41
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
caagtgcaac tcgtgcagtc gggagccgaa gtcaagaagc cggggagctc ggtgaaagtg     60
tcctgcaagg cctccggggg aactttcagc tcccactaca tcaactgggt cagacaggcg    120
cccggacagg ggttggaatg gatgggcgga atcatcccgg cgtttggcgg cgcgaactac    180
gcccagaagt tccagggtcg ggtcaccatt accgccgacg agtccacttc cactgcatac    240
atggagctgt cctcactgcg gagcgaagat accgccgtgt attactgcgc ccgcttcgga    300
tctgtgtacg tgtcccgcta ctcctcatac taccatatgg acgtctgggg acagggcacc    360
ctggtcacgg tgtcgtccgc tagcaccaag ggcccaagtg tgtttcccct ggccccagc    420 agcaagtcta cttccggcgg aactgctgcc ctgggttgcc tggtgaagga ctacttcccc    480
gagcccgtga cagtgtcctg gaactctggg gctctgactt ccggcgtgca caccttcccc    540
gccgtgctgc agagcagcgg cctgtacagc ctgagcagcg tggtgacagt gccctccagc    600

```
tctctgggaa cccagaccta tatctgcaac gtgaaccaca agcccagcaa caccaaggtg    660
gacaagagag tggagcccaa gagctgcgac aagacccaca cctgccccc ctgcccagct     720 ccagaactgc tgggagggcc ttccgtgttc ctgttccccc caagcccaa ggacaccctg     780 atgatcagca ggaccccga ggtgacctgc gtggtggtgg acgtgtccca cgaggaccca    840
gaggtgaagt tcaactggta cgtggacggc gtggaggtgc acaacgccaa gaccaagccc   900
agagaggagc agtacaacag cacctacagg gtggtgtccg tgctgaccgt gctgcaccag   960
gactggctga acggcaaaga atacaagtgc aaagtctcca acaaggccct gccagcccca   1020
atcgaaaaga caatcagcaa ggccaagggc cagccacggg agcccaggt gtacaccctg    1080 ccccccagcc gggaggagat gaccaagaac caggtgtccc tgacctgtct ggtgaagggc   1140
ttctacccca gcgatatcgc cgtggagtgg gagagcaacg gccagcccga gaacaactac   1200
aagaccaccc cccagtgct ggacagcgac ggcagcttct tcctgtacag caagctgacc    1260
gtggacaagt ccaggtggca gcagggcaac gtgttcagct gcagcgtgat gcacgaggcc   1320
ctgcacaacc actacaccca gaagtccctg agcctgagcc ccggcaag             1368
```

```
<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Arg Ala Ser Gln Thr Ile Tyr Arg Ser Leu Ala
1               5                   10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Ala Ser Ile Leu Gln Ser
1               5

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Leu Gln Arg Tyr Thr Ser Pro Phe Thr
1               5

<210> SEQ ID NO 45
<211> LENGTH: 11
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 45

Arg Ala Ser Gln Thr Ile Tyr Arg Ser Leu Ala
1               5                   10

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Ala Ser Ile Leu Gln Ser
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Leu Gln Arg Tyr Thr Ser Pro Phe Thr
1               5

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ser Gln Thr Ile Tyr Arg Ser
1               5

<210> SEQ ID NO 49
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Ala Ser
1

<210> SEQ ID NO 50
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

```
Arg Tyr Thr Ser Pro Phe
1               5
```

<210> SEQ ID NO 51
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Tyr Arg Ser
            20                  25                  30

Leu Ala Trp Tyr Gln Gln Lys Pro Gly Lys Ala Pro Lys Leu Leu Ile
        35                  40                  45

Tyr Gly Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Arg Tyr Thr Ser Pro Phe
                85                  90                  95

Thr Phe Gly Gln Gly Thr Lys Val Glu Ile Lys
            100                 105
```

<210> SEQ ID NO 52
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
gacattcaga tgacccagtc accctcctct ctctccgcat ccgtgggcga tcgcgtgacc    60
atcacctgtc gggccagcca gaccatctat agaagcctgg cctggtacca gcagaaaccg   120
ggaaaggccc caaagctgct gatctacggc gccagcattc tgcagtccgg ggtgccttcg   180
aggttctccg gatccgggtc gggaactgac ttcaccttga ccatctcgag cctgcagccg   240
gaggacttcg cgacttacta ctgcctgcaa cggtacacct cacccttttac cttcggacaa   300 ggcacaaagg tcgaaatcaa g                                              321
```

<210> SEQ ID NO 53
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Tyr Arg Ser
            20                  25                  30
```

Leu Ala Trp Tyr Gln Gln Lys Pro Gly Lys Ala Pro Lys Leu Leu Ile
            35                  40                  45

Tyr Gly Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Arg Tyr Thr Ser Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 54
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gacattcaga tgacccagtc accctcctct ctctccgcat ccgtgggcga tcgcgtgacc    60
atcacctgtc gggccagcca gaccatctat agaagcctgg cctggtacca gcagaaaccg    120
ggaaaggccc caaagctgct gatctacggc gccagcattc tgcagtccgg ggtgccttcg    180
aggttctccg gatccgggtc gggaactgac ttcaccttga ccatctcgag cctgcagccg    240
gaggacttcg cgacttacta ctgcctgcaa cggtacacct cccctttac cttcggacaa    300 ggcacaaagg tcgaaatcaa gcgtacggtg gccgctccca gcgtgttcat cttcccccc    360 agcgacgagc agctgaagag cggcaccgcc agcgtggtgt gcctgctgaa caacttctac    420 ccccggggagg ccaaggtgca gtggaaggtg gacaacgccc tgcagagcgg caacagccag    480
gagagcgtca ccgagcagga cagcaaggac tccacctaca gcctgagcag cacccctgacc    540 ctgagcaagg ccgactacga gaagcataag gtgtacgcct gcgaggtgac ccaccagggc    600
ctgtccagcc ccgtgaccaa gagcttcaac aggggcgagt gc    642

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Gly Thr Phe Arg Ser Tyr Ala Val Ser
1               5                   10

<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Ile Ile Pro Ile Phe Gly Thr Ala Asn Tyr Ala Gln Lys Phe Gln
1               5                   10                  15

Gly

<210> SEQ ID NO 57
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Pro Ile Ile Met Gly Tyr Gln Phe Gly Leu Phe Asp His
1               5                   10

<210> SEQ ID NO 58
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ser Tyr Ala Val Ser
1               5

<210> SEQ ID NO 59
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Ile Ile Pro Ile Phe Gly Thr Ala Asn Tyr Ala Gln Lys Phe Gln
1               5                   10                  15

Gly

<210> SEQ ID NO 60
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 60

Gly Pro Ile Ile Met Gly Tyr Gln Phe Gly Leu Phe Asp His
1               5                   10

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Gly Thr Phe Arg Ser Tyr
1               5

<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ile Pro Ile Phe Gly Thr
1               5

<210> SEQ ID NO 63
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Pro Ile Ile Met Gly Tyr Gln Phe Gly Leu Phe Asp His
1               5                   10

<210> SEQ ID NO 64
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95
Ala Arg Gly Pro Ile Ile Met Gly Tyr Gln Phe Gly Leu Phe Asp His
            100                 105                 110

Trp Gly Gln Gly Thr Leu Val Thr Val Ser Ser
            115                 120

<210> SEQ ID NO 65
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
caagtgcaac tcgtgcagtc gggggccgag gtcaagaagc ccggctcgtc cgtgaaagtg      60
tcctgcaagg cctccggagg aactttccgg tcatacgccg tgtcctgggt cagacaggcc     120
ccaggacagg gattggagtg gatgggaggc atcatcccga tttttggcac cgcgaactac     180
gcccagaagt tccagggccg cgtgaccatc actgccgacg aaagcacctc cacggcatac     240 atgaactgt caagcctgcg gtccgaagat accgcggtgt actattgcgc aaggggtccg     300
attatcatgg ggtaccagtt cgggctgttc gaccactggg gacagggaac cctggtcact     360
gtgtcgtcc                                                             369

<210> SEQ ID NO 66
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Ile Met Gly Tyr Gln Phe Gly Leu Phe Asp His
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
                180                 185                 190
Thr Val Pro Ser Ser Leu Gly Thr Gln Thr Tyr Ile Cys Asn Val
            195                 200                 205
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 67
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
caagtgcaac tcgtgcagtc gggggccgag gtcaagaagc ccggctcgtc cgtgaaagtg      60
tcctgcaagg cctccggagg aactttccgg tcatacgccg tgtcctgggt cagacaggcc    120
ccaggacagg gattggagtg gatgggaggc atcatcccga tttttggcac cgcgaactac    180
gcccagaagt tccagggccg cgtgaccatc actgccgacg aaagcacctc cacggcatac    240
atggaactgt caagcctgcg gtccgaagat accgcggtgt actattgcgc aagggggtccg    300 attatcatgg gtaccagtt cgggctgttc gaccactggg gacagggaac cctggtcact    360
gtgtcgtccg ctagcaccaa gggcccaagt gtgtttcccc tggccccag cagcaagtct    420
```

```
acttccggcg gaactgctgc cctgggttgc ctggtgaagg actacttccc cgagcccgtg    480
acagtgtcct ggaactctgg ggctctgact tccggcgtgc acaccttccc cgccgtgctg    540
cagagcagcg gcctgtacag cctgagcagc gtggtgacag tgccctccag ctctctggga    600
acccagacct atatctgcaa cgtgaaccac aagcccagca acaccaaggt ggacaagaga    660
gtggagccca gagctgcgca agacccacac ctgccccc cctgcccagc tccagaactg    720
ctgggagggc cttccgtgtt cctgttcccc cccaagccca aggacaccct gatgatcagc    780 aggaccccg aggtgacctg cgtggtggtg gacgtgtccc acgaggaccc agaggtgaag    840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaaag aatacaagtg caaagtctcc aacaaggccc tgccagcccc aatcgaaaag    1020
acaatcagca aggccaaggg ccagccacgg gagccccagg tgtacaccct gccccccagc    1080
cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                          1359
```

<210> SEQ ID NO 68
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ser Gly Asp Asn Ile Gly Ser His Ile Val Ser
1               5                   10

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Asp Lys Ser Asn Arg Pro Ser
1               5

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gln Thr Trp Asp Ser Ile Gly Ser Val Val
1               5                   10

-continued

```
<210> SEQ ID NO 71
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ser Gly Asp Asn Ile Gly Ser His Ile Val Ser
1               5                   10

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asp Lys Ser Asn Arg Pro Ser
1               5

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Thr Trp Asp Ser Ile Gly Ser Val Val
1               5                   10

<210> SEQ ID NO 74
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Asn Ile Gly Ser His Ile
1               5

<210> SEQ ID NO 75
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asp Lys Ser
1

<210> SEQ ID NO 76
<211> LENGTH: 7
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 76

Trp Asp Ser Ile Gly Ser Val
1               5

<210> SEQ ID NO 77
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser His Ile Val
            20                  25                  30

Ser Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Thr Trp Asp Ser Ile Gly Ser Val
                85                  90                  95

Val Phe Gly Gly Gly Thr Lys Leu Thr Val Leu
            100                 105

<210> SEQ ID NO 78
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
tcatatgaac tcacccaacc cctgtccgtg tccgtggccc tgggtcagac tgcccggatt      60
acctgttcgg gagacaacat cggaagccac atcgtgtcgt ggtaccagca gaaacccggc     120
caggcgccag tgctggtcat ctacgataag tccaaccgcc cgtccggaat cccggagagg     180
ttcagcgggt ccaatagcgg caacaccgca accctgacca tctcaagagc tcaggccggg     240
gatgaggccg actactactg ccaaacttgg gactcgattg gctccgtggt gttcggcggc     300
ggaactaagc tcacggtcct g                                               321

<210> SEQ ID NO 79
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ser Tyr Glu Leu Thr Gln Pro Leu Ser Val Ser Ala Leu Gly Gln
1               5                   10                  15

Thr Ala Arg Ile Thr Cys Ser Gly Asp Asn Ile Gly Ser His Ile Val
            20                  25                  30

Ser Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Thr Trp Asp Ser Ile Gly Ser Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 80
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
tcatatgaac tcacccaacc cctgtccgtg tccgtggccc tgggtcagac tgcccggatt    60
acctgttcgg gagacaacat cggaagccac atcgtgtcgt ggtaccagca gaaacccggc   120
caggcgccag tgctggtcat ctacgataag tccaaccgcc cgtccggaat cccggagagg   180
ttcagcgggt ccaatagcgg caacaccgca accctgacca tctcaagagc tcaggccggg   240
gatgaggccg actactactg ccaaacttgg gactcgattg gctccgtggt gttcggcggc   300
ggaactaagc tcacggtcct gggtcagcct aaggctgccc ccagcgtgac cctgttcccc   360
cccagcagcg aggagctgca ggccaacaag gccaccctgg tgtgcctgat cagcgacttc   420
tacccaggcg ccgtgaccgt ggcctggaag gccgacagca gccccgtgaa ggccggcgtg   480
gagaccacca cccccagcaa gcagagcaac aacaagtacg ccgccagcag ctacctgagc   540
ctgacccccg agcagtggaa gagccacagg tcctacagct gccaggtgac ccacgagggc   600
agcaccgtgg aaaagaccgt ggccccaacc gagtgcagc                          639

<210> SEQ ID NO 81
<211> LENGTH: 10

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gly Gly Thr Phe Arg Ser Tyr Ala Val Ser
1               5                   10

<210> SEQ ID NO 82
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Ile Ile Pro Ile Phe Gly Thr Ala Asn Tyr Ala Gln Lys Phe Gln
1               5                   10                  15

Gly

<210> SEQ ID NO 83
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gly Pro Ile Ile Met Gly Tyr Gln Phe Gly Leu Phe Asp His
1               5                   10

<210> SEQ ID NO 84
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Ser Tyr Ala Val Ser
1               5

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gly Ile Ile Pro Ile Phe Gly Thr Ala Asn Tyr Ala Gln Lys Phe Gln
1               5                   10                  15

Gly

<210> SEQ ID NO 86
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Pro Ile Ile Met Gly Tyr Gln Phe Gly Leu Phe Asp His
1               5                   10

<210> SEQ ID NO 87
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Gly Gly Thr Phe Arg Ser Tyr
1               5

<210> SEQ ID NO 88
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Ile Pro Ile Phe Gly Thr
1               5

<210> SEQ ID NO 89
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Pro Ile Ile Met Gly Tyr Gln Phe Gly Leu Phe Asp His
1               5                   10

<210> SEQ ID NO 90
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Ile Met Gly Tyr Gln Phe Gly Leu Phe Asp His
            100                 105                 110

Trp Gly Gln Gly Thr Leu Val Thr Val Ser Ser
        115                 120

<210> SEQ ID NO 91
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
caagtgcaac tcgtgcagtc gggggccgag gtcaagaagc ccggctcgtc cgtgaaagtg    60
tcctgcaagg cctccggagg aactttccgg tcatacgccg tgtcctgggt cagacaggcc   120
ccaggacagg gattggagtg gatgggaggc atcatcccga tttttggcac cgcgaactac   180
gcccagaagt tccagggccg cgtgaccatc actgccgacg aaagcacctc cacggcatac   240
atggaactgt caagcctgcg gtccgaagat accgcggtgt actattgcgc aaggggtccg   300
attatcatgg gctaccagtt cgggctgttc gaccactggg gacagggaac cctggtcact   360
gtgtcgtcc                                                           369

<210> SEQ ID NO 92
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Ile Met Gly Tyr Gln Phe Gly Leu Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 93
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93
caagtgcaac tcgtgcagtc gggggccgag gtcaagaagc ccggctcgtc cgtgaaagtg      60
tcctgcaagg cctccggagg aactttccgg tcatacgccg tgtcctgggt cagacaggcc    120
ccaggacagg gattgagtg gatgggaggc atcatcccga ttttggcac cgcgaactac    180 gcccagaagt tccagggccg cgtgaccatc actgccgacg aaagcacctc cacggcatac    240

```
atggaactgt caagcctgcg gtccgaagat accgcggtgt actattgcgc aagggggtccg    300 attatcatgg ggtaccagtt cgggctgttc gaccactggg gacagggaac cctggtcact    360
gtgtcgtccg ctagcaccaa gggcccaagt gtgtttcccc tggccccag cagcaagtct    420 acttccggcg gaactgctgc cctggggttgc ctggtgaagg actacttccc cgagcccgtg    480
acagtgtcct ggaactctgg ggctctgact tccggcgtgc acaccttccc cgccgtgctg    540
cagagcagcg gcctgtacag cctgagcagc gtggtgacag tgccctccag ctctctggga    600
acccagacct atatctgcaa cgtgaaccac aagcccagca acaccaaggt ggacaagaga    660
gtggagccca gagctgcga caagacccac acctgccccc cctgcccagc tccagaactg    720
ctgggagggc cttccgtgtt cctgttcccc ccaagcccca aggacaccct gatgatcagc    780
aggacccccg aggtgacctg cgtggtggtg gacgtgtccc acgaggaccc agaggtgaag    840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaaag aatacaagtg caaagtctcc aacaaggccc tgccagcccc aatcgaaaag    1020
acaatcagca aggccaaggg ccagccacgg gagcccagg tgtacaccct gcccccccagc    1080 cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                            1359
```

<210> SEQ ID NO 94
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ser Gly Asp Asn Ile Gly Ser His Ile Val Ser
1               5                   10

<210> SEQ ID NO 95
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asp Lys Ser Asn Arg Pro Ser
1               5

<210> SEQ ID NO 96
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 96

Gln Thr Trp Asp Ser Ile Gly Ser Val Val
1               5                   10

<210> SEQ ID NO 97
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ser Gly Asp Asn Ile Gly Ser His Ile Val Ser
1               5                   10

<210> SEQ ID NO 98
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Asp Lys Ser Asn Arg Pro Ser
1               5

<210> SEQ ID NO 99
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gln Thr Trp Asp Ser Ile Gly Ser Val Val
1               5                   10

<210> SEQ ID NO 100
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Asp Asn Ile Gly Ser His Ile
1               5

<210> SEQ ID NO 101
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Asp Lys Ser
1
```

```
<210> SEQ ID NO 102
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Trp Asp Ser Ile Gly Ser Val
1               5

<210> SEQ ID NO 103
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser His Ile Val
            20                  25                  30

Ser Trp Tyr Gln Gln Lys Pro Gly Gln Ser Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ile Gly Ser Val
                85                  90                  95

Val Phe Gly Gly Gly Thr Lys Leu Thr Val Leu
            100                 105

<210> SEQ ID NO 104
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
tcatacgagc ttacccagcc acctagcgtg tcagtcagcc ccgggcagac cgcctccatc        60
acttgctcgg gagacaacat cggctcccac atcgtgtcgt ggtatcagca gaagccgggc       120
cagtcgccgt gctcgtgat ctacgacaaa tccaatcgcc cgtccggaat ccccgaacgg        180
ttcagcggat ccaactccgg aaacactgcc accctgacta ttagcggcac ccaagcgatg       240
gatgaggctg actactactg ccaaacctgg gattccattg gtccgtggt gttcggtgga        300 ggaacgaagc tgaccgtgct g                                                 321

<210> SEQ ID NO 105
<211> LENGTH: 213
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 105

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser His Ile Val
            20                  25                  30

Ser Trp Tyr Gln Gln Lys Pro Gly Gln Ser Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ile Gly Ser Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 106
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
tcatacgagc ttacccagcc acctagcgtg tcagtcagcc cgggcagac cgcctccatc      60
acttgctcgg gagacaacat cggctcccac atcgtgtcgt ggtatcagca gaagccgggc    120
cagtcgccgg tgctcgtgat ctacgacaaa tccaatcgcc cgtccggaat ccccgaacgg    180
ttcagcggat ccaactccgg aaacactgcc accctgacta ttagcggcac ccaagcgatg    240
gatgaggctg actactactg ccaaacctgg gattccattg gtccgtggt gttcggtgga    300
ggaacgaagc tgaccgtgct gggccagcct aaggctgccc ccagcgtgac cctgttcccc    360
cccagcagcg aggagctgca ggccaacaag gccaccctgg tgtgcctgat cagcgacttc    420
tacccaggcg ccgtgaccgt ggcctggaag gccacagca gccccgtgaa ggccggcgtg    480
gagaccacca cccccagcaa gcagagcaac aacaagtacg ccgccagcag ctacctgagc    540
ctgacccccg agcagtggaa gagccacagg tcctacagct gccaggtgac ccacgagggc    600
```
agcaccgtgg aaaagaccgt ggccccaacc gagtgcagc                        639

<210> SEQ ID NO 107
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Tyr Ser Phe Thr Ser Tyr Trp Ile Gly
1               5                   10

<210> SEQ ID NO 108
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Val Ile Asp Pro Asp Gly Ser Tyr Thr Ile Tyr Ser Pro Ser Phe Gln
1               5                   10                  15

Gly

<210> SEQ ID NO 109
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Tyr Gly Arg Tyr Gly Thr Tyr Phe Asp Tyr
1               5                   10

<210> SEQ ID NO 110
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ser Tyr Trp Ile Gly
1               5

<210> SEQ ID NO 111
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Val Ile Asp Pro Asp Gly Ser Tyr Thr Ile Tyr Ser Pro Ser Phe Gln
1               5                   10                  15

Gly

<210> SEQ ID NO 112
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Tyr Gly Arg Tyr Gly Thr Tyr Phe Asp Tyr
1               5                   10

<210> SEQ ID NO 113
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Gly Tyr Ser Phe Thr Ser Tyr
1               5

<210> SEQ ID NO 114
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Asp Pro Asp Gly Ser Tyr
1               5

<210> SEQ ID NO 115
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Tyr Gly Arg Tyr Gly Thr Tyr Phe Asp Tyr
1               5                   10

<210> SEQ ID NO 116
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr

```
                  20                  25                  30

Trp Ile Gly Trp Val Arg Gln Met Pro Gly Lys Gly Leu Glu Trp Met
            35                  40                  45

Gly Val Ile Asp Pro Asp Gly Ser Tyr Thr Ile Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Gly Thr Tyr Phe Asp Tyr Trp Gly Gln Gly
            100                 105                 110

Thr Leu Val Thr Val Ser Ser
        115

<210> SEQ ID NO 117
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
gaagtccaac tcgtgcagtc cggagccgag gtcaagaagc ccggcgaatc gctgaagatt      60
agctgcaaag gctccggtta ctccttcacc tcttactgga ttggctgggt ccggcagatg     120
ccagggaagg gattggagtg gatgggagtg atcgacccgg acggatcata caccatctac     180
tcgccgagct ttcaaggaca ggtcaccatc tccgccgaca gtccatctc cactgcgtat      240 ctgcagtgga gctcactgaa ggcctccgat acggcaatgt actactgcgc gagatacgga    300
cgctacggga cttacttcga ttactggggc caggggaccc tcgtgactgt gtcgtcc       357

<210> SEQ ID NO 118
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Asp Pro Asp Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Gly Thr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 119
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 119
gaagtccaac tcgtgcagtc cggagccgag gtcaagaagc ccggcgaatc gctgaagatt     60
agctgcaaag gctccggtta ctccttcacc tcttactgga ttggctgggt ccggcagatg    120

-continued

```
ccagggaagg gattggagtg gatgggagtg atcgacccgg acggatcata caccatctac    180
tcgccgagct ttcaaggaca ggtcaccatc tccgccgaca agtccatctc cactgcgtat    240
ctgcagtgga gctcactgaa ggcctccgat acggcaatgt actactgcgc gagatacgga    300
cgctacggga cttacttcga ttactggggc caggggaccc tcgtgactgt gtcgtccgct    360
agcaccaagg gcccaagtgt gtttcccctg gccccagca gcaagtctac ttccggcgga    420
actgctgccc tgggttgcct ggtgaaggac tacttcccg agcccgtgac agtgtcctgg    480
aactctgggg ctctgacttc cggcgtgcac accttcccg ccgtgctgca gagcagcggc    540
ctgtacagcc tgagcagcgt ggtgacagtg ccctccagct ctctgggaac ccagacctat    600
atctgcaacg tgaaccacaa gcccagcaac accaaggtgg acaagagagt ggagcccaag    660
agctgcgaca gacccacac ctgcccccc tgcccagctc cagaactgct gggagggcct    720
tccgtgttcc tgttcccccc caagcccaag gacaccctga tgatcagcag gaccccgag    780 gtgacctgcg tggtggtgga cgtgtcccac gaggacccag aggtgaagtt caactggtac    840
gtggacggcg tggaggtgca acgccaag accaagccca gagaggagca gtacaacagc    900
acctacaggg tggtgtccgt gctgaccgtg ctgcaccagg actggctgaa cggcaaagaa    960
tacaagtgca aagtctccaa caaggccctg ccagccccaa tcgaaaagac aatcagcaag   1020
gccaagggcc agccacggga gccccaggtg tacaccctgc cccccagccg ggaggagatg   1080
accaagaacc aggtgtccct gacctgtctg gtgaagggct tctacccag cgatatcgcc   1140 gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagtccctga gcctgagccc cggcaag                                        1347
```

<210> SEQ ID NO 120
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 120

Ser Gly Ser Ser Ser Asn Ile Gly Val Leu Tyr Val Asn
1               5                   10

<210> SEQ ID NO 121
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 121

Ser Asn Asp Asn Arg Pro Ser
1               5

<210> SEQ ID NO 122
<211> LENGTH: 10
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 122

Gln Ser Trp Asp Ser Ser Ser Asn Tyr Val
1               5                   10

<210> SEQ ID NO 123
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Ser Gly Ser Ser Ser Asn Ile Gly Val Leu Tyr Val Asn
1               5                   10

<210> SEQ ID NO 124
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Ser Asn Asp Asn Arg Pro Ser
1               5

<210> SEQ ID NO 125
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gln Ser Trp Asp Ser Ser Ser Asn Tyr Val
1               5                   10

<210> SEQ ID NO 126
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ser Ser Ser Asn Ile Gly Val Leu Tyr
1               5

<210> SEQ ID NO 127
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127
```

Ser Asn Asp
1

<210> SEQ ID NO 128
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Trp Asp Ser Ser Ser Asn Tyr
1               5

<210> SEQ ID NO 129
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Val Leu
            20                  25                  30

Tyr Val Asn Trp Tyr Gln Gln Leu Pro Gly Thr Ala Pro Lys Leu Leu
        35                  40                  45

Ile Tyr Ser Asn Asp Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ser Ser Ser
                85                  90                  95

Asn Tyr Val Phe Gly Gly Gly Thr Lys Leu Thr Val Leu
            100                 105

<210> SEQ ID NO 130
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
caatcggtgc tgacccagcc cccttcggtg tccggagccc cgggccagag agtgaccatc       60
agctgctcgg gttcctctag caacatcggg gtgctctacg tgaactggta ccagcagctg      120
ccgggcaccg ccccaaagct gctgatctat agcaatgata accggccgtc cggagtgccc      180
gaccggttct ccggatcaaa gagcggcacc tccgcatcct ggccattac ggggctgcag       240 gcggaggacg aagctgatta ctactgtcaa tcgtgggact cctcatccaa ctacgtgttc      300
ggcggaggca ccaaactgac tgtcctg                                          327

<210> SEQ ID NO 131
<211> LENGTH: 215

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Val Leu
            20                  25                  30

Tyr Val Asn Trp Tyr Gln Gln Leu Pro Gly Thr Ala Pro Lys Leu Leu
        35                  40                  45

Ile Tyr Ser Asn Asp Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ser Ser Ser
                85                  90                  95

Asn Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 132
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132
caatcggtgc tgacccagcc cccttcggtg tccggagccc cgggccagag agtgaccatc    60
agctgctcgg gttcctctag caacatcggg gtgctctacg tgaactggta ccagcagctg   120
ccgggcaccg ccccaaagct gctgatctat agcaatgata accggccgtc cggagtgccc   180
gaccggttct ccggatcaaa gagcggcacc tccgcatcct tggccattac ggggctgcag   240
gcggaggacg aagctgatta ctactgtcaa tcgtgggact cctcatccaa ctacgtgttc   300
ggcggaggca ccaaactgac tgtcctgggt cagcctaagg ctgcccccag cgtgaccctg   360
ttccccccca gcagcgagga gctgcaggcc aacaaggcca ccctggtgtg cctgatcagc   420
gacttctacc caggcgccgt gaccgtggcc tggaaggccg acagcagccc cgtgaaggcc   480
```

```
ggcgtggaga ccaccacccc cagcaagcag agcaacaaca agtacgccgc cagcagctac      540
ctgagcctga cccccgagca gtggaagagc cacaggtcct acagctgcca ggtgacccac      600
gagggcagca ccgtggaaaa gaccgtggcc ccaaccgagt gcagc                     645
```

<210> SEQ ID NO 133
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 133

```
Gly Tyr Ser Phe Thr Ser Tyr Trp Ile Gly
1               5                   10
```

<210> SEQ ID NO 134
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

```
Val Ile Asp Pro Gly Gly Ser Tyr Thr Ile Tyr Ser Pro Ser Phe Gln
1               5                   10                  15
Gly
```

<210> SEQ ID NO 135
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

```
Tyr Gly Arg Tyr Gly Thr Tyr Phe Asp Tyr
1               5                   10
```

<210> SEQ ID NO 136
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 136

```
Ser Tyr Trp Ile Gly
1               5
```

<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 137

```
Val Ile Asp Pro Gly Gly Ser Tyr Thr Ile Tyr Ser Pro Ser Phe Gln
1               5                   10                  15

Gly

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Tyr Gly Arg Tyr Gly Thr Tyr Phe Asp Tyr
1               5                   10

<210> SEQ ID NO 139
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Gly Tyr Ser Phe Thr Ser Tyr
1               5

<210> SEQ ID NO 140
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Asp Pro Gly Gly Ser Tyr
1               5

<210> SEQ ID NO 141
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Tyr Gly Arg Tyr Gly Thr Tyr Phe Asp Tyr
1               5                   10

<210> SEQ ID NO 142
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Glu Val Gln Leu Val Gln Ser Gly Ala Glu Val Lys Lys Pro Gly Glu
```

```
1               5                   10                  15
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Asp Pro Gly Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Gly Thr Tyr Phe Asp Tyr Trp Gly Gln Gly
            100                 105                 110

Thr Leu Val Thr Val Ser Ser
            115
```

<210> SEQ ID NO 143
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143

```
gaagtgcaac tcgtgcagtc cggagccgag gtcaagaagc ccggagagtc cctgaagatc      60
agctgcaaag gatccggcta ctccttcact tcatactgga tcggttgggt ccggcagatg     120
ccgggaaagg gcctggaatg gatgggcgtg attgaccccg ggggctccta cacgatctac     180
tccccgtcgt tccaaggaca ggtcaccatt tcggccgata agagcatctc cactgcgtat     240
ctgcagtggt caagcctgaa ggcctctgac accgcaatgt actactgcgc gagatacggc     300
cgctacggga cttactttga ctactgggga cagggtaccc tcgtgaccgt gtcctcg       357
```

<210> SEQ ID NO 144
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 144

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Asp Pro Gly Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Gly Thr Tyr Phe Asp Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 145
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 145
gaagtgcaac tcgtgcagtc cggagccgag gtcaagaagc ccggagagtc cctgaagatc    60
```

```
agctgcaaag gatccggcta ctccttcact tcatactgga tcggttgggt ccggcagatg    120
ccgggaaagg ggctggaatg gatgggcgtg attgaccccg ggggctccta cacgatctac    180
tccccgtcgt tccaaggaca ggtcaccatt tcggccgata agagcatctc cactgcgtat    240
ctgcagtggt caagcctgaa ggcctctgac accgcaatgt actactgcgc gagatacggc    300
cgctacggga cttactttga ctactgggga cagggtaccc tcgtgaccgt gtcctcggct    360
agcaccaagg gcccaagtgt gtttcccctg gcccccagca gcaagtctac ttccggcgga    420
actgctgccc tgggttgcct ggtgaaggac tacttccccg agcccgtgac agtgtcctgg    480
aactctgggg ctctgacttc cggcgtgcac accttccccg ccgtgctgca gagcagcggc    540
ctgtacagcc tgagcagcgt ggtgacagtg ccctccagct ctctgggaac ccagacctat    600
atctgcaacg tgaaccacaa gcccagcaac accaaggtgg acaagagagt ggagcccaag    660
agctgcgaca gacccacac ctgcccccc tgcccagctc agaactgct gggagggcct    720 tccgtgttcc tgttcccccc caagcccaag gacaccctga tgatcagcag gacccccgag    780
gtgacctgcg tggtggtgga cgtgtcccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaagaa    960
tacaagtgca agtctccaa caaggccctg ccagccccaa tcgaaaagac aatcagcaag   1020
gccaagggcc agccacggga gccccaggtg tacaccctgc ccccagccg ggaggagatg   1080 accaagaacc aggtgtccct gacctgtctg gtgaagggct tctacccag cgatatcgcc   1140 gtggagtggg agagcaacgg ccagcccgag aacaactaca gaccaccc cccagtgctg   1200 gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagtccctga gcctgagccc cggcaag                                       1347
```

<210> SEQ ID NO 146
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ser Gly Ser Ser Ser Asn Ile Gly Val Leu Tyr Val Asn
1               5                   10

<210> SEQ ID NO 147
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Ser Asn Asp Asn Arg Pro Ser
1               5

<210> SEQ ID NO 148
<211> LENGTH: 10
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gln Ser Trp Asp Ser Ser Ser Asn Tyr Val
1               5                   10

<210> SEQ ID NO 149
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Ser Gly Ser Ser Ser Asn Ile Gly Val Leu Tyr Val Asn
1               5                   10

<210> SEQ ID NO 150
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ser Asn Asp Asn Arg Pro Ser
1               5

<210> SEQ ID NO 151
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Ser Trp Asp Ser Ser Ser Asn Tyr Val
1               5                   10

<210> SEQ ID NO 152
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Ser Ser Ser Asn Ile Gly Val Leu Tyr
1               5

<210> SEQ ID NO 153
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 153

Ser Asn Asp
1

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Trp Asp Ser Ser Ser Asn Tyr
1               5

<210> SEQ ID NO 155
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Val Leu
            20                  25                  30

Tyr Val Asn Trp Tyr Gln Gln Leu Pro Gly Thr Ala Pro Lys Leu Leu
        35                  40                  45

Ile Tyr Ser Asn Asp Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ser Ser Ser
                85                  90                  95

Asn Tyr Val Phe Gly Gly Gly Thr Lys Leu Thr Val Leu
            100                 105

<210> SEQ ID NO 156
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
caatcggtgc tgacccagcc cccttcggtg tccggagccc cgggccagag agtgaccatc      60
agctgctcgg gttcctctag caacatcggg gtgctctacg tgaactggta ccagcagctg     120
ccgggcaccg cccaaagct gctgatctat agcaatgata accggccgtc cggagtgccc     180
gaccggttct ccggatcaaa gagcggcacc tccgcatcct tggccattac ggggctgcag     240
gcggaggacg aagctgatta ctactgtcaa tcgtgggact cctcatccaa ctacgtgttc     300
ggcggaggca ccaaactgac tgtcctg                                         327

<210> SEQ ID NO 157
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

```
Gln Ser Val Leu Thr Gln Pro Pro Ser Val Ser Gly Ala Pro Gly Gln
1               5                   10                  15
Arg Val Thr Ile Ser Cys Ser Gly Ser Ser Ser Asn Ile Gly Val Leu
            20                  25                  30
Tyr Val Asn Trp Tyr Gln Gln Leu Pro Gly Thr Ala Pro Lys Leu Leu
        35                  40                  45
Ile Tyr Ser Asn Asp Asn Arg Pro Ser Gly Val Pro Asp Arg Phe Ser
    50                  55                  60
Gly Ser Lys Ser Gly Thr Ser Ala Ser Leu Ala Ile Thr Gly Leu Gln
65                  70                  75                  80
Ala Glu Asp Glu Ala Asp Tyr Tyr Cys Gln Ser Trp Asp Ser Ser Ser
                85                  90                  95
Asn Tyr Val Phe Gly Gly Gly Thr Lys Leu Thr Val Leu Gly Gln Pro
            100                 105                 110
Lys Ala Ala Pro Ser Val Thr Leu Phe Pro Pro Ser Ser Glu Glu Leu
        115                 120                 125
Gln Ala Asn Lys Ala Thr Leu Val Cys Leu Ile Ser Asp Phe Tyr Pro
    130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Thr Glu Cys Ser
    210                 215
```

<210> SEQ ID NO 158
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 158

```
caatcggtgc tgacccagcc cccttcggtg tccggagccc cgggccagag agtgaccatc      60
agctgctcgg gttcctctag caacatcggg gtgctctacg tgaactggta ccagcagctg     120
ccgggcaccg ccccaaagct gctgatctat agcaatgata accggccgtc cggagtgccc     180
gaccggttct ccggatcaaa gagcggcacc tccgcatcct tggccattac ggggctgcag     240
gcggaggacg aagctgatta ctactgtcaa tcgtgggact cctcatccaa ctacgtgttc     300
ggcggaggca ccaaactgac tgtcctgggt cagcctaagg ctgccccag cgtgaccctg      360
ttccccccca gcagcgagga gctgcaggcc aacaaggcca ccctggtgtg cctgatcagc     420
```

```
gacttctacc caggcgccgt gaccgtggcc tggaaggccg acagcagccc cgtgaaggcc      480
ggcgtggaga ccaccacccc cagcaagcag agcaacaaca agtacgccgc cagcagctac      540
ctgagcctga cccccgagca gtggaagagc cacaggtcct acagctgcca ggtgacccac      600
gagggcagca ccgtggaaaa gaccgtggcc ccaaccgagt gcagc                      645
```

<210> SEQ ID NO 159
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Gly Tyr Ser Phe Thr Ser Tyr Trp Ile Gly
1               5                   10

<210> SEQ ID NO 160
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Val Ile Asp Pro Ser Gly Ser Tyr Thr Ile Tyr Ser Pro Ser Phe Gln
1               5                   10                  15
Gly

<210> SEQ ID NO 161
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Tyr Gly Arg Tyr Gly Thr Tyr Phe Asp Tyr
1               5                   10

<210> SEQ ID NO 162
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Ser Tyr Trp Ile Gly
1               5

<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 163

Val Ile Asp Pro Ser Gly Ser Tyr Thr Ile Tyr Ser Pro Ser Phe Gln
1               5                   10                  15

Gly

<210> SEQ ID NO 164
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Tyr Gly Arg Tyr Gly Thr Tyr Phe Asp Tyr
1               5                   10

<210> SEQ ID NO 165
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Gly Tyr Ser Phe Thr Ser Tyr
1               5

<210> SEQ ID NO 166
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Asp Pro Ser Gly Ser Tyr
1               5

<210> SEQ ID NO 167
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Tyr Gly Arg Tyr Gly Thr Tyr Phe Asp Tyr
1               5                   10

<210> SEQ ID NO 168
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Asp Pro Ser Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Arg Tyr Gly Tyr Phe Asp Tyr Trp Gly Gln Gly
            100                 105                 110

Thr Leu Val Thr Val Ser Ser
        115
```

<210> SEQ ID NO 169
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169

```
gaagtgcaac tcgtgcagtc cggagccgag gtcaagaagc ccggagaatc cctgaagatt      60
agctgcaagg gctccggata ctcattcact tcatattgga tcggctgggt ccggcagatg     120
ccggggaagg gctggagtg gatgggagtg atcgaccgt ccggttccta caccatctac       180
tcgccaagct tccaaggaca ggtcaccatc tctgccgata gtcgatttc acggcatac       240
ttgcagtggt cgtccctgaa agcgtccgac actgcgatgt actactgtgc ccgctacgga    300
agatacggca cctactttga ctactggggc caggggactc tcgtgaccgt gtccagc       357
```

<210> SEQ ID NO 170
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 170

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Val Ile Asp Pro Ser Gly Ser Tyr Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg Tyr Gly Arg Tyr Gly Thr Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 171
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 171

```
gaagtgcaac tcgtgcagtc cggagccgag gtcaagaagc ccggagaatc cctgaagatt    60
agctgcaagg gctccggata ctcattcact tcatattgga tcggctgggt ccggcagatg   120
ccggggaagg ggctggagtg gatgggagtg atcgacccgt ccggttccta caccatctac   180
tcgccaagct tccaaggaca ggtcaccatc tctgccgata gtcgatttc acggcatac    240
ttgcagtggt cgtccctgaa agcgtccgac actgcgatgt actactgtgc ccgctacgga   300
agatacggca cctactttga ctactggggc caggggactc tcgtgaccgt gtccagcgct   360
agcaccaagg gcccaagtgt gtttcccctg gccccagca gcaagtctac ttccggcgga   420
actgctgccc tgggttgcct ggtgaaggac tacttccccg agcccgtgac agtgtcctgg   480
aactctgggg ctctgacttc cggcgtgcac accttcccg ccgtgctgca gagcagcggc   540
ctgtacagcc tgagcagcgt ggtgacagtg ccctccagct ctctgggaac ccagacctat   600
atctgcaacg tgaaccacaa gcccagcaac accaaggtgg acaagagagt ggagcccaag   660
agctgcgaca gacccacac ctgcccccccc tgcccagctc cagaactgct gggagggcct   720
tccgtgttcc tgttcccccc caagcccaag gacaccctga tgatcagcag gaccccgag   780
gtgacctgcg tggtggtgga cgtgtcccac gaggacccag aggtgaagtt caactggtac   840
gtggacggcg tggaggtgca aacgccaag accaagccca gagaggagca gtacaacagc   900
acctacaggg tggtgtccgt gctgaccgtg ctgcaccagg actggctgaa cggcaaagaa   960
tacaagtgca aagtctccaa caaggccctg ccagcccaa tcgaaaagac aatcagcaag  1020
gccaagggc agccacggga gccccaggtg tacaccctgc cccccagccg ggaggagatg  1080
accaagaacc aggtgtccct gacctgtctg gtgaagggct tctaccccag cgatatcgcc  1140
gtggagtggg agagcaacgg ccagcccgag aacaactaca agaccacccc ccagtgctg   1200
gacagcgacg gcagcttctt cctgtacagc aagctgaccg tggacaagtc caggtggcag  1260
cagggcaacg tgttcagctg cagcgtgatg cacgaggccc tgcacaacca ctacacccag  1320
aagtccctga gcctgagccc cggcaag                                     1347
```

<210> SEQ ID NO 172
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 172

Ser Gly Ser Ser Ser Asn Ile Gly Val Leu Tyr Val Asn
1               5                   10

<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 173

Ser Asn Asp Asn Arg Pro Ser
1               5

```
<210> SEQ ID NO 174
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Gln Ser Trp Asp Ser Ser Ser Asn Tyr Val
1               5                   10

<210> SEQ ID NO 175
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Ser Gly Ser Ser Ser Asn Ile Gly Val Leu Tyr Val Asn
1               5                   10

<210> SEQ ID NO 176
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Ser Asn Asp Asn Arg Pro Ser
1               5

<210> SEQ ID NO 177
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gln Ser Trp Asp Ser Ser Ser Asn Tyr Val
1               5                   10

<210> SEQ ID NO 178
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ser Ser Ser Asn Ile Gly Val Leu Tyr
1               5

<210> SEQ ID NO 179
<211> LENGTH: 3
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 179

Ser Asn Asp
1

<210> SEQ ID NO 180
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Trp Asp Ser Ser Ser Asn Tyr
1               5

<210> SEQ ID NO 181
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Val Leu
            20                  25                  30

Tyr Val Asn Trp Tyr Gln Gln Leu Pro Gly Thr Ala Pro Lys Leu Leu
        35                  40                  45

Ile Tyr Ser Asn Asp Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ser Ser Ser
                85                  90                  95

Asn Tyr Val Phe Gly Gly Gly Thr Lys Leu Thr Val Leu
            100                 105

<210> SEQ ID NO 182
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
caatcggtgc tgacccagcc cccttcggtg tccggagccc cgggccagag agtgaccatc      60
agctgctcgg gttcctctag caacatcggg gtgctctacg tgaactggta ccagcagctg     120
ccgggcaccg ccccaaagct gctgatctat agcaatgata accggccgtc cggagtgccc     180
gaccggttct ccggatcaaa gagcggcacc tccgcatcct tggccattac ggggctgcag     240
gcggaggacg aagctgatta ctactgtcaa tcgtgggact cctcatccaa ctacgtgttc     300

```
ggcggaggca ccaaactgac tgtcctg                                        327
```

<210> SEQ ID NO 183
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 183

```
Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Val Leu
            20                  25                  30

Tyr Val Asn Trp Tyr Gln Gln Leu Pro Gly Thr Ala Pro Lys Leu Leu
        35                  40                  45

Ile Tyr Ser Asn Asp Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Trp Asp Ser Ser Ser
                85                  90                  95

Asn Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 184
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 184

```
caatcggtgc tgacccagcc cccttcggtg tccggagccc cgggccagag agtgaccatc    60
agctgctcgg gttcctctag caacatcggg gtgctctacg tgaactggta ccagcagctg   120
ccgggcaccg ccccaaagct gctgatctat agcaatgata accggccgtc cggagtgccc   180
gaccggttct ccgatcaaa gagcggcacc tccgcatcct tggccattac ggggctgcag   240
gcggaggacg aagctgatta ctactgtcaa tcgtgggact cctcatccaa ctacgtgttc   300
```

```
ggcggaggca ccaaactgac tgtcctgggt cagcctaagg ctgccccag cgtgaccctg    360 ttccccccca gcagcgagga gctgcaggcc aacaaggcca ccctggtgtg cctgatcagc    420
gacttctacc caggcgccgt gaccgtggcc tggaaggccg acagcagccc cgtgaaggcc    480
ggcgtggaga ccaccacccc cagcaagcag agcaacaaca agtacgccgc cagcagctac    540
ctgagcctga cccccgagca gtggaagagc cacaggtcct acagctgcca ggtgacccac    600
gagggcagca ccgtggaaaa gaccgtggcc ccaaccgagt gcagc                    645
```

```
<210> SEQ ID NO 185
<211> LENGTH: 7
<212> TYPE: PRT
<213> ORGANISM: Homo sapiens

<400> SEQUENCE: 185

Arg Gly Arg Arg Arg Ala Arg
1               5

<210> SEQ ID NO 186
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 186

His His His His His His
1               5

<210> SEQ ID NO 187
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser His Ile Val
            20                  25                  30

Ser Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Ser Ile Gly Ser Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160
```

```
Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 188
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (5)..(5)
<223> OTHER INFORMATION: /replace="Thr" or "Ser"
<220> FEATURE:
<221> NAME/KEY: VARIANT
<222> LOCATION: (6)..(6)
<223> OTHER INFORMATION: /replace="Asp"
<220> FEATURE:
<221> NAME/KEY: VARIANT
<222> LOCATION: (7)..(7)
<223> OTHER INFORMATION: /replace="His"
<220> FEATURE:
<221> NAME/KEY: VARIANT
<222> LOCATION: (8)..(8)
<223> OTHER INFORMATION: /replace="Trp" or "Tyr"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (10)..(10)
<223> OTHER INFORMATION: /replace="Gly" or "Asn"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 188

Gly Tyr Ser Phe Arg Ser Tyr Ala Val Ser
1               5                   10

<210> SEQ ID NO 189
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ile" or "Val"
```

```
<220> FEATURE:
<221> NAME/KEY: VARIANT
<222> LOCATION: (3)..(3)
<223> OTHER INFORMATION: /replace="Asp"
<220> FEATURE:
<221> NAME/KEY: VARIANT
<222> LOCATION: (5)..(5)
<223> OTHER INFORMATION: /replace="Ser" or "Gly" or "Ala" or "Asp"
<220> FEATURE:
<221> NAME/KEY: VARIANT
<222> LOCATION: (6)..(6)
<223> OTHER INFORMATION: /replace="Gly"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Tyr" or "Gly"
<220> FEATURE:
<221> NAME/KEY: VARIANT
<222> LOCATION: (9)..(9)
<223> OTHER INFORMATION: /replace="Thr"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (12)..(12)
<223> OTHER INFORMATION: /replace="Ser"
<220> FEATURE:
<221> NAME/KEY: VARIANT
<222> LOCATION: (13)..(13)
<223> OTHER INFORMATION: /replace="Pro"
<220> FEATURE:
<221> NAME/KEY: VARIANT
<222> LOCATION: (14)..(14)
<223> OTHER INFORMATION: /replace="Ser"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 189

Gly Ile Ile Pro Ile Phe Gly Thr Ala Asn Tyr Ala Gln Lys Phe Gln
1               5                   10                  15

Gly

<210> SEQ ID NO 190
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val" or "Tyr" or "Phe"
<220> FEATURE:
<221> NAME/KEY: VARIANT
<222> LOCATION: (2)..(2)
<223> OTHER INFORMATION: /replace="Ser" or "Gly"
<220> FEATURE:
<221> NAME/KEY: VARIANT
<222> LOCATION: (3)..(3)
<223> OTHER INFORMATION: /replace="Tyr" or "Arg" or "Ser"
<220> FEATURE:
<221> NAME/KEY: VARIANT
<222> LOCATION: (4)..(4)
<223> OTHER INFORMATION: /replace="Tyr" or "Val"
```

```
<220> FEATURE:
<221> NAME/KEY: VARIANT
<222> LOCATION: (5)..(5)
<223> OTHER INFORMATION: /replace="Gly" or "Tyr"
<220> FEATURE:
<221> NAME/KEY: VARIANT
<222> LOCATION: (6)..(6)
<223> OTHER INFORMATION: /replace="Thr" or "Val"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Phe" or "Arg"
<220> FEATURE:
<221> NAME/KEY: VARIANT
<222> LOCATION: (9)..(9)
<223> OTHER INFORMATION: /replace="Tyr" or " "
<220> FEATURE:
<221> NAME/KEY: VARIANT
<222> LOCATION: (10)..(10)
<223> OTHER INFORMATION: /replace="Ser" or " "
<220> FEATURE:
<221> NAME/KEY: VARIANT
<222> LOCATION: (11)..(11)
<223> OTHER INFORMATION: /replace="Ser" or " "
<220> FEATURE:
<221> NAME/KEY: VARIANT
<222> LOCATION: (12)..(12)
<223> OTHER INFORMATION: /replace="Tyr" or " "
<220> FEATURE:
<221> NAME/KEY: VARIANT
<222> LOCATION: (13)..(13)
<223> OTHER INFORMATION: /replace="Tyr" or " "
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace="Met" or " "
<220> FEATURE:
<221> NAME/KEY: VARIANT
<222> LOCATION: (17)..(17)
<223> OTHER INFORMATION: /replace="Ile" or "Tyr" or "Val"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 190

Gly Pro Ile Ile Met Gly Tyr Gln Phe Gly Leu Phe Tyr His Met Asp
1               5                   10                  15

His

<210> SEQ ID NO 191
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Arg"
<220> FEATURE:
<221> NAME/KEY: VARIANT
<222> LOCATION: (2)..(2)
<223> OTHER INFORMATION: /replace="Ala"
```

```
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Gln" or "Ser"
<220> FEATURE:
<221> NAME/KEY: VARIANT
<222> LOCATION: (5)..(5)
<223> OTHER INFORMATION: /replace="Ser" or "Thr"
<220> FEATURE:
<221> NAME/KEY: VARIANT
<222> LOCATION: (6)..(6)
<223> OTHER INFORMATION: /replace="Ile" or "Asn"
<220> FEATURE:
<221> NAME/KEY: VARIANT
<222> LOCATION: (7)..(7)
<223> OTHER INFORMATION: /replace="Ile" or "Tyr"
<220> FEATURE:
<221> NAME/KEY: VARIANT
<222> LOCATION: (8)..(8)
<223> OTHER INFORMATION: /replace=" "
<220> FEATURE:
<221> NAME/KEY: VARIANT
<222> LOCATION: (9)..(9)
<223> OTHER INFORMATION: /replace=" "
<220> FEATURE:
<221> NAME/KEY: VARIANT
<222> LOCATION: (10)..(10)
<223> OTHER INFORMATION: /replace="Asn" or "Leu" or "Arg"
<220> FEATURE:
<221> NAME/KEY: VARIANT
<222> LOCATION: (11)..(11)
<223> OTHER INFORMATION: /replace="Asn" or "Tyr" or "Ser"
<220> FEATURE:
<221> NAME/KEY: VARIANT
<222> LOCATION: (12)..(12)
<223> OTHER INFORMATION: /replace="Leu"
<220> FEATURE:
<221> NAME/KEY: VARIANT
<222> LOCATION: (13)..(13)
<223> OTHER INFORMATION: /replace="Asn" or "Ala"
<220> FEATURE:
<221> NAME/KEY: MISC_FEATURE
<222> LOCATION: (1)..(13)
<223> OTHER INFORMATION: /note="Variant residues given in the sequence
      have no preference with respect to those in the annotations
      for variant positions"

<400> SEQUENCE: 191

Ser Gly Asp Asn Ile Gly Ser Gly Val His Ile Val Ser
1               5                   10

<210> SEQ ID NO 192
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala" or "Ser" or "Gly"
<220> FEATURE:
<221> NAME/KEY: VARIANT
<222> LOCATION: (2)..(2)
<223> OTHER INFORMATION: /replace="Ala" or "Asn"
<220> FEATURE:
<221> NAME/KEY: VARIANT
<222> LOCATION: (3)..(3)
<223> OTHER INFORMATION: /replace="Asp"
<220> FEATURE:
<221> NAME/KEY: VARIANT
```

```
<222> LOCATION: (4)..(4)
<223> OTHER INFORMATION: /replace="Ile"
<220> FEATURE:
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (6)..(6)
<223> OTHER INFORMATION: /replace="Gln"
<220> FEATURE:
<221> NAME/KEY: MISC_FEATURE
<222> LOCATION: (1)..(7)
<223> OTHER INFORMATION: /note="Variant residues given in the sequence
      have no preference with respect to those in the annotations
      for variant positions"

<400> SEQUENCE: 192

Asp Lys Ser Asn Arg Pro Ser
1               5

<210> SEQ ID NO 193
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Phe" or "Leu"
<220> FEATURE:
<221> NAME/KEY: VARIANT
<222> LOCATION: (2)..(2)
<223> OTHER INFORMATION: /replace="Gln" or "Ser"
<220> FEATURE:
<221> NAME/KEY: VARIANT
<222> LOCATION: (3)..(3)
<223> OTHER INFORMATION: /replace="Leu" or "Arg"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (5)..(5)
<223> OTHER INFORMATION: /replace="His" or "Thr"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Pro" or "Ser"
<220> FEATURE:
<221> NAME/KEY: VARIANT
<222> LOCATION: (8)..(8)
<223> OTHER INFORMATION: /replace="Asn" or " "
<220> FEATURE:
<221> NAME/KEY: VARIANT
<222> LOCATION: (9)..(9)
<223> OTHER INFORMATION: /replace="Phe" or "Tyr"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 193
```

```
Gln Thr Trp Asp Ser Ile Gly Ser Val Val
1               5                  10
```

```
<210> SEQ ID NO 194
<211> LENGTH: 69
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194
```

```
Gly Gly Thr Phe Arg Ser Tyr Ala Val Ser Gly Ile Ile Pro Ile Phe
1               5                   10                  15

Gly Thr Ala Asn Tyr Ala Gln Lys Phe Gln Gly Gly Pro Ile Ile Met
            20                  25                  30

Gly Tyr Gln Phe Gly Leu Phe Asp His Ser Gly Asp Asn Ile Gly Ser
        35                  40                  45

His Ile Val Ser Asp Lys Ser Asn Arg Pro Ser Gln Thr Trp Asp Ser
    50                  55                  60

Ile Gly Ser Val Val
65
```

```
<210> SEQ ID NO 195
<211> LENGTH: 64
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195
```

```
Gly Tyr Ser Phe Thr Asp Tyr Trp Ile Ser Ile Ile Asp Pro Ser Gly
1               5                   10                  15

Ser Tyr Thr Ile Tyr Ser Pro Ser Phe Gln Gly Val Ser Tyr Tyr Gly
            20                  25                  30

Gly Tyr Phe Asp Ile Arg Ala Ser Gln Ser Ile Ser Asn Asn Leu Asn
        35                  40                  45

Ala Ala Ser Asn Leu Gln Ser Phe Gln Leu Asp His Ser Pro Phe Thr
    50                  55                  60
```

```
<210> SEQ ID NO 196
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196
```

```
Gly Tyr Ser Phe Thr Ser Tyr Trp Ile Gly Val Ile Asp Pro Ser Gly
1               5                   10                  15

Ser Tyr Thr Ile Tyr Ser Pro Ser Phe Gln Gly Tyr Gly Arg Tyr Gly
            20                  25                  30

Thr Tyr Phe Asp Tyr Ser Gly Ser Ser Asn Ile Gly Val Leu Tyr
        35                  40                  45

Val Asn Ser Asn Asp Asn Arg Pro Ser Gln Ser Trp Asp Ser Ser Ser
    50                  55                  60
```

```
Asn Tyr Val
 65

<210> SEQ ID NO 197
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Gly Tyr Ser Phe Thr Ser Tyr Trp Ile Gly Val Ile Asp Pro Gly Gly
 1               5                  10                  15

Ser Tyr Thr Ile Tyr Ser Pro Ser Phe Gln Gly Tyr Gly Arg Tyr Gly
            20                  25                  30

Thr Tyr Phe Asp Tyr Ser Gly Ser Ser Ser Asn Ile Gly Val Leu Tyr
        35                  40                  45

Val Asn Ser Asn Asp Asn Arg Pro Ser Gln Ser Trp Asp Ser Ser Ser
    50                  55                  60

Asn Tyr Val
 65

<210> SEQ ID NO 198
<211> LENGTH: 71
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Gly Gly Thr Phe Ser Ser His Tyr Ile Asn Gly Ile Ile Pro Ala Phe
 1               5                  10                  15

Gly Gly Ala Asn Tyr Ala Gln Lys Phe Gln Gly Phe Gly Ser Val Tyr
            20                  25                  30

Val Ser Arg Tyr Ser Ser Tyr Tyr His Met Asp Val Arg Ala Ser Gln
        35                  40                  45

Thr Ile Tyr Arg Ser Leu Ala Gly Ala Ser Ile Leu Gln Ser Leu Gln
    50                  55                  60

Arg Tyr Thr Ser Pro Phe Thr
 65                  70

<210> SEQ ID NO 199
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Gly Tyr Ser Phe Thr Ser Tyr Trp Ile Gly Val Ile Asp Pro Asp Gly
 1               5                  10                  15

Ser Tyr Thr Ile Tyr Ser Pro Ser Phe Gln Gly Tyr Gly Arg Tyr Gly
            20                  25                  30

Thr Tyr Phe Asp Tyr Ser Gly Ser Ser Ser Asn Ile Gly Val Leu Tyr
        35                  40                  45
```

```
Val Asn Ser Asn Asp Asn Arg Pro Ser Gln Ser Trp Asp Ser Ser Ser
    50                  55                  60

Asn Tyr Val
65
```

ANTIBODIES AGAINST GROWTH DIFFERENTIATION FACTOR 15 AND USES THEREOF

CROSS REFERENCE TO RELATED APPLICATIONS

This application is a U.S. National Phase filing of International Serial No. PCT/US2017/029636 filed Apr. 26, 2017, and claims priority to U.S. Application Ser. No. 62/328,564 filed Apr. 27, 2016, the contents of each of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 26, 2017, is named N2067-7107WO-_SL.txt and is 139,611 bytes in size. Throughout the text of this application, should there be a discrepancy between the text of the specification (e.g., Table 1) and the sequence listing, the text of the specification shall prevail.

BACKGROUND

Decreased appetite and weight loss are associated with adverse outcomes in multiple conditions, including anorexia nervosa, human aging, cancer, heart failure, chronic obstructive pulmonary disorder and renal failure. Anorexia is often associated with cachexia: a complex metabolic syndrome characterized by excessive loss of muscle mass with or without loss of fat mass that is more than expected for the decreased energy intake. This debilitating condition dramatically shortens lifespan and reduces quality of life.

Under normal circumstances, animals and humans respond to malnourishment with a complex neuroendocrine response that ultimately leads to an increase in appetite, a relative sparing of lean body mass and burning of fat stores, and an overall decrease in basal metabolic rate (Webber & Macdonald, 1994, *Brit. J. Nutr.* 71:437-447; Ahima et al., 1996, *Nature* 382:250-252). In contrast, in some diseases a devastating pathological state of malnutrition known as cachexia arises, brought about by a combination of a decrease in appetite and an increase in metabolic rate and metabolism of both fat and lean body mass, producing a relative wasting of lean body mass (Tisdale, 1997, *J. Natl. Cancer Inst.* 89: 1763-1773; Inui, 1999, *Cancer Res.* 59: 4493-4501; Fong et al., 1989, *Amer. J. Phys.* 256: R659-R665; Bruera, 1997, *Brit. Med. J.* 315: 1219-1222; Emery, 1999, *Nutrition* 15: 600-603). This combination is found in a number of disorders including cancer, cystic fibrosis, AIDS, rheumatoid arthritis, ALS, renal failure, wasting disorders, and hip fracture (Tisdale, 1997, ibid.).

The severity of cachexia in many illnesses may be a determining factor in both quality of life, and in eventual mortality (Tisdale, 1997, ibid.; Larkin, 1998, *Lancet* 351: 1336). Indeed, body mass retention in AIDS patients has a stronger correlation with survival than any other current measure of the disease (Kotler et al., 1989, *Amer. J. Clin. Nutr.* 50: 444-447). Many different tumor types have been studied and it is a common finding that tumor-bearing animals die from cachexia and exhaustion of metabolic fuels, rather than from metastasis or infection (Svaninger et al., 1987, *J. Natl. Cancer Inst.* 78: 943-950; Emery, 1999, *Nutrition* 15: 600-603; Svaninger et al., 1989, *Eur. J. Cancer Clin. Oncol.* 25: 1295-1302; Emery et al., 1984, *Cancer Res.* 44: 2779-2784). Cachexia is commonly observed in patients with cancer, particularly in children and elderly individuals (Bruera, 1997, ibid.). The resulting malnutrition and loss of lean body mass reduces the quality of life for the affected individual and compromises recovery by decreasing tolerance to therapy and increasing post-surgical complications (Larkin, 1998, ibid.; Inui, 1999, ibid.). An example of anorexia occurs in human aging. Elderly frail patients typically show an almost complete absence of hunger during fasting and postprandial periods (Serra-Prat et al., 2013, *Neurogastroenterol Motil.* 25(4):291-e245).

Tumor growth is associated with profound metabolic and neurochemical alterations, which can lead to the onset of the anorexia cachexia syndrome. Anorexia is associated with the loss of the desire to eat, while cachexia results from progressive wasting of skeletal muscle mass and to a lesser extent adipose tissue, occurring even before weight loss becomes apparent. Cancer anorexia-cachexia syndrome is highly prevalent among cancer patients, has a large impact on morbidity and mortality, and impinges on patient quality of life. However, its clinical relevance is frequently overlooked, and treatments are usually only attempted during advanced stages of the disease (Laviano A. et al, *Nat. Clin. Pract. Oncol.* 3:158-65 (2005)).

Growth Differentiation Factor 15 (GDF15) is a divergent member of the TGFβ superfamily, and is also referred to as macrophage inhibitory cytokine 1 (MIC1) (Bootcov M R, 1997, *Proc Natl Acad Sci* 94: 11514-9), placental bone morphogenetic factor (PLAB) (Hromas R 1997, *Biochim Biophys Acta.* 1354:40-4), placental transforming growth factor beta (PTGFB) (Lawton L N 1997, *Gene.* 203: 17-26), prostate derived factor (PDF) (Paralkar VM 1998, *J Biol Chem.* 273: 13760-7), and nonsteroidal antiinflammatory drug-activated gene (NAG-1) (Baek S J 2001, *J Biol Chem.* 276: 33384-92). The mature GDF15 peptide shares low homology with other family members (Katoh M 2006, *Int J Mol Med.* 17:951-5). GDF15 is synthesized as a large precursor protein that is cleaved at the dibasic cleavage site to release the carboxyterminal mature peptide. Human full-length precursor contains 308 amino acids and is cleaved at the RGRRRAR (SEQ ID NO:185) cleavage site to produce the mature GDF peptide. Naturally occurring GDF15 is a 25 KD homodimer of the mature peptide covalently linked by one inter-chain disulfide bond.

GDF15 is reported to be relevant to a number of different physiological and pathologic conditions. For example, studies of GDF15 knockout and transgenic mice suggest that GDF15 may be protective against ischemic/reperfusion- or overload-induced heart injury (Kempf T, 2006, *Circ Res.* 98:351-60; Xu J, 2006, *Circ Res.* 98:342-50), protective against aging-associated motor neuron and sensory neuron loss (Strelau J, 2009, *J Neurosci.* 29: 13640-8), mildly protective against metabolic acidosis in kidney, and may cause cachexia in cancer patients (Johnen H 2007 *Nat Med.* 11: 1333-40). GDF15 is also reported to be protective against carcinogen- or Apc mutation-induced neoplasia in intestine and lung (Baek S J 2006, *Gastroenterology.* 131: 1553-60; Cekanova M 2009, *Cancer Prev Res* 2:450-8).

GDF15 has anorexigenic effects, particularly in cancer (Brown D. A. Clinical *Cancer Res* 2003; 9:2642-2650; Koopmann J Clinical Cancer Res 2006; 12:442-446). Substantial elevation of circulating MIC-1/GDF15 levels in cancers and other diseases such as chronic renal or cardiac failure are associated with a lower body mass index (Breit S. N. et al, *Growth factors* 2011; 29:187-195; Johnen H. et al, *Nat Med.* 2007; 13:1333-1340), suggesting that apart from any role in inflammation in disease, MIC-1/GDF15 may also play a role in body weight regulation. Long-term elevated expression of MIC-1/GDF15 in mice leads to decreased food intake, body weight and adiposity with concomitantly improved glucose tolerance, both under normal and obesogenic dietary conditions (Macia L. et al, *PloS One* 2012; 7(4):e34868). Food intake and body weight are controlled by a variety of central and peripheral factors, but the exact mechanisms behind these processes are still not fully understood.

There is a need for new therapeutic agents for the treatment of cachexia. There is a particular need for improved anti-GDF15 antibodies that are active and have improved therapeutic properties.

SUMMARY

Disclosed herein are antibodies (e.g., monoclonal antibodies) that bind to human Growth Differentiation Factor 15 protein (hereinafter, sometimes referred to as "GDF15"), with high affinity and specificity. The term "antibody" as used hereinafter to refer to the anti-GDF15 antibodies provided herein includes both a full length antibody and an antigen binding fragment thereof.

In some embodiments, the anti-GDF15 antibody is capable of binding to the C-terminal region of GDF15, e.g., the knuckle domain of GDF15. Without wishing to be bound by theory, it is believed that in certain embodiments, the specific binding to the C-terminal region of GDF15 (e.g., the knuckle domain) confers, at least in part, the biological functions and/or clinical effects of the anti-GDF15 antibody as described herein.

Nucleic acid molecules encoding the antibodies, expression vectors, host cells and methods for making the antibodies are also provided. Immunoconjugates, multi- or bispecific antibodies and pharmaceutical compositions comprising the antibodies are also provided. The anti-GDF15 antibodies disclosed herein can be used (alone or in combination with other agents or therapeutic modalities) to treat, prevent and/or diagnose GDF15-associated disorders or conditions, including those involving wasting disorders such as anorexia or cachexia. Thus, compositions and methods for detecting GDF15, as well as methods for treating various GDF15-associated disorders or conditions using the anti-GDF15 antibodies are disclosed.

Accordingly, in one aspect, provided herein is an antibody (e.g., an isolated or recombinant antibody or antigen binding fragment thereof) that binds to GDF15 (e.g., human GDF15) having one or more of the following properties or characteristics.

In some embodiments, the anti-GDF15 antibody, or antigen binding fragment, described herein, binds GDF15, with an equilibrium dissociation constant ($K_D$) of less than or equal to 150 nM. In some embodiments, the anti-GDF15 antibody, or antigen binding fragment, binds to human GDF15 or a fragment thereof, e.g., human GDF15 having the amino acid sequence of SEQ ID NO:1, or encoded by the nucleotide sequence of SEQ ID NO:2. For example, the antibody or antigen binding fragment described herein may bind to human GDF15 with a $K_D$ of less than or equal to 100 nM, less than or equal to 50 nM, less than or equal to 10 nM, less than or equal to 1 nM, less than or equal to 750 pM, less than or equal to 600 pM, less than or equal to 500 pM, less than or equal to 400 pM, less than or equal to 300 pM, less than or equal to 200 pM, less than or equal to 150 pM, less than or equal to 100 pM, less than or equal to 75 pM, less than or equal to 65 pM, less than or equal to 60 pM, less than or equal to 55 pM, less than or equal to 50 pM, less than or equal to 45 pM, less than or equal to 40 pM, less than or equal to 35 pM, less than or equal to 30 pM, less than or equal to 25 pM, less than or equal to 20 pM, less than or equal to 15 pM, less than or equal to 10 pM, less than or equal to 5 pM, less than or equal to 2 pM, less than or equal to 1 pM, less than or equal to 0.5 pM, less than or equal to 0.2 pM, or less than or equal to 0.1 pM.

In one embodiment, the antibody or antigen binding fragment, e.g., ABGDF15-A, binds human GDF15 with a $K_D$ of less than or equal to 11 pM, as measured by Biacore, or less than or equal to 1 pM, as measured by solution equilibrium titration assay (SET). In another embodiment, the antibody or antigen binding fragment, e.g., ABGDF15-B, binds human GDF15 with a $K_D$ of less than or equal to 115 pM, as measured by Biacore, or less than or equal to 120 pM, as measured by SET. In yet another embodiment, the antibody or antigen binding fragment, e.g., ABGDF15-C, binds human GDF15 with a $K_D$ of less than or equal to 66 pM, as measured by Biacore, or less than or equal to 120 pM, as measured by SET. In still another embodiment, the antibody or antigen binding fragment, e.g., ABGDF15-D, binds human GDF15 with a $K_D$ of less than or equal to 19 pM, as measured by Biacore, or less than or equal to 0.16 pM, as measured by SET. In still another embodiment, the antibody or antigen binding fragment, e.g., ABGDF15-E, binds human GDF15 with a $K_D$ of less than or equal to 39 pM, as measured by Biacore, or less than or equal to 2.3 pM, as measured by SET. In still another embodiment, the antibody or antigen binding fragment, e.g., ABGDF15-F, binds human GDF15 with a $K_D$ of less than or equal to 37 pM, as measured by Biacore, or less than or equal to 4.4 pM, as measured by SET. In still another embodiment, the antibody or antigen binding fragment, e.g., ABGDF15-G, binds human GDF15 with a $K_D$ of less than or equal to 20 pM, as measured by Biacore.

The antibodies or antigen binding fragment described herein can bind to human GDF15, cynomolgus GDF15, mouse GDF15, or rat GDF-15, with a $K_D$ described in Table 2, e.g., as determined by Biacore. In one embodiment, the antibody or antigen binding fragment binds human GDF15 (e.g., native human GDF15) with a $K_D$ of less than or equal to 120 pM, less than or equal to 100 pM, less than or equal to 80 pM, less than or equal to 60 pM, less than or equal to 40 pM, less than or equal to 20 pM, less than or equal to 15 pM, or less than or equal to 10 pM. In another embodiment, the antibody or antigen binding fragment binds human GDF (e.g., human His-GDF15) with a $K_D$ of less than or equal to 150 pM, less than or equal to 100 pM, less than or equal to 80 pM, less than or equal to 60 pM, less than or equal to 40 pM, less than or equal to 20 pM, less than or equal to 10 pM, less than or equal to 5 pM, or less than or equal to 2 pM. In another embodiment, the antibody or antigen binding fragment binds cynomolgus GDF (e.g., cyno His-GDF15) with a $K_D$ of less than or equal to 120 pM, less than or equal to 100 pM, less than or equal to 80 pM, less than or equal to 60 pM, less than or equal to 40 pM, less than or equal to 20 pM, or less than or equal to 10 pM. In another embodiment, the antibody or antigen binding fragment binds mouse GDF (e.g., mouse His-GDF15) with a $K_D$ of less than or equal to 250 pM, less than or equal to 200 pM, less than or equal to 150 pM, less than or equal to 100 pM, less than or equal to 80 pM, less than or equal to 60 pM, or less than or equal to 40 pM. In another embodiment, the antibody or antigen binding fragment binds mouse GDF (e.g., rat His-GDF15) with a $K_D$ of less than or equal to 150 pM, less than or equal to 100 pM, less than or equal to 80 pM, less than or equal to 60 pM, less than or equal to 40 pM, or less than or equal to 20 pM. In certain embodiments, the antibody or antigen binding fragment is cross reactive with one, two, three or all of human GDF15, cynomolgus GDF15, mouse GDF15, or rat GDF-15. For example, the antibodies or antigen binding fragments described herein can be cross reactive with both human GDF15 and cynomolgus GDF15.

In some embodiments, the anti-GDF15 antibody, or antigen binding fragment, described herein has an isoelectric point (pI) of between 8 and 10, e.g., between 8.2 and 9.8 between 8.4 and 9.6, between 8.6 and 9.4, between 8.8 and 9.2, between 8 and 8.5, between 8 and 9, between 8 and 9.5, between 8.5 and 10, between 9 and 10, or between 9.5 and 10. In one embodiment, the anti-GDF15 antibody (e.g., ABGDF15-A), or antigen binding fragment, has a pI of 8.7 (as an IgG) or 9.1 (as a Fab). In another embodiment, the anti-GDF15 antibody (e.g., ABGDF15-B), or antigen binding fragment, has a pI of 8.9 (as an IgG) or 9.3 (as a Fab). In another embodiment, the anti-GDF15 antibody (e.g., ABGDF15-C), or antigen binding fragment, has a pI of 8.3 (as an IgG) or 8.8 (as a Fab). In another embodiment, the anti-GDF15 antibody (e.g., ABGDF15-D), or antigen binding fragment, has a pI of 8.6 (as an IgG) or 9 (as a Fab). In another embodiment, the anti-GDF15 antibody (e.g., ABGDF15-E or ABGDF15-F), or antigen binding fragment, has a pI of 8.9 (as an IgG) or 9.2 (as a Fab). In another embodiment, the anti-GDF15 antibody (e.g., ABGDF15-G), or antigen binding fragment, has a pI of 9.3 (as an IgG) or 9.6 (as a Fab). In certain embodiments, the anti-GDF15 antibody, or antigen binding fragment, described herein has an isoelectric point (pI) as described in Table 4.

In some embodiments, the anti-GDF15 antibody, or antigen binding fragment, described herein shows the same or similar binding affinity or specificity, or both, as an antibody molecule (e.g., an heavy chain variable region and light chain variable region) described in Table 1, e.g., ABGDF15-A, ABGDF15-G, ABGDF15-B, ABGDF15-C, ABGDF15-F, ABGDF15-E, or ABGDF15-D. In embodiments, the anti-GDF15 antibody, or antigen binding fragment, described herein shows the same or similar binding affinity or specificity, or both, as an antibody molecule having an amino acid sequence shown in Table 1, or encoded by a nucleotide sequence shown in Table 1.

In some embodiments, the anti-GDF15 antibody, or antigen binding fragment, described herein competes for binding with an antibody as described in Table 1, e.g., ABGDF15-A, ABGDF15-G, ABGDF15-B, ABGDF15-C, ABGDF15-F, ABGDF15-E, or ABGDF15-D.

In embodiments, the anti-GDF15 antibody, or antigen binding fragment, described herein inhibits, e.g., competitively inhibits, the binding of a second antibody molecule to GDF15, wherein the second antibody is an antibody described in Table 1, e.g., an antibody chosen from, e.g., ABGDF15-A, ABGDF15-G, ABGDF15-B, ABGDF15-C, ABGDF15-F, ABGDF15-E, or ABGDF15-D.

In some embodiments, the anti-GDF15 antibody, or antigen binding fragment, described herein binds the same epitope, or substantially the same epitope (e.g., an overlapping epitope), as an antibody as described in Table 1, e.g., ABGDF15-A, ABGDF15-G, ABGDF15-B, ABGDF15-C, ABGDF15-F, ABGDF15-E, or ABGDF15-D. In some embodiments, the anti-GDF15 antibody, or antigen binding fragment, binds to one or more amino acids in the C-terminal region of GDF15, e.g., the knuckle domain of GDF15, e.g., human GDF15 (e.g., a knuckle region as described in Mueller, T. D. et al. FEBS Letters 586 (2012):1846-1859). In embodiments, the anti-GDF15 antibody, or antigen binding fragment, binds to one or more amino acids within amino acids 231 to 294 of SEQ ID NO:1. In one embodiment, the anti-GDF15 antibody, or antigen binding fragment, binds to one, two or all of amino acid 231, 285 or 294, of GDF15, e.g., human GDF15 (e.g., SEQ ID NO:1). In one embodiment, the anti-GDF15 antibody, or antigen binding fragment, binds to amino acids 285 and 294, and optionally 231, of GDF15, e.g., human GDF15 (e.g., SEQ ID NO:1). In one embodiment, the anti-GDF15 antibody, or antigen binding fragment, binds to amino acids 231 and 285, and optionally 294, of GDF15, e.g., human GDF15 (e.g., SEQ ID NO:1). In one embodiment, the anti-GDF15 antibody, or antigen binding fragment, binds to the same or substantially the same epitope as ABGDF15-A, ABGDF15-D, ABGDF15-E, ABGDF15-F, or ABGDF15-G, e.g., binds to an epitope that includes one or both of amino acid 285 or 294, of GDF15, e.g., human GDF15. In one embodiment, the anti-GDF15 antibody, or antigen binding fragment, binds to the same or substantially the same epitope as ABGDF15-A, ABGDF15-D, ABGDF15-E, ABGDF15-F, or ABGDF15-G, e.g., wherein the binding is blocked by a mutation at amino acid 285 and/or 294, of GDF15, e.g., human GDF15 (e.g., a mutation of I285R and/or L294R of SEQ ID NO:1). In one embodiment, the anti-GDF15 antibody, or antigen binding fragment, binds to the same or substantially the same epitope as ABGDF15-B, or ABGDF15-C, e.g., wherein the binding is blocked by a mutation at amino acid 231 and/or 285, of GDF15, e.g., human GDF15 (e.g., a mutation of S231R and/or I285R of SEQ ID NO:1).

The binding affinity and specificity of the antibodies and antigen binding fragments described herein can be determined by solution equilibrium titration (SET). Methods for SET are known in the art and are described in further detail below. Alternatively, binding affinity of the antibodies, or fragments, described herein can be determined by Biacore assay. Methods for Biacore kinetic assays are known in the art and are described in further detail below.

In some embodiments, the anti-GDF15 antibody, or antigen binding fragment, described herein has one or more biological properties of an antibody described in Table 1, e.g., an antibody chosen from ABGDF15-A, ABGDF15-G, ABGDF15-B, ABGDF15-C, ABGDF15-F, ABGDF15-E, or ABGDF15-D. Exemplary biological properties include one, two, three, four or more of: (i) inhibiting GDF15 binding to a receptor; (ii) reducing, e.g., depleting, the level of circulating GDF15; (iii) reducing, e.g., blocking, GDF-15-mediated suppression of food intake; (iv) reducing, e.g., blocking, GDF-15-mediated suppression of weight loss; or (v) reducing, e.g., reversing, GDF-15-mediated anorexia or cachexia. In specific embodiments, an anti-GDF15 antibody, or antigen binding fragment, described herein increases food intake. In particular embodiments, an anti-GDF15 antibody, or antigen binding fragment, described herein increases body weight.

In some embodiments, the anti-GDF15 antibody, or antigen binding fragment, described herein inhibits GDF15 binding to a receptor, for example, with an $EC_{50}$ of less than or equal to 100 nM, less than or equal to 50 nM, less than or equal to 35 nM, less than or equal to 25 nM, less than or equal to 10 nM, or less than or equal to 3 nM.

In some embodiments, the anti-GDF15 antibody, or antigen binding fragment, described herein reduces, e.g., depletes, the level of circulating GDF15.

In some embodiments, the anti-GDF15 antibody, or antigen binding fragment, described herein reduces, e.g., blocks, GDF-15-mediated suppression of food intake and/or weight loss in a subject, e.g., an animal model, e.g., as shown in FIGS. 1A-1B.

In some embodiments, the anti-GDF15 antibody, or antigen binding fragment, described herein reduces, e.g., reverses, GDF-15-mediated anorexia in a subject, e.g., an animal model, e.g., as shown in FIGS. 2A-3B.

In some embodiments, the anti-GDF15 antibody, or antigen binding fragment, described herein reduces, GDF-15-mediated weight loss in a subject, e.g., an animal model, e.g., as shown in FIGS. 4-5.

In some embodiments, the anti-GDF15 antibody, or antigen binding fragment, described herein binds to human GDF15 and is cross-reactive with cynomolgus GDF15.

The isolated anti-GDF15 antibodies, or antigen binding fragment thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes, e.g., as described herein.

Any of the antibodies or antigen binding fragments thereof provided herein may be a monoclonal antibody (e.g., monoclonal human antibody or monoclonal humanized antibody) or antigen binding fragments thereof. In other embodiments, the antibody or antigen binding fragment is a multispecific antibody, e.g., a bispecific antibody. The isolated anti-GDF15 antibodies, or antigen binding fragments thereof, as described herein can also include a framework in which an amino acid has been substituted into the antibody framework from the respective human VH or VL germline sequences.

In some embodiments, the anti-GDF15 antibody, or antigen binding fragment thereof, includes the full length heavy chain and/or the full length light chain of an antibody described in Table 1. In one embodiment, the antibody or antigen binding fragment thereof includes the heavy chain amino acid sequence and/or the light chain amino acid sequence of ABGDF15-A, ABGDF15-G, ABGDF15-B, ABGDF15-C, ABGDF15-F, ABGDF15-E, or ABGDF15-D, or an amino acid sequence substantially identical thereto (e.g., at least 80%, 85%, 90%, 92%, 95%, 97%, 98%, 99% or more identical thereto, or having at least 30, 20, 15, 10, 5 or fewer changes (e.g., substitutions, e.g., conservative substitutions, compared to) the heavy and/or light chain amino acid sequence of ABGDF15-A, ABGDF15-G, ABGDF15-B, ABGDF15-C, ABGDF15-F, ABGDF15-E, or ABGDF15-D). In another embodiment, the antibody or antigen binding fragment thereof is encoded by the heavy chain nucleotide sequence and/or the light chain nucleotide sequence of ABGDF15-A, ABGDF15-G, ABGDF15-B, ABGDF15-C, ABGDF15-F, ABGDF15-E, or ABGDF15-D, or a nucleotide sequence substantially identical thereto (e.g., at least 80%, 85%, 90%, 92%, 95%, 97%, 98%, 99% or more identical thereto, or having at least 90, 60, 45, 30, 15 or fewer changes (e.g., substitutions), compared to) the heavy and/or light chain nucleotide sequence of ABGDF15-A, ABGDF15-G, ABGDF15-B, ABGDF15-C, ABGDF15-F, ABGDF15-E, or ABGDF15-D). In embodiments, any of the aforesaid sequences includes one, two, or three complementarity determining regions (CDRs) from the heavy chain, and/or one, two, or three CDRs from the light chain, of ABGDF15-A, ABGDF15-G, ABGDF15-B, ABGDF15-C, ABGDF15-F, ABGDF15-E, or ABGDF15-D.

In some embodiments, the anti-GDF15 antibody, or antigen binding fragment thereof, includes one or two of the heavy chain variable domain and/or one or two light chain variable domain of an antibody described in Table 1. In one embodiment, the antibody or antigen binding fragment thereof includes one or two of the heavy chain variable domain amino acid sequence and/or one or two of the light chain variable domain amino acid sequence of ABGDF15-A, ABGDF15-G, ABGDF15-B, ABGDF15-C, ABGDF15-F, ABGDF15-E, or ABGDF15-D, or an amino acid sequence substantially identical thereto (e.g., at least 80%, 85%, 90%, 92%, 95%, 97%, 98%, 99% or more identical thereto, or having at least 20, 15, 10, 5 or fewer changes (e.g., substitutions, e.g., conservative substitutions, compared to) the heavy and/or light chain variable domain amino acid sequence of ABGDF15-A, ABGDF15-G, ABGDF15-B, ABGDF15-C, ABGDF15-F, ABGDF15-E, or ABGDF15-D). In another embodiment, the antibody or antigen binding fragment thereof is encoded by the heavy chain variable domain nucleotide sequence, and/or the light chain variable domain nucleotide sequence, of ABGDF15-A, ABGDF15-G, ABGDF15-B, ABGDF15-C, ABGDF15-F, ABGDF15-E, or ABGDF15-D, or a nucleotide sequence substantially identical thereto (e.g., at least 80%, 85%, 90%, 92%, 95%, 97%, 98%, 99% or more identical thereto, or having at least 60, 45, 30, 15 or fewer changes (e.g., substitutions), compared to) the heavy chain variable domain, and/or light chain variable domain, nucleotide sequence of ABGDF15-A, ABGDF15-G, ABGDF15-B, ABGDF15-C, ABGDF15-F, ABGDF15-E, or ABGDF15-D). In embodiments, any of the aforesaid sequences includes one, two, or three CDRs from the heavy chain variable domain, and/or one, two, or three CDRs from the light chain variable domain, of ABGDF15-A, ABGDF15-G, ABGDF15-B, ABGDF15-C, ABGDF15-F, ABGDF15-E, or ABGDF15-D.

In another embodiment, the anti-GDF15 antibody, or antigen binding fragment thereof, includes at least one antigen-binding region, e.g., a variable region or an antigen-binding fragment thereof, from an antibody described in Table 1, e.g., an antibody chosen from any of ABGDF15-A, ABGDF15-G, ABGDF15-B, ABGDF15-C, ABGDF15-F, ABGDF15-E, or ABGDF15-D; or encoded by the nucleotide sequence in Table 1; or a sequence substantially identical (e.g., at least 80%, 85%, 90%, 92%, 95%, 97%, 98%, 99% or higher identical) to any of the aforesaid sequences. In some embodiments, any of the aforesaid sequences includes one, two, or three CDRs from the heavy chain variable domain, and/or one, two, or three CDRs from the light chain chain variable domain, of ABGDF15-A, ABGDF15-G, ABGDF15-B, ABGDF15-C, ABGDF15-F, ABGDF15-E, or ABGDF15-D.

In yet another embodiment, the anti-GDF15 antibody, or antigen binding fragment thereof, includes at least one, two, or three CDRs from a heavy chain variable region, and/or at least one, two, or three CDRs from a light chain variable region of an antibody described in Table 1, e.g., an antibody chosen from any of ABGDF15-A, ABGDF15-G, ABGDF15-B, ABGDF15-C, ABGDF15-F, ABGDF15-E, or ABGDF15-D; or encoded by the nucleotide sequence in Table 1; or a sequence substantially identical (e.g., at least 80%, 85%, 90%, 92%, 95%, 97%, 98%, 99% or higher identical) to any of the aforesaid sequences. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In one embodiment, one, two, three, four, five or more of the CDRs (or collectively all of the CDRs) of the anti-GDF15 antibody, or antigen binding fragment thereof, is/are according to Kabat et al. (e.g., at least one, two, or three CDRs according to the Kabat definition as set out in Table 1). In other embodiments, one, two, three, four, five or more of the CDRs (or collectively all of the CDRs) of the anti-GDF15 antibody, or antigen binding fragment thereof, is/are according to Chothia et al. (e.g., at least one, two, or three CDRs according to the Chothia definition as set out in Table 1). In yet another embodiment, one, two, three, four, five or more of the CDRs (or collectively all of the CDRs) of the anti-GDF15 antibody, or antigen binding fragment thereof, is/are according to Kabat and Chothia combined definition as set out in Table 1.

In some embodiments, the anti-GDF15 antibody, or antigen binding fragment thereof, includes a heavy chain CDR1 chosen from SEQ ID NOs: 3, 29, 55, 81, 107, 133, or 159; a heavy chain CDR2 chosen from SEQ ID NOs: 4, 30, 56, 82, 108, 134, or 160; and/or a heavy chain CDR3 chosen from SEQ ID NOs: 5, 31, 57, 83, 109, 135, or 161 (according to the combined Kabat and Chothia CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes a heavy chain CDR1 chosen from SEQ ID NOs: 6, 32, 58, 84, 110, 136, or 162; a heavy chain CDR2 chosen from SEQ ID NOs: 7, 33, 59, 85, 111, 137, or 163; and/or a heavy chain CDR3 chosen from SEQ ID NOs: 8, 34, 60, 86, 112, 138, or 164 (according to the Kabat CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes a heavy chain CDR1 chosen from SEQ ID NOs: 9, 35, 61, 87, 113, 139, or 165; a heavy chain CDR2 chosen from SEQ ID NOs: 10, 36, 62, 88, 114, 140, or 166; and/or a heavy chain CDR3 chosen from SEQ ID NOs: 11, 37, 63, 89, 115, 141, or 167 (according to the Chothia CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes a light chain CDR1 chosen from SEQ ID NOs: 16, 42, 68, 94, 120, 146, or 172; a light chain CDR2 chosen from SEQ ID NOs: 17, 43, 69, 95, 121, 147, or 173; and/or a light chain CDR3 chosen from SEQ ID NOs: 18, 44, 70, 96, 122, 148, or 174 (according to the combined Kabat and Chothia CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes a light chain CDR1 chosen from SEQ ID NOs: 19, 45, 71, 97, 123, 149, or 175; a light chain CDR2 chosen from SEQ ID NOs: 20, 46, 72, 98, 124, 150, or 176; and/or a light chain CDR3 chosen from SEQ ID NOs: 21, 47, 73, 99, 125, 151, or 177 (according to the Kabat CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes a light chain CDR1 chosen from SEQ ID NOs: 22, 48, 74, 100, 126, 152, or 178; a light chain CDR2 chosen from SEQ ID NOs: 23, 49, 75, 101, 127, 153, or 179; and a light chain CDR3 chosen from SEQ ID NOs: 24, 50, 76, 102, 128, 154, or 180 (according to the Chothia CDR definition). In one embodiment, one or more of the CDRs (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes:
(i) a heavy chain CDR1 chosen from SEQ ID NOs: 3, 29, 55, 81, 107, 133, or 159; a heavy chain CDR2 chosen from SEQ ID NOs: 4, 30, 56, 82, 108, 134, or 160; and a heavy chain CDR3 chosen from SEQ ID NOs: 5, 31, 57, 83, 109, 135, or 161; and
(ii) a light chain CDR1 chosen from SEQ ID NOs: 16, 42, 68, 94, 120, 146, or 172; a light chain CDR2 chosen from SEQ ID NOs: 17, 43, 69, 95, 121, 147, or 173; and a light chain CDR3 chosen from SEQ ID NOs: 18, 44, 70, 96, 122, 148, or 174 (according to the combined Kabat and Chothia CDR definition).

In one embodiment, one or more of the CDRs in (i) and/or (ii) (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes:
(i) a heavy chain CDR1 chosen from SEQ ID NOs: 6, 32, 58, 84, 110, 136, 162; a heavy chain CDR2 chosen from SEQ ID NOs: 7, 33, 59, 85, 111, 137, or 163; and a heavy chain CDR3 chosen from SEQ ID NOs: 8, 34, 60, 86, 112, 138, or 164; and
(ii) a light chain CDR1 chosen from SEQ ID NOs: 19, 45, 71, 97, 123, 149, 175; a light chain CDR2 chosen from SEQ ID NOs: 20, 46, 72, 98, 124, 150, 176; and a light chain CDR3 chosen from SEQ ID NOs: 21, 47, 73, 99, 125, 151, 177 (according to the Kabat CDR definition).

In one embodiment, one or more of the CDRs in (i) and/or (ii) (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes:
(i) a heavy chain CDR1 chosen from SEQ ID NOs: 9, 35, 61, 87, 113, 139, or 165; a heavy chain CDR2 chosen from SEQ ID NOs: 10, 36, 62, 88, 114, 140, or 166; and a heavy chain CDR3 chosen from SEQ ID NOs: 11, 37, 63, 89, 115, 141, or 167; and
(ii) a light chain CDR1 chosen from SEQ ID NOs: 22, 48, 74, 100, 126, 152, or 178; a light chain CDR2 chosen from SEQ ID NOs: 23, 49, 75, 101, 127, 153, or 179; and a light chain CDR3 chosen from SEQ ID NOs: 24, 50, 76, 102, 128, 154, or 180 (according to the Chothia CDR definition).

In one embodiment, one or more of the CDRs in (i) and/or (ii) (or collectively all of the CDRs) have one, two, three, four, five, six or more changes, e.g., amino acid substitutions or deletions, relative to any of the aforesaid amino acid sequence.

In some embodiments, the anti-GDF15 antibody, or antigen binding fragment thereof, includes: one, two, three, four, five or all of:
a heavy chain variable region CDR1 (HCDR1) comprising an amino acid sequence of G-X2-X3-F-X5-X6-X7-X8-X9-X10 (SEQ ID NO: 188), wherein X2 is Y or G; X3 is S or T; X5 is R, T or S; X6 is S or D; X7 is Y or H; X8 is A, W or Y; X9 is V or I; and X10 is S, G or N, a heavy chain variable region CDR2 (HCDR2) comprising an amino acid sequence of X1-I-X3-P-X5-X6-X7-X8-X9-X10-Y-X12-X13-X14-F-Q-G (SEQ ID NO: 189), wherein X1 is G, I or V; X3 is I or D; X5 is I, S, G, A or D; X6 is F or G; X7 is G or S; X8 is T, Y or G; X9 is A or T; X10 is N or I; X12 is A or S; X13 is Q or P; and X14 is K or S, a heavy chain variable region CDR3 (HCDR3) comprising an amino acid sequence of X1-X2-X3-X4-X5-X6-X7-X8-X9-X10-X11-X12-X13-X14-X15-D-X17 (SEQ ID NO: 190), wherein X1 is G, V, Y or F; X2 is P, S or G; X3 is I, Y, R or S; X4 is I, Y or V; X5 is M, G or Y; X6 is G, T or V; X7 is Y or S; X8 is Q, F or R; X9 is F, Y or absent; X10 is G, S or absent; X11 is L, S or absent; X12 is F, Y or absent; X13 is Y or absent; X14 is H or absent; X15 is M is absent; and X17 is H, I, Y or V, a light chain variable region CDR1 (LCDR1) comprising an amino acid sequence of X1-X2-X3-X4-X5-X6-X7-X8-X9-X10-X11-X12-X13 (SEQ ID NO: 191), wherein X1 is S or R; X2 is G or A; X3 is D or S; X4 is N, Q or S; X5 is I, S or T; X6 is G, I or N; X7 is S, I or Y; X8 is G or absent; X9 is V or absent; X10 is H, N, L or R; X11 is I, N, Y or S; X12 is V or L; and X13 is S, N or A, a light chain variable region CDR2 (LCDR2) comprising an amino acid sequence of X1-X2-X3-X4-X5-X6-S(SEQ ID NO: 192), wherein X1 is D, A, S or G; X2 is K, A or N; X3 is S or D; X4 is N or I; X5 is R or L; and X6 is P or Q, or a light chain variable region CDR3 (LCDR3) comprising an amino acid sequence of X1-X2-X3-X4-X5-X6-X7-X8-X9-X10 (SEQ ID NO: 193), wherein X1 is Q, F or L; X2 is T, Q or S; X3 is W, L or R; X4 is D or Y; X5 is S, H or T; X6 is I or S; X7 is G, P or S; X8 is S, N or absent; X9 is V, F or Y; X10 is V or T.

In some embodiments, the anti-GDF15 antibody, or antigen binding fragment thereof, includes HCDR1, HCDR2, and HCDR3 and LCDR1, LCDR2, and LCDR3, wherein:

(i) HCDR1, HCDR2, and HCDR3 comprises SEQ ID NOs: 3, 4, and 5, and LCDR1, LCDR2, LCDR3 comprises SEQ ID NOs: 16, 17, and 18; or (ii) HCDR1, HCDR2, and HCDR3 comprises SEQ ID NOs: 29, 30, and 31, and LCDR1, LCDR2, LCDR3 comprises SEQ ID NOs: 42, 43, and 44; or (iii) HCDR1, HCDR2, and HCDR3 comprises SEQ ID NOs: 55, 56, and 57, and LCDR1, LCDR2, LCDR3 comprises SEQ ID NOs: 68, 69, and 70; or (iv) HCDR1, HCDR2, and HCDR3 comprises SEQ ID NOs: 81, 82, and 83, and LCDR1, LCDR2, LCDR3 comprises SEQ ID NOs: 94, 95, and 96; or (v) HCDR1, HCDR2, and HCDR3 comprises SEQ ID NOs: 107, 108, and 109, and LCDR1, LCDR2, LCDR3 comprises SEQ ID NOs: 120, 121, and 122; or (vi) HCDR1, HCDR2, and HCDR3 comprises SEQ ID NOs: 133, 134, and 135, and LCDR1, LCDR2, LCDR3 comprises SEQ ID NOs: 146, 147, and 148; or (vii) HCDR1, HCDR2, and HCDR3 comprises SEQ ID NOs: 159, 160, and 161, and LCDR1, LCDR2, LCDR3 comprises SEQ ID NOs: 172, 173, and 174.

In some embodiments, the anti-GDF15 antibody, or antigen binding fragment thereof, includes HCDR1, HCDR2, and HCDR3 and LCDR1, LCDR2, and LCDR3, wherein:

(i) HCDR1, HCDR2, and HCDR3 comprises SEQ ID NOs: 6, 7, and 8, and LCDR1, LCDR2, LCDR3 comprises SEQ ID NOs: 19, 20, and 21; or (ii) HCDR1, HCDR2, and HCDR3 comprises SEQ ID NOs: 32, 33, and 34, and LCDR1, LCDR2, LCDR3 comprises SEQ ID NOs: 45, 46, and 47; or (iii) HCDR1, HCDR2, and HCDR3 comprises SEQ ID NOs: 58, 59, and 60, and LCDR1, LCDR2, LCDR3 comprises SEQ ID NOs: 71, 72, and 73; or (iv) HCDR1, HCDR2, and HCDR3 comprises SEQ ID NOs: 84, 85, and 86, and LCDR1, LCDR2, LCDR3 comprises SEQ ID NOs: 97, 98, and 99; or (v) HCDR1, HCDR2, and HCDR3 comprises SEQ ID NOs: 110, 111, and 112, and LCDR1, LCDR2, LCDR3 comprises SEQ ID NOs: 123, 124, and 125; or (vi) HCDR1, HCDR2, and HCDR3 comprises SEQ ID NOs: 136, 137, and 138, and LCDR1, LCDR2, LCDR3 comprises SEQ ID NOs: 149, 150, and 151; or (vii) HCDR1, HCDR2, and HCDR3 comprises SEQ ID NOs: 162, 163, and 164, and LCDR1, LCDR2, LCDR3 comprises SEQ ID NOs: 175, 176, and 177.

In some embodiments, the anti-GDF15 antibody, or antigen binding fragment thereof, includes HCDR1, HCDR2, and HCDR3 and LCDR1, LCDR2, and LCDR3, wherein:

(i) HCDR1, HCDR2, and HCDR3 comprises SEQ ID NOs: 9, 10, and 11, and LCDR1, LCDR2, LCDR3 comprises SEQ ID NOs: 22, 23, and 24; or (ii) HCDR1, HCDR2, and HCDR3 comprises SEQ ID NOs: 35, 36, and 37, and LCDR1, LCDR2, LCDR3 comprises SEQ ID NOs: 48, 49, and 50; or (iii) HCDR1, HCDR2, and HCDR3 comprises SEQ ID NOs: 61, 62, and 63, and LCDR1, LCDR2, LCDR3 comprises SEQ ID NOs: 74, 75, and 76; or (iv) HCDR1, HCDR2, and HCDR3 comprises SEQ ID NOs: 87, 88, and 89, and LCDR1, LCDR2, LCDR3 comprises SEQ ID NOs: 100, 101, and 102; or (v) HCDR1, HCDR2, and HCDR3 comprises SEQ ID NOs: 113, 114, and 115, and LCDR1, LCDR2, LCDR3 comprises SEQ ID NOs: 126, 127, and 128; or (vi) HCDR1, HCDR2, and HCDR3 comprises SEQ ID NOs: 139, 140, and 141, and LCDR1, LCDR2, LCDR3 comprises SEQ ID NOs: 152, 153, and 154; or (vii) HCDR1, HCDR2, and HCDR3 comprises SEQ ID NOs: 165, 166, and 167, and LCDR1, LCDR2, LCDR3 comprises SEQ ID NOs: 178, 179, and 180.

In some embodiments, the anti-GDF15 antibody, or antigen binding fragment thereof, includes the HCDR1, HCDR2, and HCDR3 of the variable heavy chain of SEQ ID NOs: 12, 38, 64, 90, 116, 142, or 168, and the LCDR1, LCDR2 and LCDR3 of the variable light chain of SEQ ID NOs: 25, 51, 77, 103, 129, 155, or 181. In some embodiments, the anti-GDF15 antibody, or antigen binding fragment thereof, includes the HCDR1, HCDR2, and HCDR3 of the variable heavy chain of SEQ ID NO: 12, and the LCDR1, LCDR2 and LCDR3 of the variable light chain of SEQ ID NO: 25. In some embodiments, the anti-GDF15 antibody, or antigen binding fragment thereof, includes the HCDR1, HCDR2, and HCDR3 of the variable heavy chain of SEQ ID NO: 38, and the LCDR1, LCDR2 and LCDR3 of the variable light chain of SEQ ID NOs: 51. In some embodiments, the anti-GDF15 antibody, or antigen binding fragment thereof, includes the HCDR1, HCDR2, and HCDR3 of the variable heavy chain of SEQ ID NO: 64, and the LCDR1, LCDR2 and LCDR3 of the variable light chain of SEQ ID NO: 77. In some embodiments, the anti-GDF15 antibody, or antigen binding fragment thereof, includes the HCDR1, HCDR2, and HCDR3 of the variable heavy chain of SEQ ID NO: 90, and the LCDR1, LCDR2 and LCDR3 of the variable light chain of SEQ ID NO: 103. In some embodiments, the anti-GDF15 antibody, or antigen binding fragment thereof, includes the HCDR1, HCDR2, and HCDR3 of the variable heavy chain of SEQ ID NO: 116, and the LCDR1, LCDR2 and LCDR3 of the variable light chain of SEQ ID NO: 129. In some embodiments, the anti-GDF15 antibody, or antigen binding fragment thereof, includes the HCDR1, HCDR2, and HCDR3 of the variable heavy chain of SEQ ID NO: 142, and the LCDR1, LCDR2 and LCDR3 of the variable light chain of SEQ ID NO: 155. In some embodiments, the anti-GDF15 antibody, or antigen binding fragment thereof, includes the HCDR1, HCDR2, and HCDR3 of the variable heavy chain of SEQ ID NO: 168, and the LCDR1, LCDR2 and LCDR3 of the variable light chain of SEQ ID NO: 181.

In some embodiments, the anti-GDF15 antibody, or antigen binding fragment thereof, includes the HCDR1, HCDR2, and HCDR3 of the variable heavy chain of SEQ ID NOs: 12, 38, 64, 90, 116, 142, or 168, and the LCDR1, LCDR2 and LCDR3 of the variable light chain of SEQ ID NOs: 25, 51, 77, 103, 129, 155, or 181, as defined by Chothia.

In some embodiments, the anti-GDF15 antibody, or antigen binding fragment thereof, includes the HCDR1, HCDR2, and HCDR3 of the heavy chain variable domain sequence of SEQ ID NOs: 12, 38, 64, 90, 116, 142, or 168, and the LCDR1, LCDR2 and LCDR3 of the light chain variable domain sequence of SEQ ID NOs: 25, 51, 77, 103, 129, 155, 181, as defined by Kabat.

In still other embodiments, the antibody or antigen binding fragment includes the HCDR1, HCDR2, and HCDR3 of the heavy chain variable domain sequence of SEQ ID NOs: 12, 38, 64, 90, 116, 142, 168, and the LCDR1, LCDR2 and LCDR3 of the light chain variable domain sequence of SEQ ID NOs: 25, 51, 77, 103, 129, 155, 181, as defined by Kabat and Chothia combined.

In still other embodiments, the antibody or antigen binding fragment includes a heavy chain variable domain sequence chosen from SEQ ID NOs: 12, 38, 64, 90, 116, 142, or 168. The isolated antibody or antigen binding fragment further can comprise a light chain variable domain sequence wherein the heavy chain variable domain and light chain variable domain combine to form and antigen binding site for GDF15. In one embodiment, the light chain variable domain sequence is chosen from SEQ ID NOs: 25, 51, 77, 103, 129, 155, or 181, wherein said isolated antibody or antigen binding fragments thereof binds GDF15.

In still other embodiments, the antibody or antigen binding fragment includes a light chain variable domain sequence chosen from SEQ ID NOs: 25, 51, 77, 103, 129, 155, or 181, wherein said antibody or antigen binding fragments thereof binds to human GDF15. The antibody or antigen binding fragment may further comprise a heavy chain variable domain sequence wherein the light chain variable domain and heavy chain variable domain combine to form and antigen binding site for GDF15.

In some embodiments, the antibody or antigen binding fragment thereof that binds GDF15, includes a heavy and light chain variable domains comprising the sequences of SEQ ID NOs: 12 and 25; 38 and 51; 64 and 77; 90 and 103; 116 and 129; 142 and 155; or 168 and 181, respectively.

In other embodiments, the antibody or antigen binding fragment thereof, that includes a heavy chain variable domain having at least 90% sequence identity to a sequence chosen from SEQ ID NOs: 12, 38, 64, 90, 116, 142, or 168, wherein said antibody binds to GDF15. In one aspect, the isolated antibody or antigen binding fragments thereof also includes a light chain variable domain having at least 90% sequence identity to a sequence chosen from SEQ ID NOs: 25, 51, 77, 103, 129, 155, or 181. In embodiments, the antibody or antigen binding fragment has an HCDR1, HCDR2, HCDR3, LCDR1, LCDR2 and LCDR3 as defined by Kabat and as described in Table 1.

In other embodiments, the antibody or antigen binding fragment thereof, that includes a light chain variable domain having at least 90% sequence identity to a sequence selected from the group consisting of SEQ ID NOs: 25, 51, 77, 103, 129, 155, or 181, wherein said antibody binds GDF15.

In another embodiment, the isolated antibody, or antigen binding fragments thereof, that binds to GDF15 may have a heavy chain comprising the sequence of SEQ ID NOs: 14, 40, 66, 92, 118, 144, or 170. The isolated antibody can also include a light chain that can combine with the heavy chain to form an antigen binding site to human GDF15. In particular, the light chain may have a sequence comprising SEQ ID NOs: 27, 53, 79, 105, 131, 157, or 183. In particular, the isolated antibody or antigen binding fragments thereof that binds GDF15, may have a heavy chain and a light chain comprising the sequences of SEQ ID NOs: 14 and 27; 40 and 53; 66 and 79; 92 and 105; 118 and 131; 144 and 157; or 170 and 183, respectively.

Other embodiments provided herein include an isolated antibody or antigen binding fragments thereof that includes a heavy chain having at least 90% sequence identity to a sequence selected from the group consisting of SEQ ID NOs: 14, 40, 66, 92, 118, 144, 170, wherein said antibody binds to GDF15. In one aspect, the isolated antibody or antigen binding fragments thereof also includes a light chain having at least 90% sequence identity to a sequence selected from the group consisting of SEQ ID NOs: 27, 53, 79, 105, 131, 157, 183.

In other embodiments, the antibody or antigen binding fragments thereof includes a light chain having at least 90% sequence identity to a sequence selected from the group consisting of SEQ ID NOs: 27, 53, 79, 105, 131, 157, 183, wherein said antibody binds GDF15.

In another aspect, provided herein is a composition comprising the isolated antibody, or antigen binding fragments thereof, described herein. As well as, antibody compositions in combination with a pharmaceutically acceptable carrier. Specifically, provided herein are pharmaceutical compositions comprising an antibody or antigen binding fragments thereof of Table 1, such as, for example antibody ABGDF15-A, ABGDF15-G, ABGDF15-B, ABGDF15-C, ABGDF15-F, ABGDF15-E, or ABGDF15-D. Also provided herein are pharmaceutical compositions comprising a combination of two or more of the isolated antibodies or antigen binding fragments thereof of Table 1.

In another aspect, provided herein is a nucleic acid molecule that comprises one or both nucleotide sequences that encode heavy and light chains, heavy and light chain variable regions, heavy and light chain CDRs, of the anti-GDF15 antibodies, as described herein. In certain embodiments, the nucleotide sequence that encodes the anti-GDF15 antibody is codon optimized. In one embodiment, provided herein is a first and second nucleic acid encoding heavy and light chain variable regions, respectively, of an anti-GDF15 antibody chosen from one or more of, e.g., any of ABGDF15-A, ABGDF15-G, ABGDF15-B, ABGDF15-C, ABGDF15-F, ABGDF15-E, or ABGDF15-D, as summarized in Table 1, or a sequence substantially identical thereto. For example, the nucleic acid can comprise a nucleotide sequence as set forth in Table 1, or a sequence substantially identical thereto (e.g., a sequence at least about 85%, 90%, 95%, 99% or more identical thereto, or which differs by no more than 3, 6, 15, 30, or 45 nucleotides from the sequences shown in Table 1).

In other embodiments, the nucleic acid molecule comprises a nucleotide sequence that encodes a heavy chain variable domain and/or a heavy chain constant region comprising the amino acid sequence of ABGDF15-A, ABGDF15-G, ABGDF15-B, ABGDF15-C, ABGDF15-F, ABGDF15-E, or ABGDF15-D; or as described in Table 1; or the nucleotide sequence in Table 1; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of ABGDF15-A, ABGDF15-G, ABGDF15-B, ABGDF15-C, ABGDF15-F, ABGDF15-E, or ABGDF15-D; or as described in Table 1; or the nucleotide sequence in Table 1; or a sequence substantially identical (e.g., a sequence at least about 85%, 90%, 95%, 99% or more identical) to any of the aforesaid sequences.

The aforesaid nucleotide sequences encoding the anti-GDF15 heavy and light chain variable domain and constant regions can be present in a separate nucleic acid molecule, or in the same nucleic acid molecule. In certain embodiments, the nucleic acid molecules comprise a nucleotide sequence encoding a leader sequence.

In certain embodiments, the nucleic acid molecule comprises a nucleotide sequence encoding at least one, two, or three CDRs, from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions).

In other embodiments, provided herein is an isolated nucleic acid sequence encoding the heavy chain variable region having a sequence chosen from SEQ ID NOs: 12, 38, 64, 90, 116, 142, or 168. In embodiments, the nucleic acid includes a nucleotide sequence at least 90% sequence identity to a sequence chosen from SEQ ID NOs: 13, 39, 65, 91, 117, 143, or 169. In certain embodiments, the sequence includes the nucleotide of SEQ ID NOs: 13, 39, 65, 91, 117, 143, or 169.

In embodiments, the isolated nucleic acid sequence encoding the light chain variable region includes a sequence chosen from SEQ ID NOs: 25, 51, 77, 103, 129, 155, or 182. In particular the nucleic acid includes a nucleotide sequence at least 90% sequence identity to a sequence chosen from SEQ ID NOs: 26, 52, 78, 104, 130, 156, or 183. In certain embodiments, the sequence is SEQ ID NOs: 26, 52, 78, 104, 130, 156, or 183.

In other embodiments, the isolated nucleic acid encoding the heavy chain has the amino acid sequence chosen from SEQ ID NOs: 14, 40, 66, 92, 118, 144, or 170, or a nucleotide sequence substantially identical, e.g., at least 90% identical, thereto. In other embodiments, the isolated nucleic acid encoding the heavy chain has the nucleotide sequence chosen from SEQ ID NOs: 15, 41, 67, 93, 119, 145, or 171, or a nucleotide sequence substantially identical, e.g., at least 90% identical, thereto.

In other embodiments, the isolated nucleic acid encoding the light chain has the amino acid sequence chosen from SEQ ID NOs: 27, 53, 79, 105, 131, 157, or 183, or a nucleotide sequence substantially identical, e.g., at least 90% identical, thereto. In other embodiments, the isolated nucleic acid encoding the light chain has the nucleotide sequence chosen from SEQ ID NOs: 28, 54, 80, 106, 132, 158, or 184, or a nucleotide sequence substantially identical, e.g., at least 90% identical, thereto.

Provided herein is an isolated nucleic acid comprising a nucleotide sequence encoding a polypeptide that includes a light chain variable domain having at least 90% sequence identity to a sequence chosen from SEQ ID NOs: 28, 54, 80, 106, 132, 158, or 184.

Also provided herein is a vector that includes one or more of the nucleic acid molecules described herein. The heavy and light chain regions may be present in the same vector or separate vectors.

Also provided herein is an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell. The antibody can be a human antibody. The host cell can be a non-human mammalian cell.

In embodiments, the cell is a human cell. The cell can be in a subject. In one embodiment, the cell is an endothelial cell. In other embodiments, the cell may be one or more of adipose, muscle, and liver cells. In embodiments, the subject is a human.

In another aspect, a method of providing an antibody described herein is disclosed. The method includes: providing a GDF15 antigen (e.g., an antigen comprising at least a portion of a GDF15 epitope); obtaining an antibody molecule that specifically binds to the GDF15 polypeptide; and evaluating if the antibody molecule specifically binds to the GDF15 polypeptide, or evaluating efficacy of the antibody molecule in modulating, e.g., inhibiting, the activity of the GDF15. The method can further include administering the antibody molecule to a subject, e.g., a human or non-human animal.

In another aspect, provided herein is a method of treating, improving, or preventing a GDF15-associated disorder in a subject, e.g., a patient. The method includes administering to the subject an effective amount of a composition comprising the antibody or antigen binding fragments thereof described herein. In one embodiment, the GDF15-associated disorder is associated with wasting disorders such as anorexia cachexia, anorexia of the aged, anorexia nervosa, cachexia associated with cancer, cachexia associated with AIDS, cachexia associated with heart failure, cachexia associated with cystic fibrosis, cachexia associated with rheumatoid arthritis, cachexia associated with kidney disease, cachexia associated with COPD, cachexia associated with ALS, cachexia associated with renal failure or cachexia associated with hip fracture, and the like. In other embodiments, the GDF15-associated disorder is associated with sarcopenia, starvation, and disorders associated with aberrant appetite, fat mass, energy balance, and/or involuntary weight loss, and reduced mortality and morbidity of critically ill patients.

In one aspect, provided herein is a method of increasing appetite and/or food intake in a subject, e.g., a subject in need thereof. The method includes administering to the subject an effective amount of an anti-GDF15 antibody or fragment thereof as described herein.

In another aspect, provided herein is a method of increasing body weight in a subject, e.g., a subject in need thereof. The method includes administering to the subject an effective amount of an anti-GDF15 antibody or fragment thereof as described herein.

In another aspect, provided herein is a method of inhibiting or reducing one or more of: loss of body weight, muscle mass, appetite, or food intake, in a subject e.g., a subject in need thereof. The method includes administering to the subject an effective amount of an anti-GDF15 antibody or fragment thereof as described herein.

In some embodiments, the subject is a mammal, e.g., a human. In one embodiment, the subject has a wasting disorder, e.g., cachexia or sarcopenia, or both. In other embodiments, the subject has cancer, chronic heart failure, chronic kidney disease, COPD, AIDS, multiple sclerosis, rheumatoid arthritis, sepsis, or tuberculosis. The anti-GDF15 antibody or fragment thereof can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes.

In one aspect, provided herein is an anti-GDF15 antibody or fragment thereof described herein for use as a medicament.

In another aspect, provided herein is an anti-GDF15 antibody or fragment thereof described herein for use in the treatment, improvement or prevention of a GDF15-associated disorder (e.g., a GDF15-associated disorder described herein, e.g., a wasting disorder, e.g., cachexia or sarcopenia, cancer, chronic heart failure, chronic kidney disease, COPD, AIDS, multiple sclerosis, rheumatoid arthritis, sepsis, or tuberculosis) in a subject, e.g., a subject described herein.

In one aspect, provided herein is an anti-GDF15 antibody or fragment thereof described herein for use in increasing appetite and/or food intake in a subject, e.g., a subject described herein.

In another aspect, provided herein is an anti-GDF15 antibody or fragment thereof described herein for use in increasing body weight in a subject, e.g., a subject described herein.

In another embodiment, provided herein is an anti-GDF15 antibody or fragment thereof in inhibiting or reducing one or more of: loss of body weight, muscle mass, appetite, or food intake, in a subject, e.g., a subject described herein.

In an embodiment, an anti-GDF15 antibody or fragment thereof, for use in the treatment of a wasting disorder, e.g., cachexia or sarcopenia, cancer, chronic heart failure, chronic kidney disease, COPD, AIDS, multiple sclerosis, rheumatoid arthritis, sepsis, or tuberculosis is provided.

In another aspect, provided herein is use an anti-GDF15 antibody or fragment thereof described herein in the manufacture of a medicament for treating, improving, or preventing a GDF15-associated disorder (e.g., a GDF15-associated disorder described herein) in a subject, e.g., a subject described herein.

In one aspect, provided herein is use of an anti-GDF15 antibody or fragment thereof described herein in the manufacture of a medicament for increasing appetite and/or food intake in a subject, e.g., a subject described herein.

In another aspect, provided herein is use of an anti-GDF15 antibody or fragment thereof described herein in the manufacture of a medicament for increasing body weight in a subject, e.g., a subject described herein.

In another embodiment, provided herein is use of an anti-GDF15 antibody or fragment thereof described herein in a method of inhibiting or reducing one or more of: loss of body weight, muscle mass, appetite, or food intake, in a subject, e.g., a subject described herein.

In an embodiment, use of an anti-GDF15 antibody or fragment thereof described herein in the manufacture of a medicament for treatment of a wasting disorder, e.g., cachexia or sarcopenia, cancer, chronic heart failure, chronic kidney disease, COPD, AIDS, multiple sclerosis, rheumatoid arthritis, sepsis, or tuberculosis is provided.

Dosages and therapeutic regimens of the anti-GDF15 antibody can be determined by a skilled artisan. In certain embodiments, the anti-GDF15 antibody is administered by injection (e.g., subcutaneously or intravenously) at a dose of about 1 to 30 mg/kg, e.g., about 5 to 25 mg/kg, about 10 to 20 mg/kg, or about 1 to 5 mg/kg. The dosing schedule can vary from e.g., once a week to once every 2, 3, or 4 weeks.

The methods and compositions described herein can be used in combination with other agents or therapeutic modalities. In one embodiment, the methods described herein include administering to the subject an anti-GDF15 antibody as described herein, in combination with an agent or therapeutic procedure or modality, in an amount effective to treat or prevent a disorder. The anti-GDF15 antibody and the agent or therapeutic procedure or modality can be administered simultaneously or sequentially in any order. Any combination and sequence of the anti-GDF15 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody can be administered before the other treatment, concurrently with the treatment, post-treatment, or during remission of the disorder.

In another aspect, provided herein is a method for detecting the presence GDF15 in a sample, e.g., in vitro or in vivo (e.g., a biological sample, e.g., serum, semen or urine, or a tissue biopsy). The subject method can be used to evaluate (e.g., monitor treatment or progression of, diagnose and/or stage a disorder described herein, in a subject). The method includes: (i) contacting the sample with (and optionally, a reference, e.g., a control sample), or administering to the subject, an antibody molecule as described herein, under conditions that allow interaction to occur, and (ii) detecting formation of a complex between the antibody, and the sample (and optionally, the reference, e.g., control, sample).

Formation of the complex is indicative of the presence of GDF15, and can indicate the suitability or need for a treatment described herein. The method can involve an immunohistochemistry, immunocytochemistry, FACS, antibody molecule complexed magnetic beads, ELISA assays, PCR-techniques (e.g., RT-PCR).

Typically, the antibody used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials.

In another aspect, provided herein are diagnostic or therapeutic kits that include the antibodies described herein and instructions for use.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features, objects, and advantages of the disclosure will be apparent from the description and drawings, and from the claims.

Terminology

Unless defined otherwise, all technical and scientific terms used herein have the same meaning as commonly understood by those of ordinary skill in the art to which this disclosure pertains. Certain terms are defined below and throughout the application. As used herein, the articles "a," "an" and "the" refer to one or to more than one (e.g., to at least one) of the grammatical object of the article.

The term "or" is used herein to mean, and is used interchangeably with, the term "and/or", unless context clearly indicates otherwise.

Where elements are presented as lists, e.g., in Markush group format or "chosen from," each subgroup of the elements is also disclosed, and any element(s) can be removed from the group.

In general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "including" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The terms "GDF15 protein" or "GDF15 antigen" or "GDF15" are used interchangeably, and refer to the Growth Differentiation Factor 15 (GDF15) protein in different species. For example, SEQ ID NO: 1 (NCBI Reference Sequence: NP_004855.2) as set out in Table 1 provides an exemplary amino acid sequence of a human GDF15 protein, SEQ ID NO: 2 (NCBI Reference NM_004864.2) as set out in Table 1 provides an exemplary nucleic acid sequence encoding human GDF15, and human GDF15 has been described in previous reports and literature, where it is also known as MIC-1, PLAB, TGF-PL, PTGFB, PDF and NAG-1. The term "GDF15" includes naturally-occurring molecules from mammaliam species, such as human, cyno, rodent and other species.

Antibodies described herein can bind to GDF15 variants or mutants. The term "GDF15 variants or mutants" includes mutants of the natural GDF15 protein, which have substantially the same amino acid sequence as that of the native primary structure (amino acid sequence) described herein. Herein, the term "mutants of the natural human Growth Differentiation Factor 15 (GDF15) protein having substantially the same amino acid sequence" refers to such mutant proteins.

The term "antibody" as used herein refers to a protein, e.g., an immunoglobulin chain or fragment thereof, comprising at least one immunoglobulin variable domain sequence. The term "antibody" includes, for example, a monoclonal antibody (including a full length antibody which has an immunoglobulin Fc region). In one embodiment, an antibody comprises a full antibody, or a full length immunoglobulin chain. In another embodiment, an antibody comprises an antigen binding fragment (i.e., "antigen-binding portion") or functional fragment of a full length antibody, or a full length immunoglobulin chain.

In embodiments, the full antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The terms "heavy chain variable region" and "heavy chain variable domain" are used interchangeable herein. The heavy chain constant region is comprised of three domains, CH1, CH2 and CH3. Each light chain is comprised of a light chain variable region (abbreviated herein as VL) and a light chain constant region. The terms "light chain variable region" and "light chain variable domain" are used interchangeable herein. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

In an embodiment, an antibody is a monospecific antibody and binds a single epitope. E.g., a monospecific antibody having a plurality of immunoglobulin variable domain sequences, each of which binds the same epitope.

In an embodiment an antibody is a multispecific antibody, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody is a bispecific antibody, a trispecific antibody, or tetraspecific antibody.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antigen binding portion" or "antigen binding fragment" of an antibody, as used herein, refers to one or more fragments of an antibody that retain the ability to specifically bind to a given antigen (e.g., human GDF15)). Antigen binding functions of an antibody can be performed by fragments of an intact antibody. Examples of binding fragments encompassed within the term antigen binding portion or antigen binding fragment of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) an Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody (dAb) fragment (Ward et al., 1989 *Nature* 341:544-546), which consists of a VH domain or a VL domain; and (ix) an isolated complementarity determining region (CDR). These antibody fragments can be obtained using conventional techniques known to those with skill in the art, and the fragments are screened for utility in the same manner as are intact antibodies.

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 *Science* 242:423-426; and Huston et al., 1988 *Proc. Natl. Acad. Sci.* 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, *Nature Biotechnology*, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH$_1$-VH-CH$_1$) which, together with complementary light chain polypeptides, form a pair of antigen binding regions (Zapata et al., 1995 *Protein Eng.* 8(10):1057-1062; and U.S. Pat. No. 5,641,870).

In an embodiment, an antibody comprises a diabody, and a single-chain molecule, as well as an antigen-binding fragment of an antibody (e.g., Fab, F(ab')$_2$, and Fv). For example, an antibody can include a heavy (H) chain variable domain sequence (abbreviated herein as VH), and a light (L) chain variable domain sequence (abbreviated herein as VL). In an embodiment, an antibody comprises or consists of a heavy chain and a light chain. In another example, an antibody includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibodies can be monoclonal or polyclonal. An antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a $K_D$ of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a GDF15-binding antibody) refers to a binding reaction that is determinative of the presence of a cognate antigen (e.g., a human GDF15 or cynomolgus GDF15) in a heterogeneous population of proteins and other biologics. The phrases "an antibody recognizing an antigen" and "an antibody specific for an antigen" are used interchangeably herein with the term "an antibody which binds specifically to an antigen."

The term "GDF15 mediated" refers to the fact that GDF15 is known as an appetite-regulating member of the TGFβ superfamily, and that elevated GDF15 levels are associated with wasting disorders such as anorexia (e.g., anorexia cachexia).

An "GDF15-associated disorder," "GDF15-associated condition," or similar terms as used herein, refer to any number of conditions or diseases in which a reduction of GDF15 levels and/or biological activity is sought. These conditions include but are not limited to those involving wasting disorders such as anorexia cachexia, anorexia of the aged, anorexia nervosa, cachexia associated with cancer, cachexia associated with AIDS, cachexia associated with heart failure, cachexia associated with cystic fibrosis, cachexia associated with rheumatoid arthritis, cachexia associated with kidney disease, cachexia associated with COPD, cachexia associated with ALS, cachexia associated with renal failure or cachexia associated with hip fracture, and the like.

Other GDF15-associated diseases or disorders associated with or resulting from elevated GDF15 levels include sarcopenia, e.g., a clinical condition related to cachexia that is characterized by loss of skeletal muscle mass and muscle strength; and starvation. Starvation typically results in a loss of body fat and non-fat mass due to inadequate diet and/or nutritional uptake (Thomas (2007) *Clinical Nutrition* 26:389-399). The effects of starvation often are reversed by improving diet and nutritional, for example, protein, uptake.

Still other GDF15-associated diseases or disorders associated with or resulting from elevated GDF15 levels include, but are not limited to, disorders associated with aberrant appetite, fat mass, energy balance, and/or involuntary weight loss, and reduced mortality and morbidity of critically ill patients.

As used herein, "cachexia" means a metabolic syndrome associated with underlying disease and characterized by involuntary loss of muscle mass. Cachexia is often accompanied by involuntary weight loss, loss of fat mass, anorexia, inflammation, insulin resistance, fatigue, weakness, significant loss of appetite, and/or increased muscle protein breakdown. Cachexia is distinct from starvation, age-related loss of muscle mass, malabsorption, and hyperthyroidism. Underlying diseases associated with cachexia include cancer, chronic heart failure, chronic kidney disease, COPD, AIDS, multiple sclerosis, rheumatoid arthritis, sepsis, and tuberculosis.

As used herein, "sarcopenia" is understood to be a condition characterized primarily by loss of skeletal muscle mass and muscle strength. Sarcopenia is frequently associated with aging. See, Ruegg and Glass (2011) *Annual Rec. Pharmacol. Toxicol.* 51:373-395. In one approach, sarcopenia can be identified in a subject if a value of the appendicular skeletal muscle mass of a subject divided by the height of the subject in meters is more than two standard deviations below the young normal mean. (Thomas (2007) *Clin Nutr.* 26(4):389-99; Baumgartner et al. (1999) *Mech. Aging Dev.* 147:755-763).

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies described herein may include amino acid residues not encoded by human sequences (e.g., mutations introduced by random or site-specific mutagenesis in vitro or by somatic mutation in vivo).

A "humanized" antibody is an antibody that retains the antigen-specific reactivity of a non-human antibody, e.g., a mouse monoclonal antibody, while being less immunogenic when administered as a therapeutic in humans. See, e.g., Robello et al., Transplantation, 68: 1417-1420. This can be achieved, for instance, by retaining the non-human antigen-binding regions and replacing the remaining parts of the antibody with their human counterparts (i.e., the constant region as well as portions of the variable region not involved in binding). See, e.g., Morrison et al., *Proc. Natl. Acad. Sci. USA*, 81:6851-6855, 1984; Morrison and Oi, *Adv. Immunol.*, 44:65-92, 1989; Verhoeyen et al., *Science*, 239:1534-1536, 1988; Padlan, *Molec. Immun.*, 28:489-498, 1991; and Padlan, *Molec. Immun.*, 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch, J. *Mol. Biol.* 48:443, 1970, by the search for similarity method of Pearson and Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (*Comput. Appl. Biosci.*, 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. *Mol, Biol.* 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds GDF15 is substantially free of antibodies that specifically bind antigens other than GDF15). An isolated antibody that specifically binds GDF15 may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$", as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a Biacore® system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985; and Rossolini et al., *Mol. Cell. Probes* 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g., mammals and non-mammals) such as, non-human primates (e.g., cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (e.g., GDF15 associated disorder) refers to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., a GDF15 associated disorder, means any action that prevents or slows a worsening in e.g., a GDF15 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

BRIEF DESCRIPTION OF THE DRAWINGS

FIG. 1A is a bar graph depicting the daily food intake (grams) after days post injection (1, 3, 5, 7, 10, 11 and 15 days). Measurements for three groups are provided for each time post antibody injection, from left to right: Vector+Vehicle; hGDF15+Control IgG; and hGDF15+ABGDF15-A. FIG. 1B is a linear graph depicting the percent changes in body weight after days post injection (1, 3, 5, 7, 10, 11 and 15 days). Measurements for three groups are provided for each time post injection tested: Vector+Vehicle; hGDF15+Control IgG; and hGDF15+ABGDF15-A. Statistical analysis was conducted using Student's t-Test for both studies, wherein *, **: $p<0.05$ and 0.01, ABGDF15-A vs. Vehicle; &, &&, &&&: $p<0.05$, 0.01 and 0.001, ABGDF15-A vs. Ctrl IgG.

FIGS. 2A-2B are linear graphs depicting the cumulative food intake (grams) and percent changes in body weight, respectively, after days post antibody injection (1, 4, 8, 12 and 16 days). The following treatment groups were illustrated in FIGS. 2A-2B: Vector+Vehicle; hGDF15+Control IgG; hGDF15+parent antibody (30 mg/kg); hGDF15+ parent antibody (10 mg/kg); hGDF15+parent antibody (3 mg/kg); and hGDF15+parent antibody (1 mg/kg). The parent antibody dose-dependently reversed GDF15-mediated anorexic effects.

FIGS. 3A-3B are a linear graph and bar graph depicting daily food intake (grams) and the percent changes in body weight, respectively, after days post injection. The following groups were illustrated in FIGS. 3A-3B: Vector+Vehicle; hGDF15+Control IgG; hGDF15+ABGDF15-D for each time point. ABGDF15-D reversed GDF15-mediated anorexic effects.

FIG. 6 is a summary of the epitope mapping of anti-GDF15 antibodies based on loss-of-binding, or partially inhibited binding, to certain GDF15 fragments and mutations using ELISA. The antibodies tested were ABGDF15-A, -B, -C, -D, -E, -F and -G, and Hu01G06 (a humanized version of anti-GDF15 antibody 01G06) shown in the first column. The following wild-type and mutant GDF15 variants were tested: Wild-type human GDF15, rodent GDF15, cyno GDF15, N-terminal-truncated hGDF15 (having amino acids 211-308), GDF15 mutants having a mutation in the knuckle region (L294R, I285R, or S231R), wrist region (Q247R, W228R, or M253R), finger tip region (D289R) and back-of-hand (S278R). "Knuckle", "wrist", "finger tip" and "back-of-hand" are 3-dimensional domains, termed based on homologous crystal structures of all TGFβ family proteins (ref. Mueller and Nickel (2012) *Promiscuity and specificity in BMP receptor activation. FEBS Letters* 586: 1846-1859. ABGDF15-A, -B, -C, -D, -E, -F and -G all bind to the knuckle domain. Loss-of-binding, partially inhibited binding ("inhibited"), and no effect by mutation, are depicted by different striped areas.

FIG. 7 is an alignment of the amino acid sequences for the heavy and light chain CDRs (SEQ ID NOS 194, 194 and 195-199, respectively, in order of appearance).

BRIEF DESCRIPTION OF THE TABLES

Figure 1A:
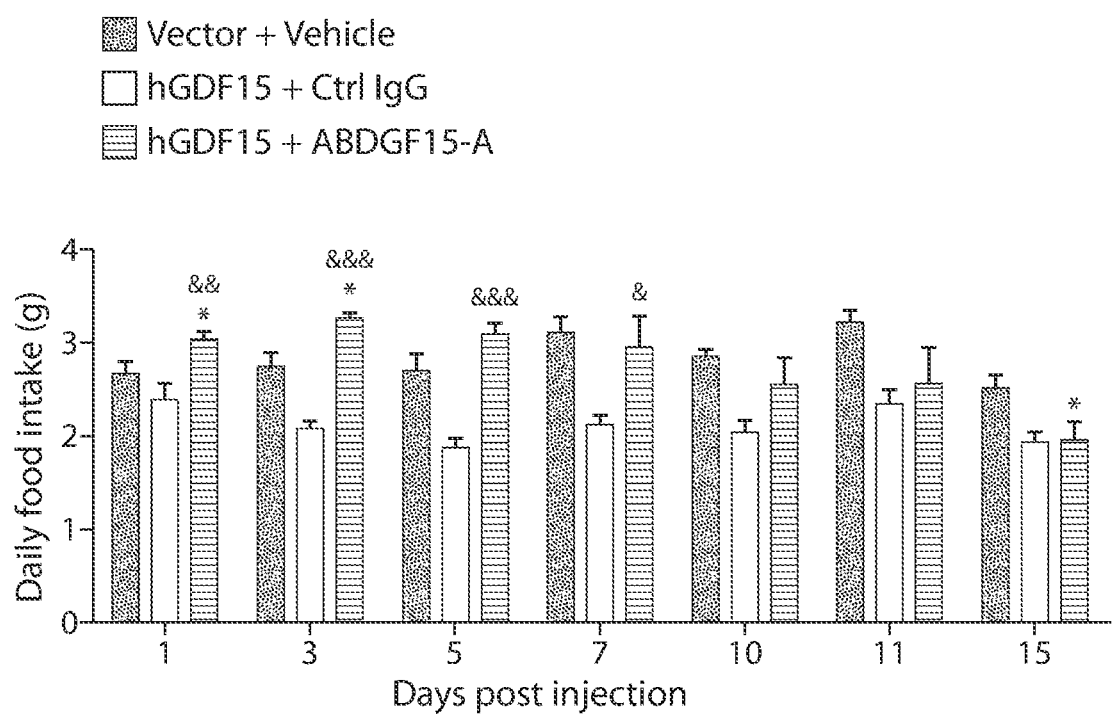
FIGS. 1A-1B depict a time course of the effects of ABGDF15-A in blocking GDF15-mediated suppression of food intake and weight loss in diet-induced obesity (DIO) mice. Human GDF15 was expressed in liver by DNA hydrodynamic injection (HDI) of a human full-length GDF15 expression vector, leading to ~10% weight loss by day 7, prior to anti-GDF15 antibody administration (day 0 in the figure). One group of mice were injected with empty vector as negative control (Vector). Body weight and plasma human GDF15 levels were determined for individual mice and the animals were divided into two groups based on comparable average body weight and GDF15 levels. Abs (ABGDF15-A or an irrelevant control Ab) were administered intravenously at 10 mg/kg, and food intake and body weight were monitored.

Table 1 is a summary of the amino acid and nucleotide sequences for the anti-GDF15 antibody molecules. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 is a summary of the binding characteristics of the anti-GDF15 antibodies described herein. For each antibodies, the following parameters are provided: ka (1/Ms), kd (1/s), $K_D$ (M) and Rmax (RU) for each of the ligands identified.

Table 3 is a summary of the $K_D$ values of ABGDF-A through ABGDF-G, as determined by SET or Biacore.

Table 4 is a summary of the pI values of ABGDF-A through ABGDF-G.

DETAILED DESCRIPTION

The present disclosure is based, in part, on the discovery of antibody molecules that specifically bind to GDF15 and inhibit its wasting-associated and pathological effects, levels, and/or activities, e.g., its ability in a disease state to reduce appetite; and/or to reduce food intake, body weight, and/or fat mass. Provided herein are both full IgG format antibodies (e.g., human antibodies), as well as antigen binding fragments thereof, such as Fab fragments (e.g., antibodies ABGDF15-A, ABGDF15-G, ABGDF15-B, ABGDF15-C, ABGDF15-F, ABGDF15-E, and ABGDF15-D).

The anti-GDF15 antibody molecules described herein are capable of binding to the C-terminal region of GDF15, e.g., the knuckle domain of GDF15. As disclosed in Example 5, ABGDF15-A, ABGDF15-G, ABGDF15-B, ABGDF15-C, ABGDF15-F, ABGDF15-E, and ABGDF15-D bind to the knucke domain of human GDF15. FIG. 6 shows that the binding of ABGDF15-A, ABGDF15-D, ABGDF15-E, ABGDF15-F, or ABGDF15-G to human GDF15 was lost when the knuckle domain mutation L294R or I285R was present. Similarly, FIG. 6 shows that the binding of ABGDF15-B or ABGDF15-C to human GDF15 was lost when the knucke domain mutation I285R or S231R was present. In comparison, N-terminal truncation of human GDF15, and mutations in the wrist domain (Q247R, W228R, M253R, and Q295R), finger tip region (D289R), and back-of-hand domain (S278R) had no effect on binding of the exemplary anti-GDF15 antibody molecules.

Without wishing to be bound by theory, it is believed that in certain embodiments, the specific binding to the C-terminal region of GDF15 (e.g., the knuckle domain) confers, at least in part, the biological functions and/or clinical effects of the anti-GDF15 antibody molecules described herein.

As shown in Example 6, knuckle domain-binding antibody molecules, i.e., ABGDF15-A, ABGDF15-G, ABGDF15-B, ABGDF15-C, ABGDF15-F, ABGDF15-E, and ABGDF15-D, reversed GDF15-mediated weight loss, as demonstrated in a mouse anorexia model. The anti-GDF15 antibody molecules described herein can be used, e.g., to treat a GDF15-associated disorder, to increase appetite and/or food intake, to increase body weight, or to inhibit or reduce one or more of: loss of body weight, muscle mass, appetite, or food intake. For example, subjects having one or more of anorexia, sarcopenia, or cachexia associated with aging, cancer, heart failure, COPD, and/or renal failure, or subjects having a wasting disorder, can be treated with the antibody molecules described herein. The antibody molecules described herein are also suitable for treating subjects having a cancer, chronic heart failure, a chronic kidney disease, COPD, AIDS, multiple sclerosis, rheumatoid arthritis, sepsis, or tuberculosis.

Accordingly, provided herein are antibodies that specifically bind to GDF15 (e.g., human GDF15), pharmaceutical compositions, production methods, and methods of use of such antibodies and compositions.

GDF15 Proteins

Provided herein are antibodies that specifically bind to GDF15 and inhibits its biological activities and/or depletes free GDF15 from circulation.

Growth Differentiation Factor 15 (GDF15) is a divergent member of the TGFβ superfamily, and is also referred to as macrophage inhibitory cytokine 1 (M1C1) (Bootcov M R, 1997, Proc Natl Acad Sci 94: 11514-9), placental bone morphogenetic factor (PLAB) (Hromas R 1997, Biochim Biophys Acta. 1354:40-4), placental transforming growth factor beta (PTGFB) (Lawton L N 1997, Gene. 203: 17-26), prostate derived factor (PDF) (Paralkar V M 1998, J Biol Chem. 273: 13760-7), and nonsteroidal antiinflammatory drug-activated gene (NAG-1) (Baek S J 2001, J Biol Chem. 276: 33384-92). The mature GDF15 peptide shares low homology with other family members (Katoh M 2006, Int J Mol Med. 17:951-5). GDF15 is synthesized as a large precursor protein that is cleaved at the dibasic cleavage site to release the carboxyterminal mature peptide. Human full-length precursor contains 308 amino acids and is cleaved at the RGRRRAR (SEQ ID NO:185) cleavage site to produce the mature GDF peptide. Naturally occurring GDF15 is a 25 KD homodimer of the mature peptide covalently linked by one inter-chain disulfide bond. GDF15 is reported to be relevant to a number of different physiological and pathologic conditions. For example, studies of GDF15 knockout and transgenic mice suggest that GDF15 may be protective against ischemic/reperfusion- or overload-induced heart injury (Kempf T, 2006, Circ Res. 98:351-60) (Xu J, 2006, Circ Res. 98:342-50), protective against aging-associated motor neuron and sensory neuron loss (Strelau J, 2009, J Neurosci. 29: 13640-8), mildly protective against metabolic acidosis in kidney, and may cause cachexia in cancer patients (Johnen H 2007 Nat Med. 11: 1333-40). GDF15 is also reported to be protective against carcinogen- or Apc mutation-induced neoplasia in intestine and lung (Baek S J 2006, Gastroenterology. 131: 1553-60; Cekanova M 2009, Cancer Prev Res 2:450-8).

GDF15 contains multiple domains, including, e.g., the fingers domain, knuckle domain, wrist domain, N-terminal loop domain, and back-of-hand domain. A series of structure-guided site-directed mutants were designed to elucidate domains and residues essential for function (see e.g., International Application No. WO 2015198199).

GDF15 analogs that disrupt the amino-terminus region of GDF15, e.g., mouse serum albumin (MSA)-GDF15 (211-308) and MSA-GDF15 (C2035, C2105), still retain biological activity, indicating that this loop is not required for activity.

The knuckle, finger, and wrist region of TGFbeta superfamily members are known to be important for receptor binding and signaling. To determine if these regions of GDF15 are important for activity, key surface residues have been mutated to a large side-chain containing amino acid, arginine, to attempt to induce a loss of function (see, e.g., WO 2015198199). MSA-GDF15 fusion proteins containing mutations in GDF15 residues leucine 294 (knuckle), aspartic acid 289 (fingers), glutamine 247 (wrist), and serine 278 (back of hand) were produced and then dosed subcutaneously to obese mice (e.g., 3 mg/kg s.c.). A single subcutaneous injection of MSA-GDF15 reduced food intake over the course of 7 days by 30% compared to vehicle control. Food intake was also reduced relative to control by the finger region mutant (D289R), the wrist mutant (Q247R), and the back of the hand mutant (S278R) by 22, 14, and 24%, respectively. In comparison, the knuckle region mutant (L294R) increased food intake by 17% relative to control. Over the course of the 7 days, body weight increased in the vehicle and L294R treated mice (2.2 and 6.3% respectively) while body weight decreased by 6.6, 5.7, 5.7, and 5.4% in the MSA-GDF15, MSA-GDF15 (D289R), MSA-GDF15 (Q247R), and MSA-GDF15 (S278R) treated mice, respectively. These data indicate that the knuckle region of GDF15 (such as L294) are important for activity. Mutations in the other regions of GDF15 are generally tolerated.

GDF15 has anorexigenic effects, particularly in cancer (Brown D. A. Clinical Cancer Res 2003; 9:2642-2650; Koopmann J. Clinical Cancer Res 2006; 12:442-446). Substantial elevation of circulating MIC-1/GDF15 levels in cancers and other diseases such as chronic renal or cardiac failure are associated with a lower body mass index (Breit S. N. et al, Growth factors 2011; 29:187-195; Johnen H. et al, Nat Med. 2007; 13:1333-1340), suggesting that apart from any role in inflammation in disease, MIC-1/GDF15 may also play a role in body weight regulation. Long-term elevated expression of MIC-1/GDF15 in mice leads to decreased food intake, body weight and adiposity with concomitantly improved glucose tolerance, both under normal and obesogenic dietary conditions (Macia L. et al, PloS One 2012; 7(4):e34868). Food intake and body weight are controlled by a variety of central and peripheral factors, but the exact mechanisms behind these processes are still not fully understood.

Although cachexia is a complex and incompletely understood syndrome, it is clear that GDF15 is an important mediator of cachexia in various diseases (Tsai et al., supra). At least some tumors over-express and secrete GDF15, and elevated serum GDF15 levels have been associated with various cancers (Johnen et al. (2007) Nat. Med. 13:1333-1340; Bauskin et al. (2006) Cancer Res. 66:4983-4986). Monoclonal antibodies against GDF15 have been recognized as potential anti-cachexia therapeutic agents. See, e.g., U.S. Pat. No. 8,192,735.

In certain aspects, circulating GDF15 levels are markedly elevated in many anorexic-cachectic states in humans. In particular embodiments, a non-limiting example of a normal physiological range of GDF15 levels is ~150-1150 pg/mL (6-50 pM). In specific embodiments, a subject treated with an anti-GDF15 antibody described herein has GDF15 levels greater than 150 pg/mL, or greater than 1000 pg/mL, or greater than 1150 pg/mL. In specific embodiments, a non-limiting example of the median in a community elderly (e.g., 65 years of age or higher) population is approximately 1370 (55 pM): with CVM median approximately 1740 (70 pM). In certain embodiments, exemplary GDF15 levels in pregnant women (e.g., a sampling or population of pregnant women) are up to approximately 15,000 pg/mL (600 pM). In certain embodiments, subjects afflicted with (i) Beta-thalassemia have non-limiting, exemplary GDF15 levels of up to approximately 60,000 pg/mL (2,400 pM); (ii) Pulmonary embolism have non-limiting, exemplary GDF15 levels of up to approximately 48000 pg/mL (1,900 pM); (iii) Colorectal cancer have non-limiting, exemplary GDF15 levels of ~10,000 pg/mL (400 pM); (iv) severe chronic kidney disease have non-limiting, exemplary GDF15 levels of on average approximately 8400 pg/mL (360 pM); (v) pancreatic cancer have non-limiting, exemplary average GDF15 levels of approximately 5388 pg/mL (220 pM); (vi) anorexia nervosa have non-limiting, exemplary GDF15 levels of up to approximately 2000 pg/mL (80 pM); (vi) Type 2 Diabetes have non-limiting, exemplary average GDF15 levels of approximately 1200 pg/mL (50 pM); and (vii) obesity have non-limiting, exemplary average GDF15 levels of approximately 500 pg/mL (20 pM).

In particular embodiments, subjects afflicted with chronic heart failure have non-limiting, exemplary GDF15 levels of up to approximately 1,082 (802-1,502) (50 pM), for example, in the case of survivors, whereas non-survivors have non-limiting, exemplary GDF15 levels of approximately 1,900 (1,357-2,671) pg/mL (80 pM). In specific embodiments, prostate cancer subjects have non-limiting, exemplary GDF15 levels on average of approximately 12,416 pg/mL (500 pM), and in the cases of prostate cancer subjects who do not experience cachexia, non-limiting, exemplary average GDF15 levels are approximately 3,265 pg/mL (130 pM).

In particular embodiments, the anti-GDF15 antibodies and antigen binding fragments described herein decrease levels and/or biological activity of GDF15, e.g., by binding to and neutralizing GDF15. In specific embodiments, anti-GDF15 antibodies described herein are expected to prevent and ameliorate the acute and chronic manifestations of diseases characterized by elevated GDF15 levels, e.g., cachexia, sarcopenia, and the like. In certain embodiments, anti-GDF15 antibodies (e.g., ABGDF15-A, ABGDF15-B, ABGDF15-C, ABGDF15-D, ABGDF15-E, ABGDF15-F, or ABGDF15-G) and antigen binding fragments described herein increase appetite or food intake, for example, by at least 1%, 2%, 3%, 4%, 5%, 6%, 7%, 8%, 9%, 10%, 11%, 12%, 13%, 14%, 15%, 16%, 17%, 18%, 19%, or 20%, in a subject. In particular embodiments, anti-GDF15 antibodies (e.g., ABGDF15-A, ABGDF15-B, ABGDF15-C, ABGDF15-D, ABGDF15-E, ABGDF15-F, or ABGDF15-G) and antigen binding fragments described herein increase body weight, for example, by at least 1%, 2%, 3%, 4%, 5%, 6%, 7%, 8%, 9%, 10%, 11%, 12%, 13%, 14%, 15%, 16%, 17%, 18%, 19%, or 20%, in a subject. The anti-GDF15 antibodies and antigen binding fragments described herein decrease levels and/or biological activity of GDF15, e.g., by binding to and neutralizing GDF15. These antibodies are expected to prevent and ameliorate the acute and chronic manifestations of diseases characterized by elevated GDF15 levels, e.g., cachexia, sarcopenia, and the like.

GDF15 Antibodies & Antigen Binding Fragments

Antibodies that specifically bind to GDF15, e.g., human GDF15, are disclosed. Said antibodies include, but are not limited to, the human monoclonal antibodies and Fabs, isolated as described in the Examples.

In one aspect, provided herein are antibodies that specifically bind a GDF15 protein (e.g., human GDF15), wherein the antibodies comprise a VH domain having an amino acid sequence of SEQ ID NOs: 12, 38, 64, 90, 116, 142, or 168. Also provided are antibodies that specifically bind to a GDF15 protein, wherein the antibodies comprise a VH CDR having an amino acid sequence of any one of the VH CDRs listed in Table 1, infra. In one embodiment, provided herein are antibodies that specifically bind to an GDF15 protein (e.g., human GDF15), wherein the antibodies comprise (or alternatively, consist of) one, two, three, or more VH CDRs having an amino acid sequence of any of the VH CDRs listed in Table 1, infra.

In some embodiments, antibodies that specifically bind to a GDF15 protein are provided, said antibodies comprising a VL domain having an amino acid sequence of SEQ ID NOs: 25, 51, 77, 103, 129, 155, or 181. Also provided are antibodies that specifically bind to an GDF15 protein (e.g., human GDF15), said antibodies comprising a VL CDR having an amino acid sequence of any one of the VL CDRs listed in Table 1, infra. In particular, antibodies that specifically bind to an GDF15 protein (e.g., human GDF15) are disclosed, said antibodies comprising (or alternatively, consisting of) one, two, three or more VL CDRs having an amino acid sequence of any of the VL CDRs listed in Table 1, infra.

Other antibodies include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

Also provided are nucleic acid sequences that encode VH, VL, the full length heavy chain, and the full length light chain of the antibodies that specifically bind to a GDF15 protein (e.g., human GDF15). Such nucleic acid sequences can be optimized for expression in mammalian cells (for example, Table 1 shows the optimized nucleic acid sequences for the heavy chain and light chain of antibodies described herein).

TABLE 1

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| 1 | Human GDF15 amino acid sequence (NCBI Reference Sequence: NP_004855.2) | MPGQELRTVN GSQMLLVLLV LSWLPHGGAL SLAEASRASF PGPSELHSED SRFRELRKRY EDLLTRLRAN QSWEDSNTDL VPAPAVRILT PEVRLGSGGH LHLRISRAAL PEGLPEASRL HRALFRLSPT ASRSWDVTRP LRRQLSLARP QAPALHLRLS PPPSQSDQLL AESSSARPQL ELHLRPQAAR GRRRARARNG DHCPLGPGRC CRLHTVRASL EDLGWADWVL SPREVQVTMC IGACPSQFRA ANMHAQIKTS LHRLKPDTVP APCCVPASYN PMVLIQKTDT GVSLQTYDDL LAKDCHCI |
| 2 | Human GDF15 nucleic acid sequence (NCBI Reference NM_004864.2) | agtcccagct cagagccgca acctgcacag ccatgcccgg gcaagaactc aggacggtga atgctctca gatgctcctg gtgttgctgg |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | tgctctcgtg gctgccgcat gggggcgccc tgtctctggc cgaggcgagc cgcgcaagtt tcccgggacc ctcagagttg cactccgaag actccagatt ccgagagttg cggaaacgct acgaggacct gctaaccagg ctgcgggcca accagagctg ggaagattcg aacaccgacc tcgtcccggc ccctgcagtc cggatactca cgccagaagt gcggctggga tccggcggcc acctgcacct gcgtatctct cgggccgccc ttcccgaggg gctccccgag gcctcccgcc ttcaccgggc tctgttccgg ctgtccccga cggcgtcaag gtcgtgggac gtgacacgac cgctgcggcg tcagctcagc cttgcaagac cccaggcgcc cgcgctgcac ctgcgactgt cgccgccgcc gtcgcagtcg gaccaactgc tggcagaatc ttcgtccgca cggcccagc tggagttgca cttgcggccg caagccgcca gggggcgccg cagagcgcgt gcgcgcaacg gggaccactg tccgctcggg cccgggcgtt gctgccgtct gcacacggtc cgcgcgtcgc tggaagacct gggctgggcc gattgggtgc tgtcgccacg ggaggtgcaa gtgaccatgt gcatcggcgc gtgcccgagc cagttccggg cggcaaacat gcacgcgcag atcaagacga gcctgcaccg cctgaagccc gacacggtgc cagcgccctg ctgcgtgccc gccagctaca atcccatggt gctcattcaa aagaccgaca ccggggtgtc gctccagacc tatgatgact tgttagccaa agactgccac tgcatatgag cagtcctggt ccttccactg tgcacctgcg cggaggacgc gacctcagtt gtcctgccct gtggaatggg ctcaaggttc ctgagacacc cgattcctgc ccaaacagct gtatttatat aagtctgtta tttattatta atttattggg gtgaccttct tggggactcg ggggctggtc tgatggaact gtgtatttat ttaaaactct ggtgataaaa ataaagctgt ctgaactgtt aaaaaaaaaa aaaaaaaaaa |

ABGDF15-A

| SEQ ID NO: 3 | HCDR1 (Combined) | GYSFTDYWIS |
| SEQ ID NO: 4 | HCDR2 (Combined) | IIDPSGSYTIYSPSFQG |
| SEQ ID NO: 5 | HCDR3 (Combined) | VSYYGGYFDI |
| SEQ ID NO: 6 | HCDR1 (Kabat) | DYWIS |
| SEQ ID NO: 7 | HCDR2 (Kabat) | IIDPSGSYTIYSPSFQG |
| SEQ ID NO: 8 | HCDR3 (Kabat) | VSYYGGYFDI |
| SEQ ID NO: 9 | HCDR1 (Chothia) | GYSFTDY |
| SEQ ID NO: 10 | HCDR2 (Chothia) | DPSGSY |
| SEQ ID NO: 11 | HCDR3 (Chothia) | VSYYGGYFDI |
| SEQ ID NO: 12 | VH | EVQLVQSGAEVKKPGESLKISCKGSGYSFTDYWISWVRQ MPGKGLEWMGIIDPSGSYTIYSPSFQGQVTISADKSISTA YLQWSSLKASDTAMYYCARVSYYGGYFDIWGQGTLVTV SS |
| SEQ ID NO: 13 | DNA VH | GAAGTGCAACTCGTGCAGTCCGGAGCCGAAGTGAAAAA GCCAGGAGAGTCCCTGAAGATCAGCTGCAAGGGATCCG GATACTCCTTCACCGACTACTGGATTTCGTGGGTCCGCC AGATGCCCGGAAGGGCCTGGAGTGGATGGGGATCATC GATCCGTCTGGTTCCTACACTATCTACTCGCCGTCGTTC CAAGGACAGGTCACCATCTCCGCCGACAAGTCCATTAG CACCGCGTATCTGCAGTGGAGCTCACTGAAGGCCTCCG |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | ACACCGCAATGTACTACTGCGCGCGGGTGTCATACTAC GGCGGTTACTTTGATATTTGGGGCCAGGGGACTCTGGT CACTGTGTCGTCC |
| SEQ ID NO: 14 | Heavy Chain | EVQLVQSGAEVKKPGESLKISCKGSGYSFTDYWISWVRQ MPGKGLEWMGIIDPSGSYTIYSPSFQGQVTISADKSISTA YLQWSSLKASDTAMYYCARVSYYGGYFDIWGQGTLVTV SSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSKLTVDKSRWQQGNVF SCSVMHEALHNHYTQKSLSLSPGK |
| SEQ ID NO: 15 | DNA Heavy Chain | GAAGTGCAACTCGTGCAGTCCGGAGCCGAAGTGAAAAA GCCAGGAGAGTCCCTGAAGATCAGCTGCAAGGGATCCG GATACTCCTTCACCGACTACTGGATTTCGTGGGTCCGCC AGATGCCCGGGAAGGGCCTGGAGTGGATGGGGATCATC GATCCGTCTGGTTCCTACACTATCTACTCGCCGTCGTTC CAAGGACAGGTCACCATCTCCGCCGACAAGTCCATTAG CACCGCGTATCTGCAGTGGAGCTCACTGAAGGCCTCCG ACACCGCAATGTACTACTGCGCGCGGGTGTCATACTAC GGCGGTTACTTTGATATTTGGGGCCAGGGGACTCTGGT CACTGTGTCGTCCGCTAGCACCAAGGGCCCAAGTGTGT TTCCCCTGGCCCCCAGCAGCAAGTCTACTTCCGGCGGAA CTGCTGCCCTGGGTTGCCTGGTGAAGGACTACTTCCCCG AGCCCGTGACAGTGTCCTGGAACTCTGGGGCTCTGACT TCCGGCGTGCACACCTTCCCCGCCGTGCTGCAGAGCAGC GGCCTGTACAGCCTGAGCAGCGTGGTGACAGTGCCCTC CAGCTCTCTGGGAACCCAGACCTATATCTGCAACGTGA ACCACAAGCCCAGCAACACCAAGGTGGACAAGAGAGTG GAGCCCAAGAGCTGCGACAAGACCCACACCTGCCCCCCC TGCCCAGCTCCAGAACTGCTGGGAGGGCCTTCCGTGTT CCTGTTCCCCCCCAAGCCCAAGGACACCCTGATGATCAG CAGGACCCCCGAGGTGACCTGCGTGGTGGTGGACGTGT CCCACGAGGACCCAGAGGTGAAGTTCAACTGGTACGTG GACGGCGTGGAGGTGCACAACGCCAAGACCAAGCCCAG AGAGGAGCAGTACAACAGCACCTACAGGGTGGTGTCCG TGCTGACCGTGCTGCACCAGGACTGGCTGAACGGCAAA GAATACAAGTGCAAAGTCTCCAACAAGGCCCTGCCAGC CCCAATCGAAAAGACAATCAGCAAGGCCAAGGGCCAGC CACGGGAGCCCCAGGTGTACACCCTGCCCCCCAGCCGGG AGGAGATGACCAAGAACCAGGTGTCCCTGACCTGTCTG GTGAAGGGCTTCTACCCCAGCGATATCGCCGTGGAGTG GGAGAGCAACGGCCAGCCCGAGAACAACTACAAGACCA CCCCCCCAGTGCTGGACAGCGACGGCAGCTTCTTCCTGT ACAGCAAGCTGACCGTGGACAAGTCCAGGTGGCAGCAG GGCAACGTGTTCAGCTGCAGCGTGATGCACGAGGCCCT GCACAACCACTACACCCAGAAGTCCCTGAGCCTGAGCCC CGGCAAG |
| SEQ ID NO: 16 | LCDR1 (Combined) | RASQSISNNLN |
| SEQ ID NO: 17 | LCDR2 (Combined) | AASNLQS |
| SEQ ID NO: 18 | LCDR3 (Combined) | FQLDHSPFT |
| SEQ ID NO: 19 | LCDR1 (Kabat) | RASQSISNNLN |
| SEQ ID NO: 20 | LCDR2 (Kabat) | AASNLQS |
| SEQ ID NO: 21 | LCDR3 (Kabat) | FQLDHSPFT |
| SEQ ID NO: 22 | LCDR1 (Chothia) | SQSISNN |
| SEQ ID NO: 23 | LCDR2 (Chothia) | AAS |
| SEQ ID NO: 24 | LCDR3 (Chothia) | LDHSPF |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| SEQ ID NO: 25 | VL | DIQMTQSPSSLSASVGDRVTITCRASQSISNNLNWYQQK PGKAPKLLIYAASNLQSGVPSRFSGSGSGTDFTLTISSLQP EDFATYYCFQLDHSPFTFGQGTKVEIK |
| SEQ ID NO: 26 | DNA VL | GACATTCAGATGACCCAGAGCCCTTCCTCCCTGTCCGCC TCCGTGGGAGATCGCGTGACCATCACTTGCCGGGCCAG CCAGTCGATTTCAAACAACCTGAACTGGTACCAGCAGA AACCGGGAAAGGCCCCCAAGCTGTTGATCTACGCGGCC AGCAATCTCCAGTCCGGCGTGCCGTCAAGATTCTCCGG GAGCGGTTCGGGCACTGACTTCACCCTGACCATCTCCTC GCTGCAACCCGAAGATTTCGCAACCTACTACTGTTTCC AACTGGACCACTCTCCATTCACATTTGGGCAGGGCACC AAGGTCGAGATCAAG |
| SEQ ID NO: 27 | Light Chain | DIQMTQSPSSLSASVGDRVTITCRASQSISNNLNWYQQK PGKAPKLLIYAASNLQSGVPSRFSGSGSGTDFTLTISSLQP EDFATYYCFQLDHSPFTFGQGTKVEIKRTVAAPSVFIFPP SDEQLKSGTASVVCLLNNFYPREAKVQWKVDNALQSGN SQESVTEQDSKDSTYSLSSTLTLSKADYEKHKVYACEVT HQGLSSPVTKSFNRGEC |
| SEQ ID NO: 28 | DNA Light Chain | GACATTCAGATGACCCAGAGCCCTTCCTCCCTGTCCGCC TCCGTGGGAGATCGCGTGACCATCACTTGCCGGGCCAG CCAGTCGATTTCAAACAACCTGAACTGGTACCAGCAGA AACCGGGAAAGGCCCCCAAGCTGTTGATCTACGCGGCC AGCAATCTCCAGTCCGGCGTGCCGTCAAGATTCTCCGG GAGCGGTTCGGGCACTGACTTCACCCTGACCATCTCCTC GCTGCAACCCGAAGATTTCGCAACCTACTACTGTTTCC AACTGGACCACTCTCCATTCACATTTGGGCAGGGCACC AAGGTCGAGATCAAGCGTACGGTGGCCGCTCCCAGCGT GTTCATCTTCCCCCCCAGCGACGAGCAGCTGAAGAGCG GCACCGCCAGCGTGGTGTGCCTGCTGAACAACTTCTAC CCCCGGGAGGCCAAGGTGCAGTGAAGGTGGACAACGC CCTGCAGAGCGGCAACAGCCAGGAGAGCGTCACCGAGC AGGACAGCAAGGACTCCACCTACAGCCTGAGCAGCACC CTGACCCTGAGCAAGGCCGACTACGAGAAGCATAAGGT GTACGCCTGCGAGGTGACCCACCAGGGCCTGTCCAGCCC CGTGACCAAGAGCTTCAACAGGGGCGAGTGC |
| ABGDF15-G | | |
| SEQ ID NO: 29 | HCDR1 (Combined) | GGTFSSHYIN |
| SEQ ID NO: 30 | HCDR2 (Combined) | GIIPAFGGANYAQKFQG |
| SEQ ID NO: 31 | HCDR3 (Combined) | FGSVYVSRYSSYYHMDV |
| SEQ ID NO: 32 | HCDR1 (Kabat) | SHYIN |
| SEQ ID NO: 33 | HCDR2 (Kabat) | GIIPAFGGANYAQKFQG |
| SEQ ID NO: 34 | HCDR3 (Kabat) | FGSVYVSRYSSYYHMDV |
| SEQ ID NO: 35 | HCDR1 (Chothia) | GGTFSSH |
| SEQ ID NO: 36 | HCDR2 (Chothia) | IPAFGG |
| SEQ ID NO: 37 | HCDR3 (Chothia) | FGSVYVSRYSSYYHMDV |
| SEQ ID NO: 38 | VH | QVQLVQSGAEVKKPGSSVKVSCKASGGTFSSHYINWVR QAPGQGLEWMGGIIPAFGGANYAQKFQGRVTITADEST STAYMELSSLRSEDTAVYYCARFGSVYVSRYSSYYHMDV WGQGTLVTVSS |
| SEQ ID NO: 39 | DNA VH | CAAGTGCAACTCGTGCAGTCGGGAGCCGAAGTCAAGAA GCCGGGGAGCTCGGTGAAAGTGTCCTGCAAGGCCTCCG GGGGAACTTTCAGCTCCCACTACATCAACTGGGTCAGA CAGGCGCCCGGACAGGGGTTGGAATGGATGGGCGGAAT CATCCCGGCGTTTGGCGGCGCGAACTACGCCCAGAAGT TCCAGGGTCGGGTCACCATTACCGCCGACGAGTCCACT TCCACTGCATACATGGAGCTGTCCTCACTGCGGAGCGA AGATACCGCCGTGTATTACTGCGCCCCGCTTCGGATCTG |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
|  |  | TGTACGTGTCCCGCTACTCCTCATACTACCATATGGAC<br>GTCTGGGGACAGGGCACCCTGGTCACGGTGTCGTCC |
| SEQ ID NO: 40 | Heavy Chain | QVQLVQSGAEVKKPGSSVKVSCKASGGTFSSHYINWVR<br>QAPGQGLEWMGGIIPAFGGANYAQKFQGRVTITADEST<br>STAYMELSSLRSEDTAVYYCARFGSVYVSRYSSYYHMDV<br>WGQGTLVTVSSASTKGPSVFPLAPSSKSTSGGTAALGCL<br>VKDYFPEPVTVSWNSGALTSGVHTFPAVLQSSGLYSLSS<br>VVTVPSSSLGTQTYICNVNHKPSNTKVDKRVEPKSCDKT<br>HTCPPCPAPELLGGPSVFLFPPKPKDTLMISRTPEVTCV<br>VVDVSHEDPEVKFNWYVDGVEVHNAKTKPREEQYNST<br>YRVVSVLTVLHQDWLNGKEYKCKVSNKALPAPIEKTISK<br>AKGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK |
| SEQ ID NO: 41 | DNA Heavy Chain | CAAGTGCAACTCGTGCAGTCGGGAGCCGAAGTCAAGAA<br>GCCGGGGAGCTCGGTGAAAGTGTCCTGCAAGGCCTCCG<br>GGGGAACTTTCAGCTCCCACTACATCAACTGGGTCAGA<br>CAGGCGCCCGGACAGGGGTTGGAATGGATGGGCGGAAT<br>CATCCCGGCGTTTGGCGGCGCGAACTACGCCCAGAAGT<br>TCCAGGGTCGGGTCACCATTACCGCCGACGAGTCCACT<br>TCCACTGCATACATGGAGCTGTCCTCACTGCGGAGCGA<br>AGATACCGCCGTGTATTACTGCGCCCGCTTCGGATCTG<br>TGTACGTGTCCCGCTACTCCTCATACTACCATATGGAC<br>GTCTGGGGACAGGGCACCCTGGTCACGGTGTCGTCCGC<br>TAGCACCAAGGGCCCAAGTGTGTTTCCCCTGGCCCCCAG<br>CAGCAAGTCTACTTCCGGCGGAACTGCTGCCCTGGGTT<br>GCCTGGTGAAGGACTACTTCCCCGAGCCCGTGACAGTG<br>TCCTGGAACTCTGGGGCTCTGACTTCCGGCGTGCACACC<br>TTCCCCGCCGTGCTGCAGAGCAGCGGCCTGTACAGCCTG<br>AGCAGCGTGGTGACAGTGCCCTCCAGCTCTCTGGGAAC<br>CCAGACCTATATCTGCAACGTGAACCACAAGCCCAGCA<br>ACACCAAGGTGGACAAGAGAGTGGAGCCCAAGAGCTGC<br>GACAAGACCCACACCTGCCCCCCCTGCCCAGCTCCAGAA<br>CTGCTGGGAGGGCCTTCCGTGTTCCTGTTCCCCCCCAAG<br>CCCAAGGACACCCTGATGATCAGCAGGACCCCCGAGGT<br>GACCTGCGTGGTGGTGGACGTGTCCCACGAGGACCCAG<br>AGGTGAAGTTCAACTGGTACGTGGACGGCGTGGAGGTG<br>CACAACGCCAAGACCAAGCCCAGAGAGGAGCAGTACAA<br>CAGCACCTACAGGGTGGTGTCCGTGCTGACCGTGCTGC<br>ACCAGGACTGGCTGAACGGCAAAGAATACAAGTGCAAA<br>GTCTCCAACAAGGCCCTGCCAGCCCCAATCGAAAAGAC<br>AATCAGCAAGGCCAAGGGCCAGCCACGGGAGCCCCAGG<br>TGTACACCCTGCCCCCCAGCCGGGAGGAGATGACCAAG<br>AACCAGGTGTCCCTGACCTGTCTGGTGAAGGGCTTCTA<br>CCCCAGCGATATCGCCGTGGAGTGGGAGAGCAACGGCC<br>AGCCCGAGAACAACTACAAGACCACCCCCCCAGTGCTG<br>GACAGCGACGGCAGCTTCTTCCTGTACAGCAAGCTGAC<br>CGTGGACAAGTCCAGGTGGCAGCAGGGCAACGTGTTCA<br>GCTGCAGCGTGATGCACGAGGCCCTGCACAACCACTAC<br>ACCCAGAAGTCCCTGAGCCTGAGCCCCGGCAAG |
| SEQ ID NO: 42 | LCDR1 (Combined) | RASQTIYRSLA |
| SEQ ID NO: 43 | LCDR2 (Combined) | GASILQS |
| SEQ ID NO: 44 | LCDR3 (Combined) | LQRYTSPFT |
| SEQ ID NO: 45 | LCDR1 (Kabat) | RASQTIYRSLA |
| SEQ ID NO: 46 | LCDR2 (Kabat) | GASILQS |
| SEQ ID NO: 47 | LCDR3 (Kabat) | LQRYTSPFT |
| SEQ ID NO: 48 | LCDR1 (Chothia) | SQTIYRS |
| SEQ ID NO: 49 | LCDR2 (Chothia) | GAS |
| SEQ ID NO: 50 | LCDR3 (Chothia) | RYTSPF |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| SEQ ID NO: 51 | VL | DIQMTQSPSSLSASVGDRVTITCRASQTIYRSLAWYQQK PGKAPKLLIYGASILQSGVPSRFSGSGSGTDFTLTISSLQP EDFATYYCLQRYTSPFTFGQGTKVEIK |
| SEQ ID NO: 52 | DNA VL | GACATTCAGATGACCCAGTCACCCTCCTCTCTCTCCGCA TCCGTGGGCGATCGCGTGACCATCACCTGTCGGGCCAG CCAGACCATCTATAGAAGCCTGGCCTGGTACCAGCAGA AACCGGGAAAGGCCCCAAAGCTGCTGATCTACGGCGCC AGCATTCTGCAGTCCGGGGTGCCTTCGAGGTTCTCCGG ATCCGGGTCGGGAACTGACTTCACCTTGACCATCTCGA GCCTGCAGCCGGAGGACTTCGCGACTTACTACTGCCTG CAACGGTACACCTCACCCTTTACCTTCGGACAAGGCAC AAAGGTCGAAATCAAG |
| SEQ ID NO: 53 | Light Chain | DIQMTQSPSSLSASVGDRVTITCRASQTIYRSLAWYQQK PGKAPKLLIYGASILQSGVPSRFSGSGSGTDFTLTISSLQP EDFATYYCLQRYTSPFTFGQGTKVEIKRTVAAPSVFIFPP SDEQLKSGTASVVCLLNNFYPREAKVQWKVDNALQSGN SQESVTEQDSKDSTYSLSSTLTLSKADYEKHKVYACEVT HQGLSSPVTKSFNRGEC |
| SEQ ID NO: 54 | DNA Light Chain | GACATTCAGATGACCCAGTCACCCTCCTCTCTCTCCGCA TCCGTGGGCGATCGCGTGACCATCACCTGTCGGGCCAG CCAGACCATCTATAGAAGCCTGGCCTGGTACCAGCAGA AACCGGGAAAGGCCCCAAAGCTGCTGATCTACGGCGCC AGCATTCTGCAGTCCGGGGTGCCTTCGAGGTTCTCCGG ATCCGGGTCGGGAACTGACTTCACCTTGACCATCTCGA GCCTGCAGCCGGAGGACTTCGCGACTTACTACTGCCTG CAACGGTACACCTCACCCTTTACCTTCGGACAAGGCAC AAAGGTCGAAATCAAGCGTACGGTGGCCGCTCCCAGCG TGTTCATCTTCCCCCCCAGCGACGAGCAGCTGAAGAGC GGCACCGCCAGCGTGGTGTGCCTGCTGAACAACTTCTA CCCCCGGGAGGCCAAGGTGCAGTGGAAGGTGGACAACG CCCTGCAGAGCGGCAACAGCCAGGAGAGCGTCACCGAG CAGGACAGCAAGGACTCCACCTACAGCCTGAGCAGCAC CCTGACCCTGAGCAAGGCCGACTACGAGAAGCATAAGG TGTACGCCTGCGAGGTGACCCACCAGGGCCTGTCCAGC CCGTGACCAAGAGCTTCAACAGGGGCGAGTGC |
| ABGDF15-B | | |
| SEQ ID NO: 55 | HCDR1 (Combined) | GGTFRSYAVS |
| SEQ ID NO: 56 | HCDR2 (Combined) | GIIPIFGTANYAQKFQG |
| SEQ ID NO: 57 | HCDR3 (Combined) | GPIIMGYQFGLFDH |
| SEQ ID NO: 58 | HCDR1 (Kabat) | SYAVS |
| SEQ ID NO: 59 | HCDR2 (Kabat) | GIIPIFGTANYAQKFQG |
| SEQ ID NO: 60 | HCDR3 (Kabat) | GPIIMGYQFGLFDH |
| SEQ ID NO: 61 | HCDR1 (Chothia) | GGTFRSY |
| SEQ ID NO: 62 | HCDR2 (Chothia) | IPIFGT |
| SEQ ID NO: 63 | HCDR3 (Chothia) | GPIIMGYQFGLFDH |
| SEQ ID NO: 64 | VH | QVQLVQSGAEVKKPGSSVKVSCKASGGTFRSYAVSWVR QAPGQGLEWMGGIIPIFGTANYAQKFQGRVTITADESTS TAYMELSSLRSEDTAVYYCARGPIIMGYQFGLFDHWGQ GTLVTVSS |
| SEQ ID NO: 65 | DNA VH | CAAGTGCAACTCGTGCAGTCGGGGGCCGAGGTCAAGAA GCCCGGCTCGTCCGTGAAAGTGTCCTGCAAGGCCTCCG GAGGAACTTTCCGGTCATACGCCGTGTCCTGGGTCCAGA CAGGCCCCAGGACAGGGATTGGAGTGGATGGGAGGCAT CATCCCGATTTTTGGCACCGCGAACTACGCCCAGAAGT TCCAGGGCCGCGTGACCATCACTGCCGACGAAAGCACC TCCACGGCATACATGGAACTGTCAAGCCTGCGGTCCGA AGATACCGCGGTGTACTATTGCGCAAGGGGGTCCGATTA |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | TCATGGGGTACCAGTTCGGGCTGTTCGACCACTGGGGA CAGGGAACCCTGGTCACTGTGTCGTCC |
| SEQ ID NO: 66 | Heavy Chain | QVQLVQSGAEVKKPGSSVKVSCKASGGTFRSYAVSWVR QAPGQGLEWMGGIIPIFGTANYAQKFQGRVTITADESTS TAYMELSSLRSEDTAVYYCARGPIIMGYQFGLFDHWGQ GTLVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDV SHEDPEVKFNWYVDGVEVHNAKTKPREEQYNSTYRVV SVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRWQ QGNVFSCSVMHEALHNHYTQKSLSLSPGK |
| SEQ ID NO: 67 | DNA Heavy Chain | CAAGTGCAACTCGTGCAGTCGGGGGCCGAGGTCAAGAA GCCCGGCTCGTCCGTGAAAGTGTCCTGCAAGGCCTCCG GAGGAACTTTCCGGTCATACGCCGTGTCCTGGGTCAGA CAGGCCCCAGGACAGGGATTGGAGTGGATGGGAGGCAT CATCCCGATTTTTGGCACCGCGAACTACGCCCAGAAGT TCCAGGGCCGCGTGACCATCACTGCCGACGAAAGCACC TCCACGGCATACATGGAACTGTCAAGCCTGCGGTCCGA AGATACCGCGGTGTACTATTGCGCAAGGGGTCCGATTA TCATGGGGTACCAGTTCGGGCTGTTCGACCACTGGGGA CAGGGAACCCTGGTCACTGTGTCGTCCGCTAGCACCAA GGGCCCAAGTGTGTTTCCCCTGGCCCCCAGCAGCAAGTC TACTTCCGGCGGAACTGCTGCCCTGGGTTGCCTGGTGA AGGACTACTTCCCCGAGCCCGTGACAGTGTCCTGGAAC TCTGGGGCTCTGACTTCCGGCGTGCACACCTTCCCCGCC GTGCTGCAGAGCAGCGGCCTGTACAGCCTGAGCAGCGT GGTGACAGTGCCCTCCAGCTCTCTGGGAACCCAGACCT ATATCTGCAACGTGAACCACAAGCCCAGCAACACCAAG GTGGACAAGAGAGTGGAGCCCAAGAGCTGCGACAAGAC CCACACCTGCCCCCCCTGCCCAGCTCCAGAACTGCTGGG AGGGCCTTCCGTGTTCCTGTTCCCCCCCAAGCCCAAGGA CACCCTGATGATCAGCAGGACCCCCGAGGTGACCTGCG TGGTGGTGGACGTGTCCCACGAGGACCCAGAGGTGAAG TTCAACTGGTACGTGGACGGCGTGGAGGTGCACAACGC CAAGACCAAGCCCAGAGAGGAGCAGTACAACAGCACCT ACAGGGTGGTGTCCGTGCTGACCGTGCTGCACCAGGAC TGGCTGAACGGCAAAGAATACAAGTGCAAAGTCTCCAA CAAGGCCCTGCCAGCCCCAATCGAAAAGACAATCAGCA AGGCCAAGGGCCAGCCACGGGAGCCCCAGGTGTACACC CTGCCCCCAGCCGGGAGGAGATGACCAAGAACCAGGT GTCCCTGACCTGTCTGGTGAAGGGCTTCTACCCCAGCG ATATCGCCGTGGAGTGGGAGAGCAACGGCCAGCCCGAG AACAACTACAAGACCACCCCCCCAGTGCTGGACAGCGA CGGCAGCTTCTTCCTGTACAGCAAGCTGACCGTGGACA AGTCCAGGTGGCAGCAGGGCAACGTGTTCAGCTGCAGC GTGATGCACGAGGCCCTGCACAACCACTACACCCAGAA GTCCCTGAGCCTGAGCCCCGGCAAG |
| SEQ ID NO: 68 | LCDR1 (Combined) | SGDNIGSHIVS |
| SEQ ID NO: 69 | LCDR2 (Combined) | DKSNRPS |
| SEQ ID NO: 70 | LCDR3 (Combined) | QTWDSIGSVV |
| SEQ ID NO: 71 | LCDR1 (Kabat) | SGDNIGSHIVS |
| SEQ ID NO: 72 | LCDR2 (Kabat) | DKSNRPS |
| SEQ ID NO: 73 | LCDR3 (Kabat) | QTWDSIGSVV |
| SEQ ID NO: 74 | LCDR1 (Chothia) | DNIGSHI |
| SEQ ID NO: 75 | LCDR2 (Chothia) | DKS |
| SEQ ID NO: 76 | LCDR3 (Chothia) | WDSIGSV |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
| --- | --- | --- |
| SEQ ID NO: 77 | VL | SYELTQPLSVSVALGQTARITCSGDNIGSHIVSWYQQKPG QAPVLVIYDKSNRPSGIPERFSGSNSGNTATLTISRAQAG DEADYYCQTWDSIGSVVFGGGTKLTVL |
| SEQ ID NO: 78 | DNA VL | TCATATGAACTCACCCAACCCCTGTCCGTGTCCGTGGCC CTGGGTCAGACTGCCCGGATTACCTGTTCGGGAGACAA CATCGGAAGCCACATCGTGTCGTGGTACCAGCAGAAAC CCGGCCAGGCGCCAGTGCTGGTCATCTACGATAAGTCC AACCGCCCGTCCGGAATCCCGGAGAGGTTCAGCGGGTC CAATAGCGGCAACACCGCAACCCTGACCATCTCAAGAG CTCAGGCCGGGGATGAGGCCGACTACTACTGCCAAACT TGGGACTCGATTGGCTCCGTGGTGTTCGGCGGCGGAAC TAAGCTCACGGTCCTG |
| SEQ ID NO: 79 | Light Chain | SYELTQPLSVSVALGQTARITCSGDNIGSHIVSWYQQKPG QAPVLVIYDKSNRPSGIPERFSGSNSGNTATLTISRAQAG DEADYYCQTWDSIGSVVFGGGTKLTVLGQPKAAPSVTL FPPSSEELQANKATLVCLISDFYPGAVTVAWKADSSPVK AGVETTTPSKQSNNKYAASSYLSLTPEQWKSHRSYSCQ VTHEGSTVEKTVAPTECS |
| SEQ ID NO: 80 | DNA Light Chain | TCATATGAACTCACCCAACCCCTGTCCGTGTCCGTGGCC CTGGGTCAGACTGCCCGGATTACCTGTTCGGGAGACAA CATCGGAAGCCACATCGTGTCGTGGTACCAGCAGAAAC CCGGCCAGGCGCCAGTGCTGGTCATCTACGATAAGTCC AACCGCCCGTCCGGAATCCCGGAGAGGTTCAGCGGGTC CAATAGCGGCAACACCGCAACCCTGACCATCTCAAGAG CTCAGGCCGGGGATGAGGCCGACTACTACTGCCAAACT TGGGACTCGATTGGCTCCGTGGTGTTCGGCGGCGGAAC TAAGCTCACGGTCCTGGGTCAGCCTAAGGCTGCCCCCA GCGTGACCCTGTTCCCCCCCAGCAGCGAGGAGCTGCAG GCCAACAAGGCCACCCTGGTGTGCCTGATCAGCGACTT CTACCCAGGCGCCGTGACCGTGGCCTGGAAGGCCGACA GCAGCCCCGTGAAGGCCGGCGTGGAGACCACCACCCCA GCAAGCAGAGCAACAACAAGTACGCCGCCAGCAGCTAC CTGAGCCTGACCCCCGAGCAGTGGAAGAGCCACAGGTC CTACAGCTGCCAGGTGACCCACGAGGGCAGCACCGTGG AAAAGACCGTGGCCCCAACCGAGTGCAGC |
| ABGDF15-C | | |
| SEQ ID NO: 81 | HCDR1 (Combined) | GGTFRSYAVS |
| SEQ ID NO: 82 | HCDR2 (Combined) | GIIPIFGTANYAQKFQG |
| SEQ ID NO: 83 | HCDR3 (Combined) | GPIIMGYQFGLFDH |
| SEQ ID NO: 84 | HCDR1 (Kabat) | SYAVS |
| SEQ ID NO: 85 | HCDR2 (Kabat) | GIIPIFGTANYAQKFQG |
| SEQ ID NO: 86 | HCDR3 (Kabat) | GPIIMGYQFGLFDH |
| SEQ ID NO: 87 | HCDR1 (Chothia) | GGTFRSY |
| SEQ ID NO: 88 | HCDR2 (Chothia) | IPIFGT |
| SEQ ID NO: 89 | HCDR3 (Chothia) | GPIIMGYQFGLFDH |
| SEQ ID NO: 90 | VH | QVQLVQSGAEVKKPGSSVKVSCKASGGTFRSYAVSWVR QAPGQGLEWMGGIIPIFGTANYAQKFQGRVTITADESTS TAYMELSSLRSEDTAVYYCARGPIIMGYQFGLFDHWGQ GTLVTVSS |
| SEQ ID NO: 91 | DNA VH | CAAGTGCAACTCGTGCAGTCGGGGGCCGAGGTCAAGAA GCCCGGCTCGTCCGTGAAAGTGTCCTGCAAGGCCTCCG GAGGAACTTTCCGGTCATACGCCGTGTCCTGGGTCAGA CAGGCCCCAGGACAGGGATTGGAGTGGATGGGAGGCAT CATCCCGATTTTTGGCACCGCGAACTACGCCCAGAAGT TCCAGGGCCGCGTGACCATCACTGCCGACGAAAGCACC TCCACGGCATACATGGAACTGTCAAGCCTGCGGTCCGA AGATACCGCGGTGTACTATTGCGCAAGGGGTCCGATTA |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | TCATGGGGTACCAGTTCGGGCTGTTCGACCACTGGGGA<br>CAGGGAACCCTGGTCACTGTGTCGTCC |
| SEQ ID NO: 92 | Heavy Chain | QVQLVQSGAEVKKPGSSVKVSCKASGGTFRSYAVSWVR<br>QAPGQGLEWMGGIIPIFGTANYAQKFQGRVTITADESTS<br>TAYMELSSLRSEDTAVYYCARGPIIMGYQFGLFDHWGQ<br>GTLVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKRVEPKSCDKTHTCP<br>PCPAPELLGGPSVFLFPPKPKDTLMISRTPEVTCVVVDV<br>SHEDPEVKFNWYVDGVEVHNAKTKPREEQYNSTYRVV<br>SVLTVLHQDWLNGKEYKCKVSNKALPAPIEKTISKAKG<br>QPREPQVYTLPPSREEMTKNQVSLTCLVKGFYPSDIAVE<br>WESNGQPENNYKTTPPVLDSDGSFFLYSKLTVDKSRWQ<br>QGNVFSCSVMHEALHNHYTQKSLSLSPGK |
| SEQ ID NO: 93 | DNA Heavy Chain | CAAGTGCAACTCGTGCAGTCGGGGGCCGAGGTCAAGAA<br>GCCCGGCTCGTCCGTGAAAGTGTCCTGCAAGGCCTCCG<br>GAGGAACTTTCCGGTCATACGCCGTGTCCTGGGTCAGA<br>CAGGCCCCAGGACAGGGATTGGAGTGGATGGGAGGCAT<br>CATCCCGATTTTTGGCACCGCGAACTACGCCCAGAAGT<br>TCCAGGGCCGCGTGACCATCACTGCCGACGAAAGCACC<br>TCCACGGCATACATGGAACTGTCAAGCCTGCGGTCCGA<br>AGATACCGCGGTGTACTATTGCGCAAGGGGTCCGATTA<br>TCATGGGGTACCAGTTCGGGCTGTTCGACCACTGGGGA<br>CAGGGAACCCTGGTCACTGTGTCGTCCGCTAGCACCAA<br>GGGCCCAAGTGTGTTTCCCCTGGCCCCCAGCAGCAAGTC<br>TACTTCCGGCGGAACTGCTGCCCTGGGTTGCCTGGTGA<br>AGGACTACTTCCCCGAGCCCGTGACAGTGTCCTGGAAC<br>TCTGGGGCTCTGACTTCCGGCGTGCACACCTTCCCCGCC<br>GTGCTGCAGAGCAGCGGCCTGTACAGCCTGAGCAGCGT<br>GGTGACAGTGCCCTCCAGCTCTCTGGGAACCCAGACCT<br>ATATCTGCAACGTGAACCACAAGCCCAGCAACACCAAG<br>GTGGACAAGAGAGTGGAGCCCAAGAGCTGCGACAAGAC<br>CCACACCTGCCCCCCCTGCCCAGCTCCAGAACTGCTGGG<br>AGGGCCTTCCGTGTTCCTGTTCCCCCCCAAGCCCAAGGA<br>CACCCTGATGATCAGCAGGACCCCCGAGGTGACCTGCG<br>TGGTGGTGGACGTGTCCCACGAGGACCCAGAGGTGAAG<br>TTCAACTGGTACGTGGACGGCGTGGAGGTGCACAACGC<br>CAAGACCAAGCCCAGAGAGGAGCAGTACAACAGCACCT<br>ACAGGGTGGTGTCCGTGCTGACCGTGCTGCACCAGGAC<br>TGGCTGAACGGCAAAGAATACAAGTGCAAAGTCTCCAA<br>CAAGGCCCTGCCAGCCCCAATCGAAAAGACAATCAGCA<br>AGGCCAAGGGCCAGCCACGGGAGCCCCAGGTGTACACC<br>CTGCCCCCCAGCCGGGAGGAGATGACCAAGAACCAGGT<br>GTCCCTGACCTGTCTGGTGAAGGGCTTCTACCCCAGCG<br>ATATCGCCGTGGAGTGGGAGAGCAACGGCCAGCCCGAG<br>AACAACTACAAGACCACCCCCCCAGTGCTGGACAGCGA<br>CGGCAGCTTCTTCCTGTACAGCAAGCTGACCGTGGACA<br>AGTCCAGGTGGCAGCAGGGCAACGTGTTCAGCTGCAGC<br>GTGATGCACGAGGCCCTGCACAACCACTACACCCAGAA<br>GTCCCTGAGCCTGAGCCCCGGCAAG |
| SEQ ID NO: 94 | LCDR1 (Combined) | SGDNIGSHIVS |
| SEQ ID NO: 95 | LCDR2 (Combined) | DKSNRPS |
| SEQ ID NO: 96 | LCDR3 (Combined) | QTWDSIGSVV |
| SEQ ID NO: 97 | LCDR1 (Kabat) | SGDNIGSHIVS |
| SEQ ID NO: 98 | LCDR2 (Kabat) | DKSNRPS |
| SEQ ID NO: 99 | LCDR3 (Kabat) | QTWDSIGSVV |
| SEQ ID NO: 100 | LCDR1 (Chothia) | DNIGSHI |
| SEQ ID NO: 101 | LCDR2 (Chothia) | DKS |
| SEQ ID NO: 102 | LCDR3 (Chothia) | WDSIGSV |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| SEQ ID NO: 103 | VL | SYELTQPPSVSVSPGQTASITCSGDNIGSHIVSWYQQKPG QSPVLVIYDKSNRPSGIPERFSGSNSGNTATLTISGTQAM DEADYYCQTWDSIGSVVFGGGTKLTVL |
| SEQ ID NO: 104 | DNA VL | TCATACGAGCTTACCCAGCCACCTAGCGTGTCAGTCAG CCCCGGGCAGACCGCCTCCATCACTTGCTCGGGAGACAA CATCGGCTCCCACATCGTGTCGTGGTATCAGCAGAAGC CGGGCCAGTCGCCGGTGCTCGTGATCTACGACAAATCC AATCGCCCGTCCGGAATCCCCGAACGGTTCAGCGGATC CAACTCCGGAAACACTGCCACCCTGACTATTAGCGGCA CCCAAGCGATGGATGAGGCTGACTACTACTGCCAAACC TGGGATTCCATTGGGTCCGTGGTGTTCGGTGGAGGAAC GAAGCTGACCGTGCTG |
| SEQ ID NO: 105 | Light Chain | SYELTQPPSVSVSPGQTASITCSGDNIGSHIVSWYQQKPG QSPVLVIYDKSNRPSGIPERFSGSNSGNTATLTISGTQAM DEADYYCQTWDSIGSVVFGGGTKLTVLGQPKAAPSVTL FPPSSEELQANKATLVCLISDFYPGAVTVAWKADSSPVK AGVETTTPSKQSNNKYAASSYLSLTPEQWKSHRSYSCQ VTHEGSTVEKTVAPTECS |
| SEQ ID NO: 106 | DNA Light Chain | TCATACGAGCTTACCCAGCCACCTAGCGTGTCAGTCAG CCCCGGGCAGACCGCCTCCATCACTTGCTCGGGAGACAA CATCGGCTCCCACATCGTGTCGTGGTATCAGCAGAAGC CGGGCCAGTCGCCGGTGCTCGTGATCTACGACAAATCC AATCGCCCGTCCGGAATCCCCGAACGGTTCAGCGGATC CAACTCCGGAAACACTGCCACCCTGACTATTAGCGGCA CCCAAGCGATGGATGAGGCTGACTACTACTGCCAAACC TGGGATTCCATTGGGTCCGTGGTGTTCGGTGGAGGAAC GAAGCTGACCGTGCTGGGCCAGCCTAAGGCTGCCCCCA GCGTGACCCTGTTCCCCCCCAGCAGCGAGGAGCTGCAG GCCAACAAGGCCACCCTGGTGTGCCTGATCAGCGACTT CTACCCAGGCGCCGTGACCGTGGCCTGGAAGGCCGACA GCAGCCCCGTGAAGGCCGGCGTGGAGACCACCACCCCCA GCAAGCAGAGCAACAACAAGTACGCCGCCAGCAGCTAC CTGAGCCTGACCCCCGAGCAGTGAAGAGCCACAGGTC CTACAGCTGCCAGGTGACCCACGAGGGCAGCACCGTGG AAAAGACCGTGGCCCCCAACCGAGTGCAGC |

ABGDF15-D

| SEQ ID NO: 107 | HCDR1 (Combined) | GYSFTSYWIG |
| SEQ ID NO: 108 | HCDR2 (Combined) | VIDPDGSYTIYSPSFQG |
| SEQ ID NO: 109 | HCDR3 (Combined) | YGRYGTYFDY |
| SEQ ID NO: 110 | HCDR1 (Kabat) | SYWIG |
| SEQ ID NO: 111 | HCDR2 (Kabat) | VIDPDGSYTIYSPSFQG |
| SEQ ID NO: 112 | HCDR3 (Kabat) | YGRYGTYFDY |
| SEQ ID NO: 113 | HCDR1 (Chothia) | GYSFTSY |
| SEQ ID NO: 114 | HCDR2 (Chothia) | DPDGSY |
| SEQ ID NO: 115 | HCDR3 (Chothia) | YGRYGTYFDY |
| SEQ ID NO: 116 | VH | EVQLVQSGAEVKKPGESLKISCKGSGYSFTSYWIGWVRQ MPGKGLEWMGVIDPDGSYTIYSPSFQGQVTISADKSIST AYLQWSSLKASDTAMYYCARYGRYGTYFDYWGQGTLV TVSS |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
| --- | --- | --- |
| SEQ ID NO: 117 | DNA VH | GAAGTCCAACTCGTGCAGTCCGGAGCCGAGGTCAAGAAGCCCGGCGAATCGCTGAAGATTAGCTGCAAAGGCTCCGGTTACTCCTTCACCTCTTACTGGATTGGCTGGGTCCGGCAGATGCCAGGGAAGGGATTGGAGTGGATGGGAGTGATCGACCCGGACGGATCATACACCATCTACTCGCCGAGCTTTCAAGGACAGGTCACCATCTCCGCCGACAAGTCCATCTCCACTGCGTATCTGCAGTGGAGCTCACTGAAGGCCTCCGATACGGCAATGTACTACTGCGCGAGATACGGACGCTACGGGACTTACTTCGATTACTGGGGCCAGGGGACCCTCGTGACTGTGTCGTCC |
| SEQ ID NO: 118 | Heavy Chain | EVQLVQSGAEVKKPGESLKISCKGSGYSFTSYWIGWVRQMPGKGLEWMGVIDPDGSYTIYSPSFQGQVTISADKSISTAYLQWSSLKASDTAMYYCARYGRYGTYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 119 | DNA Heavy Chain | GAAGTCCAACTCGTGCAGTCCGGAGCCGAGGTCAAGAAGCCCGGCGAATCGCTGAAGATTAGCTGCAAAGGCTCCGGTTACTCCTTCACCTCTTACTGGATTGGCTGGGTCCGGCAGATGCCAGGGAAGGGATTGGAGTGGATGGGAGTGATCGACCCGGACGGATCATACACCATCTACTCGCCGAGCTTTCAAGGACAGGTCACCATCTCCGCCGACAAGTCCATCTCCACTGCGTATCTGCAGTGGAGCTCACTGAAGGCCTCCGATACGGCAATGTACTACTGCGCGAGATACGGACGCTACGGGACTTACTTCGATTACTGGGGCCAGGGGACCCTCGTGACTGTGTCGTCCGCTAGCACCAAGGGCCCAAGTGTGTTTCCCCTGGCCCCCAGCAGCAAGTCTACTTCCGGCGGAACTGCTGCCCTGGGTTGCCTGGTGAAGGACTACTTCCCCGAGCCCGTGACAGTGTCCTGGAACTCTGGGGCTCTGACTTCCGGCGTGCACACCTTCCCCGCCGTGCTGCAGAGCAGCGGCCTGTACAGCCTGAGCAGCGTGGTGACAGTGCCCTCCAGCTCTCTGGGAACCCAGACCTATATCTGCAACGTGAACCACAAGCCCAGCAACACCAAGGTGGACAAGAGAGTGGAGCCCAAGAGCTGCGACAAGACCCACACCTGCCCCCCCTGCCCAGCTCCAGAACTGCTGGGAGGGCCTTCCGTGTTCCTGTTCCCCCCCAAGCCCAAGGACACCCTGATGATCAGCAGGACCCCCGAGGTGACCTGCGTGGTGGTGGACGTGTCCCACGAGGACCCAGAGGTGAAGTTCAACTGGTACGTGGACGGCGTGGAGGTGCACAACGCCAAGACCAAGCCCAGAGAGGAGCAGTACAACAGCACCTACAGGGTGGTGTCCGTGCTGACCGTGCTGCACCAGGACTGGCTGAACGGCAAAGAATACAAGTGCAAAGTCTCCAACAAGGCCCTGCCAGCCCCAATCGAAAAGACAATCAGCAAGGCCAAGGGCCAGCCACGGGAGCCCCAGGTGTACACCCTGCCCCCCAGCCGGGAGGAGATGACCAAGAACCAGGTGTCCCTGACCTGTCTGGTGAAGGGCTTCTACCCCAGCGATATCGCCGTGGAGTGGGAGAGCAACGGCCAGCCCGAGAACAACTACAAGACCACCCCCCCAGTGCTGGACAGCGACGGCAGCTTCTTCCTGTACAGCAAGCTGACCGTGGACAAGTCCAGGTGGCAGCAGGGCAACGTGTTCAGCTGCAGCGTGATGCACGAGGCCCTGCACAACCACTACACCCAGAAGTCCCTGAGCCTGAGCCCCGGCAAG |
| SEQ ID NO: 120 | LCDR1 (Combined) | SGSSSNIGVLYVN |
| SEQ ID NO: 121 | LCDR2 (Combined) | SNDNRPS |
| SEQ ID NO: 122 | LCDR3 (Combined) | QSWDSSSNYV |
| SEQ ID NO: 123 | LCDR1 (Kabat) | SGSSSNIGVLYVN |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
| --- | --- | --- |
| SEQ ID NO: 124 | LCDR2 (Kabat) | SNDNRPS |
| SEQ ID NO: 125 | LCDR3 (Kabat) | QSWDSSSNYV |
| SEQ ID NO: 126 | LCDR1 (Chothia) | SSSNIGVLY |
| SEQ ID NO: 127 | LCDR2 (Chothia) | SND |
| SEQ ID NO: 128 | LCDR3 (Chothia) | WDSSSNY |
| SEQ ID NO: 129 | VL | QSVLTQPPSVSGAPGQRVTISCSGSSSNIGVLYVNWYQQ LPGTAPKLLIYSNDNRPSGVPDRFSGSKSGTSASLAITGL QAEDEADYYCQSWDSSSNYVFGGGTKLTVL |
| SEQ ID NO: 130 | DNA VL | CAATCGGTGCTGACCCAGCCCCCTTCGGTGTCCGGAGCC CCGGGGCCAGAGAGTGACCATCAGCTGCTCGGGTTCCTC TAGCAACATCGGGGTGCTCTACGTGAACTGGTACCAGC AGCTGCCGGGCACCGCCCCAAAGCTGCTGATCTATAGC AATGATAACCGGCCGTCCGGAGTGCCCGACCGGTTCTC CGGATCAAAGAGCGGCACCTCCGCATCCTTGGCCATTA CGGGGCTGCAGGCGGAGGACGAAGCTGATTACTACTGT CAATCGTGGGACTCCTCATCCAACTACGTGTTCGGCGG AGGCACCAAACTGACTGTCCTG |
| SEQ ID NO: 131 | Light Chain | QSVLTQPPSVSGAPGQRVTISCSGSSSNIGVLYVNWYQQ LPGTAPKLLIYSNDNRPSGVPDRFSGSKSGTSASLAITGL QAEDEADYYCQSWDSSSNYVFGGGTKLTVLGQPKAAPS VTLFPPSSEELQANKATLVCLISDFYPGAVTVAWKADSS PVKAGVETTTPSKQSNNKYAASSYLSLTPEQWKSHRSY SCQVTHEGSTVEKTVAPTECS |
| SEQ ID NO: 132 | DNA Light Chain | CAATCGGTGCTGACCCAGCCCCCTTCGGTGTCCGGAGCC CCGGGGCCAGAGAGTGACCATCAGCTGCTCGGGTTCCTC TAGCAACATCGGGGTGCTCTACGTGAACTGGTACCAGC AGCTGCCGGGCACCGCCCCAAAGCTGCTGATCTATAGC AATGATAACCGGCCGTCCGGAGTGCCCGACCGGTTCTC CGGATCAAAGAGCGGCACCTCCGCATCCTTGGCCATTA CGGGGCTGCAGGCGGAGGACGAAGCTGATTACTACTGT CAATCGTGGGACTCCTCATCCAACTACGTGTTCGGCGG AGGCACCAAACTGACTGTCCTGGGTCAGCCTAAGGCTG CCCCCAGCGTGACCCTGTTCCCCCCCAGCAGCGAGGAGC TGCAGGCCAACAAGGCCACCCTGGTGTGCCTGATCAGC GACTTCTACCCAGGCGCCGTGACCGTGGCCTGGAAGGC CGACAGCAGCCCCGTGAAGGCCGGCGTGGAGACCACCA CCCCCAGCAAGCAGAGCAACAACAAGTACGCCGCCAGC AGCTACCTGAGCCTGACCCCCGAGCAGTGGAAGAGCCA CAGGTCCTACAGCTGCCAGGTGACCCACGAGGGCAGCA CCGTGGAAAAGACCGTGGCCCCAACCGAGTGCAGC |

ABGDF15-E

| SEQ ID NO: 133 | HCDR1 (Combined) | GYSFTSYWIG |
| --- | --- | --- |
| SEQ ID NO: 134 | HCDR2 (Combined) | VIDPGGSYTIYSPSFQG |
| SEQ ID NO: 135 | HCDR3 (Combined) | YGRYGTYFDY |
| SEQ ID NO: 136 | HCDR1 (Kabat) | SYVVIG |
| SEQ ID NO: 137 | HCDR2 (Kabat) | VIDPGGSYTIYSPSFQG |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| SEQ ID NO: 138 | HCDR3 (Kabat) | YGRYGTYFDY |
| SEQ ID NO: 139 | HCDR1 (Chothia) | GYSFTSY |
| SEQ ID NO: 140 | HCDR2 (Chothia) | DPGGSY |
| SEQ ID NO: 141 | HCDR3 (Chothia) | YGRYGTYFDY |
| SEQ ID NO: 142 | VH | EVQLVQSGAEVKKPGESLKISCKGSGYSFTSYWIGWVRQ MPGKGLEWMGVIDPGGSYTIYSPSFQGQVTISADKSIST AYLQWSSLKASDTAMYYCARYGRYGTYFDYWGQGTLV TVSS |
| SEQ ID NO: 143 | DNA VH | GAAGTGCAACTCGTGCAGTCCGGAGCCGAGGTCAAGAA GCCCGGAGAGTCCCTGAAGATCAGCTGCAAAGGATCCG GCTACTCCTTCACTTCATACTGGATCGGTTGGGTCCGG CAGATGCCGGGAAAGGGGCTGGAATGGATGGGCGTGAT TGACCCCGGGGGCTCCTACACGATCTACTCCCCGTCGTT CCAAGGACAGGTCACCATTTCGGCCGATAAGAGCATCT CCACTGCGTATCTGCAGTGGTCAAGCCTGAAGGCCTCT GACACCGCAATGTACTACTGCGCGAGATACGGCCGCTA CGGGACTTACTTTGACTACTGGGGACAGGGTACCCTCG TGACCGTGTCCTCG |
| SEQ ID NO: 144 | Heavy Chain | EVQLVQSGAEVKKPGESLKISCKGSGYSFTSYWIGWVRQ MPGKGLEWMGVIDPGGSYTIYSPSFQGQVTISADKSIST AYLQWSSLKASDTAMYYCARYGRYGTYFDYWGQGTLV TVSSASTKGPSVFPLAPSSKSTSGGTAALGCLVKDYFPEP VTVSWNSGALTSGVHTFPAVLQSSGLYSLSSVVTVPSSSL GTQTYICNVNHKPSNTKVDKRVEPKSCDKTHTCPPCPA PELLGGPSVFLFPPKPKDTLMISRTPEVTCVVVDVSHED PEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 145 | DNA Heavy Chain | GAAGTGCAACTCGTGCAGTCCGGAGCCGAGGTCAAGAA GCCCGGAGAGTCCCTGAAGATCAGCTGCAAAGGATCCG GCTACTCCTTCACTTCATACTGGATCGGTTGGGTCCGG CAGATGCCGGGAAAGGGGCTGGAATGGATGGGCGTGAT TGACCCCGGGGGCTCCTACACGATCTACTCCCCGTCGTT CCAAGGACAGGTCACCATTTCGGCCGATAAGAGCATCT CCACTGCGTATCTGCAGTGGTCAAGCCTGAAGGCCTCT GACACCGCAATGTACTACTGCGCGAGATACGGCCGCTA CGGGACTTACTTTGACTACTGGGGACAGGGTACCCTCG TGACCGTGTCCTCGGCTAGCACCAAGGGCCCAAGTGTG TTTCCCCTGGCCCCCAGCAGCAAGTCTACTTCCGGCGGA ACTGCTGCCCTGGGTTGCCTGGTGAAGGACTACTTCCC CGAGCCCGTGACAGTGTCCTGGAACTCTGGGGCTCTGA CTTCCGGCGTGCACACCTTCCCCGCCGTGCTGCAGAGCA GCGGCCTGTACAGCCTGAGCAGCGTGGTGACAGTGCCC TCCAGCTCTCTGGGAACCCAGACCTATATCTGCAACGT GAACCACAAGCCCAGCAACACCAAGGTGGACAAGAGAG TGGAGCCCAAGAGCTGCGACAAGACCCACACCTGCCCC CCTGCCCAGCTCCAGAACTGCTGGGAGGGCCTTCCGTGT TCCTGTTCCCCCCCAAGCCCAAGGACACCCTGATGATCA GCAGGACCCCCGAGGTGACCTGCGTGGTGGTGGACGTG TCCCACGAGGACCCAGAGGTGAAGTTCAACTGGTACGT GGACGGCGTGGAGGTGCACAACGCCAAGACCAAGCCCA GAGAGGAGCAGTACAACAGCACCTACAGGGTGGTGTCC GTGCTGACCGTGCTGCACCAGGACTGGCTGAACGGCAA AGAATACAAGTGCAAAGTCTCCAACAAGGCCCTGCCAG CCCCAATCGAAAAGACAATCAGCAAGGCCAAGGGCCAG CCACGGGAGCCCCAGGTGTACACCCTGCCCCCCAGCCGG GAGGAGATGACCAAGAACCAGGTGTCCCTGACCTGTCT GGTGAAGGGCTTCTACCCCAGCGATATCGCCGTGGAGT GGGAGAGCAACGGCCAGCCCGAGAACAACTACAAGACC |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | ACCCCCCCAGTGCTGGACAGCGACGGCAGCTTCTTCCTG<br>TACAGCAAGCTGACCGTGGACAAGTCCAGGTGGCAGCA<br>GGGCAACGTGTTCAGCTGCAGCGTGATGCACGAGGCCC<br>TGCACAACCACTACACCCAGAAGTCCCTGAGCCTGAGC<br>CCCGGCAAG |
| SEQ ID NO: 146 | LCDR1 (Combined) | SGSSSNIGVLYVN |
| SEQ ID NO: 147 | LCDR2 (Combined) | SNDNRPS |
| SEQ ID NO: 148 | LCDR3 (Combined) | QSWDSSSNYV |
| SEQ ID NO: 149 | LCDR1 (Kabat) | SGSSSNIGVLYVN |
| SEQ ID NO: 150 | LCDR2 (Kabat) | SNDNRPS |
| SEQ ID NO: 151 | LCDR3 (Kabat) | QSWDSSSNYV |
| SEQ ID NO: 152 | LCDR1 (Chothia) | SSSNIGVLY |
| SEQ ID NO: 153 | LCDR2 (Chothia) | SND |
| SEQ ID NO: 154 | LCDR3 (Chothia) | WDSSSNY |
| SEQ ID NO: 155 | VL | QSVLTQPPSVSGAPGQRVTISCSGSSSNIGVLYVNWYQQ<br>LPGTAPKLLIYSNDNRPSGVPDRFSGSKSGTSASLAITGL<br>QAEDEADYYCQSWDSSSNYVFGGGTKLTVL |
| SEQ ID NO: 156 | DNA VL | CAATCGGTGCTGACCCAGCCCCCTTCGGTGTCCGGAGCC<br>CCGGGGCCAGAGAGTGACCATCAGCTGCTCGGGTTCCTC<br>TAGCAACATCGGGGTGCTCTACGTGAACTGGTACCAGC<br>AGCTGCCGGGCACCGCCCCAAAGCTGCTGATCTATAGC<br>AATGATAACCGGCCGTCCGGAGTGCCCGACCGGTTCTC<br>CGGATCAAAGAGCGGCACCTCCGCATCCTTGGCCATTA<br>CGGGGCTGCAGGCGGAGGACGAAGCTGATTACTACTGT<br>CAATCGTGGGACTCCTCATCCAACTACGTGTTCGGCGG<br>AGGCACCAAACTGACTGTCCTG |
| SEQ ID NO: 157 | Light Chain | QSVLTQPPSVSGAPGQRVTISCSGSSSNIGVLYVNWYQQ<br>LPGTAPKLLIYSNDNRPSGVPDRFSGSKSGTSASLAITGL<br>QAEDEADYYCQSWDSSSNYVFGGGTKLTVLGQPKAAPS<br>VTLFPPSSEELQANKATLVCLISDFYPGAVTVAWKADSS<br>PVKAGVETTTPSKQSNNKYAASSYLSLTPEQWKSHRSY<br>SCQVTHEGSTVEKTVAPTECS |
| SEQ ID NO: 158 | DNA Light Chain | CAATCGGTGCTGACCCAGCCCCCTTCGGTGTCCGGAGCC<br>CCGGGGCCAGAGAGTGACCATCAGCTGCTCGGGTTCCTC<br>TAGCAACATCGGGGTGCTCTACGTGAACTGGTACCAGC<br>AGCTGCCGGGCACCGCCCCAAAGCTGCTGATCTATAGC<br>AATGATAACCGGCCGTCCGGAGTGCCCGACCGGTTCTC<br>CGGATCAAAGAGCGGCACCTCCGCATCCTTGGCCATTA<br>CGGGGCTGCAGGCGGAGGACGAAGCTGATTACTACTGT<br>CAATCGTGGGACTCCTCATCCAACTACGTGTTCGGCGG<br>AGGCACCAAACTGACTGTCCTGGGTCAGCCTAAGGCTG<br>CCCCCAGCGTGACCCTGTTCCCCCCCAGCAGCGAGGAGC<br>TGCAGGCCAACAAGGCCACCCTGGTGTGCCTGATCAGC<br>GACTTCTACCCAGGCGCCGTGACCGTGGCCTGGAAGGC<br>CGACAGCAGCCCCGTGAAGGCCGGCGTGGAGACCACCA<br>CCCCCAGCAAGCAGAGCAACAACAAGTACGCCGCCAGC<br>AGCTACCTGAGCCTGACCCCCGAGCAGTGGAAGAGCCA<br>CAGGTCCTACAGCTGCCAGGTGACCCACGAGGGCAGCA<br>CCGTGGAAAAGACCGTGGCCCCAACCGAGTGCAGC |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| ABGDF15-F | | |
| SEQ ID NO: 159 | HCDR1 (Combined) | GYSFTSYWIG |
| SEQ ID NO: 160 | HCDR2 (Combined) | VIDPSGSYTIYSPSFQG |
| SEQ ID NO: 161 | HCDR3 (Combined) | YGRYGTYFDY |
| SEQ ID NO: 162 | HCDR1 (Kabat) | SYVVIG |
| SEQ ID NO: 163 | HCDR2 (Kabat) | VIDPSGSYTIYSPSFQG |
| SEQ ID NO: 164 | HCDR3 (Kabat) | YGRYGTYFDY |
| SEQ ID NO: 165 | HCDR1 (Chothia) | GYSFTSY |
| SEQ ID NO: 166 | HCDR2 (Chothia) | DPSGSY |
| SEQ ID NO: 167 | HCDR3 (Chothia) | YGRYGTYFDY |
| SEQ ID NO: 168 | VH | EVQLVQSGAEVKKPGESLKISCKGSGYSFTSYWIGWVRQMPGKGLEWMGVIDPSGSYTIYSPSFQGQVTISADKSISTAYLQWSSLKASDTAMYYCARYGRYGTYFDYWGQGTLVTVSS |
| SEQ ID NO: 169 | DNA VH | GAAGTGCAACTCGTGCAGTCCGGAGCCGAGGTCAAGAAGCCCGGAGAATCCCTGAAGATTAGCTGCAAGGGCTCCGGATACTCATTCACTTCATATTGGATCGGCTGGGTCCGGCAGATGCCGGGGAAGGGGCTGGAGTGGATGGGAGTGATCGACCCGTCCGGTTCCTACACCATCTACTCGCCAAGCTTCCAAGGACAGGTCACCATCTCTGCCGATAAGTCGATTTCCACGGCATACTTGCAGTGGTCGTCCCTGAAAGCGTCCGACACTGCGATGTACTACTGTGCCCGCTACGGAAGATACGGCACCTACTTTGACTACTGGGGCCAGGGGACTCTCGTGACCGTGTCCAGC |
| SEQ ID NO: 170 | Heavy Chain | EVQLVQSGAEVKKPGESLKISCKGSGYSFTSYWIGWVRQMPGKGLEWMGVIDPSGSYTIYSPSFQGQVTISADKSISTAYLQWSSLKASDTAMYYCARYGRYGTYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 171 | DNA Heavy Chain | GAAGTGCAACTCGTGCAGTCCGGAGCCGAGGTCAAGAAGCCCGGAGAATCCCTGAAGATTAGCTGCAAGGGCTCCGGATACTCATTCACTTCATATTGGATCGGCTGGGTCCGGCAGATGCCGGGGAAGGGGCTGGAGTGGATGGGAGTGATCGACCCGTCCGGTTCCTACACCATCTACTCGCCAAGCTTCCAAGGACAGGTCACCATCTCTGCCGATAAGTCGATTTCCACGGCATACTTGCAGTGGTCGTCCCTGAAAGCGTCCGACACTGCGATGTACTACTGTGCCCGCTACGGAAGATACGGCACCTACTTTGACTACTGGGGCCAGGGGACTCTCGTGACCGTGTCCAGCGCTAGCACCAAGGGCCCAAGTGTGTTTCCCCTGGCCCCCAGCAGCAAGTCTACTTCCGGCGGAACTGCTGCCCTGGGTTGCCTGGTGAAGGACTACTTCCCGAGCCCGTGACAGTGTCCTGGAACTCTGGGGCTCTGACTTCCGGCGTGCACACCTTCCCCGCCGTGCTGCAGAGCA |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | GCGGCCTGTACAGCCTGAGCAGCGTGGTGACAGTGCCC<br>TCCAGCTCTCTGGGAACCCAGACCTATATCTGCAACGT<br>GAACCACAAGCCCAGCAACACCAAGGTGGACAAGAGAG<br>TGGAGCCCAAGAGCTGCGACAAGACCCACACCTGCCCC<br>CCTGCCCAGCTCCAGAACTGCTGGGAGGGCCTTCCGTGT<br>TCCTGTTCCCCCCCAAGCCCAAGGACACCCTGATGATCA<br>GCAGGACCCCCGAGGTGACCTGCGTGGTGGTGGACGTG<br>TCCCACGAGGACCCAGAGGTGAAGTTCAACTGGTACGT<br>GGACGGCGTGGAGGTGCACAACGCCAAGACCAAGCCCA<br>GAGAGGAGCAGTACAACAGCACCTACAGGGTGGTGTCC<br>GTGCTGACCGTGCTGCACCAGGACTGGCTGAACGGCAA<br>AGAATACAAGTGCAAAGTCTCCAACAAGGCCCTGCCAG<br>CCCCAATCGAAAAGACAATCAGCAAGGCCAAGGGCCAG<br>CCACGGGAGCCCCAGGTGTACACCCTGCCCCCCAGCCGG<br>GAGGAGATGACCAAGAACCAGGTGTCCCTGACCTGTCT<br>GGTGAAGGGCTTCTACCCCAGCGATATCGCCGTGGAGT<br>GGGAGAGCAACGGCCAGCCCGAGAACAACTACAAGACC<br>ACCCCCCCAGTGCTGGACAGCGACGGCAGCTTCTTCCTG<br>TACAGCAAGCTGACCGTGGACAAGTCCAGGTGGCAGCA<br>GGGCAACGTGTTCAGCTGCAGCGTGATGCACGAGGCCC<br>TGCACAACCACTACACCCAGAAGTCCCTGAGCCTGAGC<br>CCCGGCAAG |
| SEQ ID NO: 172 | LCDR1 (Combined) | SGSSSNIGVLYVN |
| SEQ ID NO: 173 | LCDR2 (Combined) | SNDNRPS |
| SEQ ID NO: 174 | LCDR3 (Combined) | QSWDSSSNYV |
| SEQ ID NO: 175 | LCDR1 (Kabat) | SGSSSNIGVLYVN |
| SEQ ID NO: 176 | LCDR2 (Kabat) | SNDNRPS |
| SEQ ID NO: 177 | LCDR3 (Kabat) | QSWDSSSNYV |
| SEQ ID NO: 178 | LCDR1 | SSSNIGVLY |
| SEQ ID NO: 179 | LCDR2 | SND |
| SEQ ID NO: 180 | LCDR3 | WDSSSNY |
| SEQ ID NO: 181 | VL | QSVLTQPPSVSGAPGQRVTISCSGSSSNIGVLYVNWYQQ<br>LPGTAPKLLIYSNDNRPSGVPDRFSGSKSGTSASLAITGL<br>QAEDEADYYCQSWDSSSNYVFGGGTKLTVL |
| SEQ ID NO: 182 | DNA VL | CAATCGGTGCTGACCCAGCCCCCTTCGGTGTCCGGAGCC<br>CCGGGCCAGAGAGTGACCATCAGCTGCTCGGGTTCCTC<br>TAGCAACATCGGGGTGCTCTACGTGAACTGGTACCAGC<br>AGCTGCCGGGCACCGCCCCAAAGCTGCTGATCTATAGC<br>AATGATAACCGGCCGTCCGGAGTGCCCGACCGGTTCTC<br>CGGATCAAAGAGCGGCACCTCCGCATCCTTGGCCATTA<br>CGGGGCTGCAGGCGGAGGACGAAGCTGATTACTACTGT<br>CAATCGTGGGACTCCTCATCCAACTACGTGTTCGGCGG<br>AGGCACCAAACTGACTGTCCTG |
| SEQ ID NO: 183 | Light Chain | QSVLTQPPSVSGAPGQRVTISCSGSSSNIGVLYVNWYQQ<br>LPGTAPKLLIYSNDNRPSGVPDRFSGSKSGTSASLAITGL<br>QAEDEADYYCQSWDSSSNYVFGGGTKLTVLGQPKAAPS<br>VTLFPPSSEELQANKATLVCLISDFYPGAVTVAWKADSS<br>PVKAGVETTTPSKQSNNKYAASSYLSLTPEQWKSHRSY<br>SCQVTHEGSTVEKTVAPTECS |
| SEQ ID NO: 184 | DNA Light Chain | CAATCGGTGCTGACCCAGCCCCCTTCGGTGTCCGGAGCC<br>CCGGGCCAGAGAGTGACCATCAGCTGCTCGGGTTCCTC |

TABLE 1-continued

Examples of GDF15 Antibodies, Heavy Chain and Light Chain Sequences and GDF15 Proteins

| Sequence Identifier (SEQ ID NO.) | Sequence Description | Amino acid or nucleotide sequence |
|---|---|---|
| | | TAGCAACATCGGGGTGCTCTACGTGAACTGGTACCAGC AGCTGCCGGGCACCGCCCCAAAGCTGCTGATCTATAGC AATGATAACCGGCCGTCCGGAGTGCCCGACCGGTTCTC CGGATCAAAGAGCGGCACCTCCGCATCCTTGGCCATTA CGGGGCTGCAGGCGGAGGACGAAGCTGATTACTACTGT CAATCGTGGGACTCCTCATCCAACTACGTGTTCGGCGG AGGCACCAAACTGACTGTCCTGGGTCAGCCTAAGGCTG CCCCCAGCGTGACCCTGTTCCCCCCCAGCAGCGAGGAGC TGCAGGCCAACAAGGCCACCCTGGTGTGCCTGATCAGC GACTTCTACCCAGGCGCCGTGACCGTGGCCTGGAAGGC CGACAGCAGCCCCGTGAAGGCCGGCGTGGAGACCACCA CCCCCAGCAAGCAGAGCAACAACAAGTACGCCGCCAGC AGCTACCTGAGCCTGACCCCCGAGCAGTGGAAGAGCCA CAGGTCCTACAGCTGCCAGGTGACCCACGAGGGCAGCA CCGTGGAAAAGACCGTGGCCCCAACCGAGTGCAGC |

TABLE 2

Binding Characteristics of Anti-GDF15 Antibodies

| Antibody | Ligand ID | ka (1/Ms) | kd (1/s) | KD (M) | Rmax (RU) |
|---|---|---|---|---|---|
| ABGDF15-A | Human GDF15 native | 3.30E+07 | 3.74E−04 | 1.131E−11 | 8.19 |
| | Human His-GDF15 | 9.42E+07 | 2.47E−04 | 2.624E−12 | 9.443 |
| | Cyno His-GDF15 | 2.07E+07 | 2.78E−04 | 1.338E−11 | 9.23 |
| | Mouse His-GDF15 | 1.08E+07 | 6.13E−04 | 5.681E−11 | 9.995 |
| | Rat His-GDF15 | 1.95E+07 | 4.51E−04 | 2.318E−11 | 8.519 |
| ABGDF15-G | Human GDF15 Native | 5.80E+06 | 5.12E−04 | 8.822E−11 | 6.116 |
| | Human His-GDF15 | 3.90E+06 | 5.33E−04 | 1.365E−10 | 7.62 |
| | Cyno His-GDF15 | 5.79E+06 | 6.94E−04 | 1.199E−10 | 5.627 |
| | Mouse His-GDF15 | 2.23E+06 | 3.43E−04 | 1.542E−10 | 4.271 |
| | Rat His-GDF15 | 2.63E+06 | 3.65E−04 | 1.384E−10 | 3.977 |
| ABGDF15-B | Human GDF15 Native | 3.38E+06 | 3.89E−04 | 1.149E−10 | 7.109 |
| | Human His-GDF15 | 8.80E+06 | 5.40E−04 | 6.137E−11 | 8.592 |
| | Cyno His-GDF15 | 5.52E+06 | 4.61E−04 | 8.358E−11 | 7.029 |
| | Mouse His-GDF15 | 2.64E+06 | 6.26E−04 | 2.368E−10 | 8.63 |
| | Rat His-GDF15 | 5.36E+06 | 5.20E−04 | 9.703E−11 | 9.086 |
| ABGDF15-C | Human GDF15 Native | 5.92E+06 | 3.88E−04 | 6.561E−11 | 7.519 |
| | Human His-GDF15 | 1.11E+07 | 4.68E−04 | 4.217E−11 | 9.548 |
| | Cyno His-GDF15 | 4.96E+06 | 3.22E−04 | 6.498E−11 | 8.294 |
| | Mouse His-GDF15 | 4.37E+06 | 5.05E−04 | 1.156E−10 | 7.981 |
| | Rat His-GDF15 | 7.81E+06 | 4.83E−04 | 6.18E−11 | 8.465 |
| ABGDF15-D | Human GDF15 Native | 1.71E+07 | 3.32E−04 | 1.939E−11 | 3.868 |
| | Human His-GDF15 | 4.09E+07 | 2.61E−04 | 6.393E−12 | 4.938 |
| | Cyno His-GDF15 | 1.67E+07 | 2.36E−04 | 1.411E−11 | 4.516 |
| | Mouse His-GDF15 | 1.11E+07 | 5.09E−04 | 4.573E−11 | 8.519 |
| | Rat His-GDF15 | 1.62E+07 | 4.56E−04 | 2.807E−11 | 7.898 |
| ABGDF15-E | Human GDF15 Native | 8.98E+06 | 3.50E−04 | 3.896E−11 | 5.293 |
| | Human His-GDF15 | 4.63E+07 | 3.41E−04 | 7.356E−12 | 4.955 |
| | Cyno His-GDF15 | 1.26E+07 | 3.80E−04 | 3.029E−11 | 4.886 |
| | Mouse His-GDF15 | 6.78E+06 | 5.35E−04 | 7.897E−11 | 10.05 |
| | Rat His-GDF15 | 1.08E+07 | 4.28E−04 | 3.957E−11 | 8.45 |
| ABGDF15-F | Human GDF15 Native | 1.89E+07 | 6.96E−04 | 3.681E−11 | 3.206 |
| | Human His-GDF15 | 4.19E+07 | 4.80E−04 | 1.145E−11 | 4.366 |
| | Cyno His-GDF15 | 1.26E+07 | 4.40E−04 | 3.498E−11 | 4.07 |
| | Mouse His-GDF15 | 6.05E+06 | 5.84E−04 | 9.64E−11 | 11.14 |
| | Rat His-GDF15 | 1.11E+07 | 5.38E−04 | 4.849E−11 | 9.183 |

The measurements provided in Table 2 were obtained using Biacore analysis as described in the Examples. Different ligands were tested with each antibody as shown in Table 2. For example, the following ligands were tested:
Human GDF15 native: naturally produced human GDF15 purchased from Peprotech;
Human His-GDF15: HIS-tagged human GDF15;
Cyno His-GDF15: HIS-tagged cyno GDF15;
Mouse His-GDF15: HIS-tagged mouse GDF15; and
Rat GDF15 HIS: HIS-tagged rat GDF15.

Table 3 provides the binding affinity (dissociation constant) of selected anti-GDF15 antibodies according to SET and Biacore.

TABLE 3

Kd Values of Anti-GDF15 Antibodies according to SET and Biacore

| Candidate | SET Kd M | Biacore Kd (nM) |
|---|---|---|
| ABGDF15-A | 0.001 | 0.011 |
| ABGDF15-B | 0.12 | 0.115 |
| ABGDF15-C | 0.12 | 0.066 |
| ABGDF15-D | 0.00016 | 0.019 |
| ABGDF15-E | 0.0023 | 0.039 |
| ABGDF15-F | 0.0044 | 0.037 |
| ABGDF15-G | 0.02 | 0.088 |

TABLE 4

Isoelectric point (pI) of Anti-GDF15 Antibodies

| Candidate | pI IgG | | | pI Fab | | |
|---|---|---|---|---|---|---|
| | Heavy | Light | Heavy + Light | Heavy | Light | Heavy + Light |
| ABGDF15-C | 9.4 | 5.7 | 8.3 | 9.9 | 5.7 | 8.8 |
| ABGDF15-B | 9.4 | 6.8 | 8.9 | 9.9 | 6.8 | 9.3 |
| ABGDF15-A | 9 | 7.4 | 8.7 | 9.5 | 7.4 | 9.1 |
| ABGDF15-F | 9.3 | 5.8 | 8.9 | 9.7 | 5.8 | 9.2 |
| ABGDF15-E | 9.3 | 5.8 | 8.9 | 9.7 | 5.8 | 9.2 |
| ABGDF15-G | 9.3 | 9.4 | 9.3 | 9.8 | 9.4 | 9.6 |
| ABGDF15-D | 9.2 | 5.8 | 8.6 | 9.6 | 5.8 | 9 |

Other antibodies include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to GDF15, the VH, VL, full length light chain, and full length heavy chain sequences (amino acid sequences and the nucleotide sequences encoding the amino acid sequences) can be "mixed and matched" to create other GDF15-binding antibodies described herein. Such "mixed and matched" GDF15-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, provided herein is an isolated antibody or antigen binding region thereof having: a heavy chain variable domain comprising an amino acid sequence selected from the group consisting of SEQ ID NOs: 12, 38, 64, 90, 116, 142, 168, and a light chain variable domain comprising an amino acid sequence selected from the group consisting of SEQ ID NOs: 25, 51, 77, 103, 129, 155 and 181, wherein the antibody specifically binds to GDF15 (e.g., human GDF15).

More specifically, in certain aspects, provided herein is an isolated antibody or antigen binding region thereof having a heavy chain variable domain and a light chain variable domain comprising amino acid sequences selected from SEQ ID NOs: 12 and 25; 38 and 51; 64 and 77; 90 and 103; 116 and 129; 142 and 155; or 168 and 181, respectively. In certain aspects, provided herein is an isolated antibody or antigen binding region thereof having a heavy chain variable domain (VH) comprising the amino acid sequence of SEQ ID NO: 12 and a light chain variable domain (VL) comprising the amino acid sequence of SEQ ID NO: 25. In certain aspects, provided herein is an isolated antibody or antigen binding region thereof having a heavy chain variable domain (VH) comprising the amino acid sequence of SEQ ID NO: 38 and a light chain variable domain (VL) comprising the amino acid sequence of SEQ ID NO: 51. In certain aspects, provided herein is an isolated antibody or antigen binding region thereof having a heavy chain variable domain (VH) comprising the amino acid sequence of SEQ ID NO: 64 and a light chain variable domain (VL) comprising the amino acid sequence of SEQ ID NO: 77. In certain aspects, provided herein is an isolated antibody or antigen binding region thereof having a heavy chain variable domain (VH) comprising the amino acid sequence of SEQ ID NO: 90 and a light chain variable domain (VL) comprising the amino acid sequence of SEQ ID NO: 103. In certain aspects, provided herein is an isolated antibody or antigen binding region thereof having a heavy chain variable domain (VH) comprising the amino acid sequence of SEQ ID NO: 116 and a light chain variable domain (VL) comprising the amino acid sequence of SEQ ID NO: 129. In certain aspects, provided herein is an isolated antibody or antigen binding region thereof having a heavy chain variable domain (VH) comprising the amino acid sequence of SEQ ID NO: 142 and a light chain variable domain (VL) comprising the amino acid sequence of SEQ ID NO: 155. In certain aspects, provided herein is an isolated antibody or antigen binding region thereof having a heavy chain variable domain (VH) comprising the amino acid sequence of SEQ ID NO: 168 and a light chain variable domain (VL) comprising the amino acid sequence of SEQ ID NO: 181.

In another aspect, provided herein is (i) an isolated antibody having: a full length heavy chain comprising an amino acid sequence that has been optimized for expression in a mammalian cell selected from the group consisting of SEQ ID NOs: 14, 40, 66, 92, 118, 144, and 170, and a full length light chain comprising an amino acid sequence that has been optimized for expression in a mammalian cell selected from the group consisting of SEQ ID NOs: 27, 53, 79, 105, 131, 157, and 183; or (ii) a functional protein comprising an antigen binding portion thereof. More specifically, in certain aspects, provided herein is an isolated antibody or antigen binding region thereof having a heavy chain and a light chain comprising amino acid sequences selected from SEQ ID NOs: 14 and 27; 40 and 53; 66 and 79; 92 and 105; 118 and 131; 144 and 157; or 170 and 183, respectively. In particular aspects, provided herein is an isolated antibody or antigen binding region thereof comprising a heavy chain comprising the amino acid sequence of SEQ ID NO: 14 and a light chain comprising the amino acid sequence of SEQ ID NO: 27. In particular aspects, provided herein is an isolated antibody or antigen binding region thereof comprising a heavy chain comprising the amino acid sequence of SEQ ID NO: 40 and a light chain comprising the amino acid sequence of SEQ ID NO: 53. In particular aspects, provided herein is an isolated antibody or antigen binding region thereof comprising a heavy chain comprising the amino acid sequence of SEQ ID NO: 66 and a light chain comprising the amino acid sequence of SEQ ID NO: 79. In particular aspects, provided herein is an isolated antibody or antigen binding region thereof comprising a heavy chain comprising the amino acid sequence of SEQ ID NO: 92 and a light chain comprising the amino acid sequence of SEQ ID NO: 105. In particular aspects, provided herein is an isolated antibody or antigen binding region thereof comprising a heavy chain comprising the amino acid sequence of SEQ ID NO: 118 and a light chain comprising the amino acid sequence of SEQ ID NO: 131. In particular aspects, provided herein is an isolated antibody or antigen binding region thereof comprising a heavy chain comprising the amino acid sequence of SEQ ID NO: 144 and a light chain comprising the amino acid sequence of SEQ ID NO: 157. In particular aspects, provided herein is an isolated antibody or antigen binding region thereof comprising a heavy chain comprising the amino acid sequence of SEQ ID NO: 170 and a light chain comprising the amino acid sequence of SEQ ID NO: 183.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme).

For example, under Kabat, the CDR amino acid residues of antibody ABGDF15-A in the heavy chain variable domain (VH) are numbered 31-35 (HCDR1), 50-66 (HCDR2), and 99-108 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-57 (HCDR2), and 99-108 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-66 (HCDR2), and 99-108 (HCDR3) in human VH and amino acid residues 24-34 (LCDR1), 50-56 (LCDR2), and 89-97 (LCDR3) in human VL.

In another aspect, provided herein are GDF15 binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 6, 32, 58, 84, 110, 136, 162. The amino acid sequences of the VH CDR2s of the antibodies and are shown in SEQ ID NOs: 7, 33, 59, 85, 111, 137, 163. The amino acid sequences of the VH CDR3s of the antibodies are shown in SEQ ID NOs: 8, 34, 60, 86, 112, 138, 164. The amino acid sequences of the VL CDR1s of the antibodies are shown in SEQ ID NOs: 19, 45, 71, 97, 123, 149, 175. The amino acid sequences of the VL CDR2s of the antibodies are shown in SEQ ID NOs: 20, 46, 72, 98, 124, 150, 176. The amino acid sequences of the VL CDR3s of the antibodies are shown in SEQ ID NOs: 21, 47, 73, 99, 125, 151, 177. These CDR regions are delineated using the Kabat system.

Alternatively, as defined using the Chothia system (Al-Lazikani et al., (1997) JMB 273, 927-948), the amino acid sequences of the VH CDR1s of the antibodies are shown in SEQ ID NOs: 9, 35, 61, 87, 113, 139, 165. The amino acid sequences of the VH CDR2s of the antibodies and are shown in SEQ ID NOs: 10, 36, 62, 88, 114, 140, 166. The amino acid sequences of the VH CDR3s of the antibodies are shown in SEQ ID NOs: 11, 37, 63, 89, 115, 141, 167. The amino acid sequences of the VL CDR1s of the antibodies are shown in SEQ ID NOs: 22, 48, 74, 100, 126, 152, 178. The amino acid sequences of the VL CDR2s of the antibodies are shown in SEQ ID NOs: 23, 49, 75, 101, 127, 153, 179. The amino acid sequences of the VL CDR3s of the antibodies are shown in SEQ ID NOs: 24, 50, 76, 102, 128, 154, 180.

In another aspect, premised on combining the numbering of the Kabat and Chothia systems, provided herein is GDF15 binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 3, 29, 55, 81, 107, 133, 159. The amino acid sequences of the VH CDR2s of the antibodies and are shown in SEQ ID NOs: 4, 30, 56, 82, 108, 134, 160. The amino acid sequences of the VH CDR3s of the antibodies are shown in SEQ ID NOs: 5, 31, 57, 83, 109, 135, 161. The amino acid sequences of the VL CDR1s of the antibodies are shown in SEQ ID NOs: 16, 42, 68, 94, 120, 146, 172. The amino acid sequences of the VL CDR2s of the antibodies are shown in SEQ ID NOs: 17, 43, 69, 95, 121, 147, 173. The amino acid sequences of the VL CDR3s of the antibodies are shown in SEQ ID NOs: 18, 44, 70, 96, 122, 148, 174. These CDR regions are delineated using the combined system.

Given that each of these antibodies can bind to GDF15 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched), although each antibody preferably contains a VH CDR1, 2 and 3 and a VL CDR1, 2 and 3 to create other GDF15 binding molecules described herein. Such "mixed and matched" GDF15 binding antibodies can be tested using the binding assays known in the art and those described in the Examples (e.g., ELISAs, SET, Biacore). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies. In addition to the foregoing, in one embodiment, the antigen binding fragments of the antibodies described herein can comprise a VH CDR1, 2, and 3, or a VL CDR 1, 2, and 3, wherein the fragment binds to GDF15 as a single variable domain.

In certain embodiments, the antibodies or antigen binding fragments thereof may have the heavy and light chain sequences of the Fabs described in Table 1. More specifically, the antibody or antigen binding fragments thereof may have the heavy and light sequence of ABGDF15-A, ABGDF15-G, ABGDF15-B, ABGDF15-C, ABGDF15-F, ABGDF15-E, or ABGDF15-D. In a specific embodiment, the antibody or antigen binding fragments thereof may have the heavy chain and light chain sequences of ABGDF15-A, ABGDF15-D, ABGDF15-E, or ABGDF15-F.

In certain embodiments, the antibody or antigen binding fragment specifically binds GDF15 comprises a heavy chain variable region CDR1, a heavy chain variable region CDR2, a heavy chain variable region CDR3, a light chain variable region CDR1, a light chain variable region CDR2, and a light chain variable region CDR3 as defined by combined Kabat and Chothia and described in Table 1. In other embodiments, the antibody or antigen binding fragment specifically binds GDF15 comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments, the antibody or antigen binding fragment in that specifically binds GDF15 comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In one embodiment, provided herein is an antibody that specifically binds to GDF15 comprising:
(i) an HCDR1 of SEQ ID NO: 3; an HCDR2 of SEQ ID NO: 4; an HCDR3 of SEQ ID NO: 5; an LCDR1 of SEQ ID NO: 16; an LCDR2 of SEQ ID NO: 17; and an LCDR3 of SEQ ID NO: 18; or
(ii) an HCDR1 of SEQ ID NO: 6; an HCDR2 of SEQ ID NO: 7; an HCDR3 of SEQ ID NO: 8; an LCDR1 of SEQ ID NO: 19; an LCDR2 of SEQ ID NO: 20; and an LCDR3 of SEQ ID NO: 21; or
(iii) an HCDR1 of SEQ ID NO: 9; an HCDR2 of SEQ ID NO: 10; an HCDR3 of SEQ ID NO: 11; an LCDR1 of SEQ ID NO: 22; an LCDR2 of SEQ ID NO: 23; and an LCDR3 of SEQ ID NO: 24.

In one embodiment, provided herein is an antibody that specifically binds to GDF15 comprising:
(i) an HCDR1 of SEQ ID NO: 107; an HCDR2 of SEQ ID NO: 108; an HCDR3 of SEQ ID NO: 109; an LCDR1 of SEQ ID NO: 120; an LCDR2 of SEQ ID NO: 121; and an LCDR3 of SEQ ID NO: 122; or
(ii) an HCDR1 of SEQ ID NO: 110; an HCDR2 of SEQ ID NO: 111; an HCDR3 of SEQ ID NO: 112; an LCDR1 of SEQ ID NO: 123; an LCDR2 of SEQ ID NO: 124; and an LCDR3 of SEQ ID NO: 125; or
(iii) an HCDR1 of SEQ ID NO: 113; an HCDR2 of SEQ ID NO: 114; an HCDR3 of SEQ ID NO: 115; an LCDR1 of SEQ ID NO: 126; an LCDR2 of SEQ ID NO: 127; and an LCDR3 of SEQ ID NO: 128.

In one embodiment, provided herein is an antibody that specifically binds to GDF15 comprising:
(i) an HCDR1 of SEQ ID NO: 29; an HCDR2 of SEQ ID NO: 30; an HCDR3 of SEQ ID NO: 31; an LCDR1 of SEQ ID NO: 42; an LCDR2 of SEQ ID NO: 43; and an LCDR3 of SEQ ID NO: 44; or
(ii) an HCDR1 of SEQ ID NO: 32; an HCDR2 of SEQ ID NO: 33; an HCDR3 of SEQ ID NO: 34; an LCDR1 of SEQ ID NO: 45; an LCDR2 of SEQ ID NO: 46; and an LCDR3 of SEQ ID NO: 47; or
(iii) an HCDR1 of SEQ ID NO: 35; an HCDR2 of SEQ ID NO: 36; an HCDR3 of SEQ ID NO: 37; an LCDR1 of SEQ ID NO: 48; an LCDR2 of SEQ ID NO: 49; and an LCDR3 of SEQ ID NO: 50.

In one embodiment, provided herein is an antibody that specifically binds to GDF15 comprising:
(i) an HCDR1 of SEQ ID NO: 55; an HCDR2 of SEQ ID NO: 56; an HCDR3 of SEQ ID NO: 57; an LCDR1 of SEQ ID NO: 68; an LCDR2 of SEQ ID NO: 69; and an LCDR3 of SEQ ID NO: 70; or
(ii) an HCDR1 of SEQ ID NO: 58; an HCDR2 of SEQ ID NO: 59; an HCDR3 of SEQ ID NO: 60; an LCDR1 of SEQ ID NO: 71; an LCDR2 of SEQ ID NO: 72; and an LCDR3 of SEQ ID NO: 73; or
(iii) an HCDR1 of SEQ ID NO: 61; an HCDR2 of SEQ ID NO: 62; an HCDR3 of SEQ ID NO: 63; an LCDR1 of SEQ ID NO: 74; an LCDR2 of SEQ ID NO: 75; and an LCDR3 of SEQ ID NO: 76.

In one embodiment, provided herein is an antibody that specifically binds to GDF15 comprising:
(i) an HCDR1 of SEQ ID NO: 81; an HCDR2 of SEQ ID NO: 82; an HCDR3 of SEQ ID NO: 83; an LCDR1 of SEQ ID NO: 94; an LCDR2 of SEQ ID NO: 95; and an LCDR3 of SEQ ID NO: 96; or
(ii) an HCDR1 of SEQ ID NO: 84; an HCDR2 of SEQ ID NO: 85; an HCDR3 of SEQ ID NO: 86; an LCDR1 of SEQ ID NO: 97; an LCDR2 of SEQ ID NO: 98; and an LCDR3 of SEQ ID NO: 99; or
(iii) an HCDR1 of SEQ ID NO: 87; an HCDR2 of SEQ ID NO: 88; an HCDR3 of SEQ ID NO: 89; an LCDR1 of SEQ ID NO: 100; an LCDR2 of SEQ ID NO: 101; and an LCDR3 of SEQ ID NO: 102.

In one embodiment, provided herein is an antibody that specifically binds to GDF15 comprising:
(i) an HCDR1 of SEQ ID NO: 133; an HCDR2 of SEQ ID NO: 134; an HCDR3 of SEQ ID NO: 135; an LCDR1 of SEQ ID NO: 146; an LCDR2 of SEQ ID NO: 147; and an LCDR3 of SEQ ID NO: 148; or
(ii) an HCDR1 of SEQ ID NO: 136; an HCDR2 of SEQ ID NO: 137; an HCDR3 of SEQ ID NO: 138; an LCDR1 of SEQ ID NO: 149; an LCDR2 of SEQ ID NO: 150; and an LCDR3 of SEQ ID NO: 151; or
(iii) an HCDR1 of SEQ ID NO: 139; an HCDR2 of SEQ ID NO: 140; an HCDR3 of SEQ ID NO: 141; an LCDR1 of SEQ ID NO: 152; an LCDR2 of SEQ ID NO: 153; and an LCDR3 of SEQ ID NO: 154.

In one embodiment, provided herein is an antibody that specifically binds to GDF15 comprising:
(i) an HCDR1 of SEQ ID NO: 159; an HCDR2 of SEQ ID NO: 160; an HCDR3 of SEQ ID NO: 161; an LCDR1 of SEQ ID NO: 172; an LCDR2 of SEQ ID NO: 173; and an LCDR3 of SEQ ID NO: 174; or
(ii) an HCDR1 of SEQ ID NO: 162; an HCDR2 of SEQ ID NO: 163; an HCDR3 of SEQ ID NO: 164; an LCDR1 of SEQ ID NO: 175; an LCDR2 of SEQ ID NO: 176; and an LCDR3 of SEQ ID NO: 177; or
(iii) an HCDR1 of SEQ ID NO: 165; an HCDR2 of SEQ ID NO: 166; an HCDR3 of SEQ ID NO: 167; an LCDR1 of SEQ ID NO: 178; an LCDR2 of SEQ ID NO: 179; and a light chain variable region CDR3 of SEQ ID NO: 180.

In one embodiment, provided herein is an antibody that specifically binds to GDF15 comprising a heavy chain variable region CDR1 of SEQ ID NO: 3; a heavy chain variable region CDR2 of SEQ ID NO: 4; a heavy chain variable region CDR3 of SEQ ID NO: 5; a light chain variable region CDR1 of SEQ ID NO: 16; a light chain variable region CDR2 of SEQ ID NO: 17; and a light chain variable region CDR3 of SEQ ID NO: 18.

In one embodiment, provided herein is an antibody that specifically binds to GDF15 comprising a heavy chain variable region CDR1 of SEQ ID NO: 29; a heavy chain variable region CDR2 of SEQ ID NO: 30; a heavy chain variable region CDR3 of SEQ ID NO: 31; a light chain variable region CDR1 of SEQ ID NO: 42; a light chain variable region CDR2 of SEQ ID NO: 43; and a light chain variable region CDR3 of SEQ ID NO: 44.

In one embodiment, provided herein is an antibody that specifically binds to GDF15 comprising a heavy chain variable region CDR1 of SEQ ID NO: 55; a heavy chain variable region CDR2 of SEQ ID NO: 56; a heavy chain variable region CDR3 of SEQ ID NO: 57; a light chain variable region CDR1 of SEQ ID NO: 68; a light chain variable region CDR2 of SEQ ID NO: 69; and a light chain variable region CDR3 of SEQ ID NO: 70.

In one embodiment, provided herein is an antibody that specifically binds to GDF15 comprising a heavy chain variable region CDR1 of SEQ ID NO: 81; a heavy chain variable region CDR2 of SEQ ID NO: 82; a heavy chain variable region CDR3 of SEQ ID NO: 83; a light chain variable region CDR1 of SEQ ID NO: 94; a light chain variable region CDR2 of SEQ ID NO: 95; and a light chain variable region CDR3 of SEQ ID NO: 96.

In one embodiment, provided herein is an antibody that specifically binds to GDF15 comprising a heavy chain variable region CDR1 of SEQ ID NO: 107; a heavy chain variable region CDR2 of SEQ ID NO: 108; a heavy chain variable region CDR3 of SEQ ID NO: 109; a light chain variable region CDR1 of SEQ ID NO: 120; a light chain variable region CDR2 of SEQ ID NO: 121; and a light chain variable region CDR3 of SEQ ID NO: 122.

In one embodiment, provided herein is an antibody that specifically binds to GDF15 comprising a heavy chain variable region CDR1 of SEQ ID NO: 133; a heavy chain variable region CDR2 of SEQ ID NO: 134; a heavy chain variable region CDR3 of SEQ ID NO: 135; a light chain variable region CDR1 of SEQ ID NO: 146; a light chain variable region CDR2 of SEQ ID NO: 147; and a light chain variable region CDR3 of SEQ ID NO: 148.

In one embodiment, provided herein is an antibody that specifically binds to GDF15 comprising a heavy chain variable region CDR1 of SEQ ID NO: 159; a heavy chain variable region CDR2 of SEQ ID NO: 160; a heavy chain variable region CDR3 of SEQ ID NO: 161; a light chain variable region CDR1 of SEQ ID NO: 172; a light chain variable region CDR2 of SEQ ID NO: 173; and a light chain variable region CDR3 of SEQ ID NO: 174.

In one embodiment, provided herein is an antibody that specifically binds to GDF15 comprising a heavy chain variable region CDR1 of SEQ ID NO: 6; a heavy chain variable region CDR2 of SEQ ID NO: 7; a heavy chain variable region CDR3 of SEQ ID NO: 8; a light chain variable region CDR1 of SEQ ID NO: 19; a light chain variable region CDR2 of SEQ ID NO: 20; and a light chain variable region CDR3 of SEQ ID NO: 21.

In one embodiment, provided herein is an antibody that specifically binds to GDF15 comprising a heavy chain variable region CDR1 of SEQ ID NO: 32; a heavy chain variable region CDR2 of SEQ ID NO: 33; a heavy chain variable region CDR3 of SEQ ID NO: 34; a light chain variable region CDR1 of SEQ ID NO: 45; a light chain variable region CDR2 of SEQ ID NO: 46; and a light chain variable region CDR3 of SEQ ID NO: 47.

In a specific embodiment, provided herein is an antibody that specifically binds to GDF15 comprising a heavy chain variable region CDR1 of SEQ ID NO: 58; a heavy chain variable region CDR2 of SEQ ID NO: 59; a heavy chain variable region CDR3 of SEQ ID NO: 60; a light chain variable region CDR1 of SEQ ID NO: 71; a light chain variable region CDR2 of SEQ ID NO: 72; and a light chain variable region CDR3 of SEQ ID NO: 73.

In a specific embodiment, provided herein is an antibody that specifically binds to GDF15 comprising a heavy chain variable region CDR1 of SEQ ID NO: 84; a heavy chain variable region CDR2 of SEQ ID NO: 85; a heavy chain variable region CDR3 of SEQ ID NO: 86; a light chain variable region CDR1 of SEQ ID NO: 97; a light chain variable region CDR2 of SEQ ID NO: 98; and a light chain variable region CDR3 of SEQ ID NO: 99.

In a specific embodiment, provided herein is an antibody that specifically binds to GDF15 comprising a heavy chain variable region CDR1 of SEQ ID NO: 110; a heavy chain variable region CDR2 of SEQ ID NO: 111; a heavy chain variable region CDR3 of SEQ ID NO: 112; a light chain variable region CDR1 of SEQ ID NO: 123; a light chain variable region CDR2 of SEQ ID NO: 124; and a light chain variable region CDR3 of SEQ ID NO: 125.

In a specific embodiment, provided herein is an antibody that specifically binds to GDF15 comprising a heavy chain variable region CDR1 of SEQ ID NO: 136; a heavy chain variable region CDR2 of SEQ ID NO: 137; a heavy chain variable region CDR3 of SEQ ID NO: 138; a light chain variable region CDR1 of SEQ ID NO: 149; a light chain variable region CDR2 of SEQ ID NO: 150; and a light chain variable region CDR3 of SEQ ID NO: 151.

In a specific embodiment, provided herein is an antibody that specifically binds to GDF15 comprising a heavy chain variable region CDR1 of SEQ ID NO: 162; a heavy chain variable region CDR2 of SEQ ID NO: 163; a heavy chain variable region CDR3 of SEQ ID NO: 164; a light chain variable region CDR1 of SEQ ID NO: 175; a light chain variable region CDR2 of SEQ ID NO: 176; and a light chain variable region CDR3 of SEQ ID NO: 177.

In a specific embodiment, provided herein is an antibody that specifically binds to GDF15 comprising a heavy chain variable region CDR1 of SEQ ID NO: 9; a heavy chain variable region CDR2 of SEQ ID NO: 10; a heavy chain variable region CDR3 of SEQ ID NO: 11; a light chain variable region CDR1 of SEQ ID NO: 22; a light chain variable region CDR2 of SEQ ID NO: 23; and a light chain variable region CDR3 of SEQ ID NO: 24.

In a specific embodiment, provided herein is an antibody that specifically binds to GDF15 comprising a heavy chain variable region CDR1 of SEQ ID NO: 35; a heavy chain variable region CDR2 of SEQ ID NO: 36; a heavy chain variable region CDR3 of SEQ ID NO: 37; a light chain variable region CDR1 of SEQ ID NO: 48; a light chain variable region CDR2 of SEQ ID NO: 49; and a light chain variable region CDR3 of SEQ ID NO: 50.

In a specific embodiment, provided herein is an antibody that specifically binds to GDF15 comprising a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 74; a light chain variable region CDR2 of SEQ ID NO: 75; and a light chain variable region CDR3 of SEQ ID NO: 76.

In a specific embodiment, provided herein is an antibody that specifically binds to GDF15 comprising a heavy chain variable region CDR1 of SEQ ID NO: 87; a heavy chain variable region CDR2 of SEQ ID NO: 88; a heavy chain variable region CDR3 of SEQ ID NO: 89; a light chain variable region CDR1 of SEQ ID NO: 100; a light chain variable region CDR2 of SEQ ID NO: 101; and a light chain variable region CDR3 of SEQ ID NO: 102.

In a specific embodiment, provided herein is an antibody that specifically binds to GDF15 comprising a heavy chain variable region CDR1 of SEQ ID NO: 113; a heavy chain variable region CDR2 of SEQ ID NO: 114; a heavy chain variable region CDR3 of SEQ ID NO: 115; a light chain variable region CDR1 of SEQ ID NO: 126; a light chain variable region CDR2 of SEQ ID NO: 127; and a light chain variable region CDR3 of SEQ ID NO: 128.

In a specific embodiment, provided herein is an antibody that specifically binds to GDF15 comprising a heavy chain variable region CDR1 of SEQ ID NO: 139; a heavy chain variable region CDR2 of SEQ ID NO: 140; a heavy chain variable region CDR3 of SEQ ID NO: 141; a light chain variable region CDR1 of SEQ ID NO: 152; a light chain variable region CDR2 of SEQ ID NO: 153; and a light chain variable region CDR3 of SEQ ID NO: 154.

In a specific embodiment, provided herein is an antibody that specifically binds to GDF15 comprising a heavy chain variable region CDR1 of SEQ ID NO: 165; a heavy chain variable region CDR2 of SEQ ID NO: 166; a heavy chain variable region CDR3 of SEQ ID NO: 167; a light chain variable region CDR1 of SEQ ID NO: 178; a light chain variable region CDR2 of SEQ ID NO: 179; and a light chain variable region CDR3 of SEQ ID NO: 180.

In certain embodiments, provided herein are antibodies or antigen binding fragments that specifically bind to GDF15 as described in Table 1. In a particular embodiment, the antibody, or antigen binding fragment, that binds GDF15 is ABGDF15-A, ABGDF15-G, ABGDF15-B, ABGDF15-C, ABGDF15-F, ABGDF15-E, or ABGDF15-D.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below.

Homologous Antibodies

In yet another embodiment, provided herein is an antibody, or an antigen binding fragment thereof, comprising amino acid sequences that are homologous to the sequences described in Table 1, and the antibody binds to a GDF15 protein (e.g., human GDF15), and retains the desired functional properties of those antibodies described in Table 1.

For example, provided herein is an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 12, 38, 64, 90, 116, 142, 168; the light chain variable domain comprises an amino acid sequence that is at least 80%, at least 90%, or at least 95% identical to an amino acid sequence selected from the group consisting of SEQ ID NOs: 25, 51, 77, 103, 129, 155, 181; and the antibody specifically binds to GDF15 (e.g., human GDF15). In certain embodiments, the heavy and light chain sequences further comprise HCDR1, HCDR2, HCDR3, LCDR1, LCDR2, and LCDR3 sequences as defined by Kabat, for example SEQ ID NOs: 6, 7, 8, and 19, 20, 21, respectively. In certain other embodiments, the heavy and light chain sequences further comprise HCDR1, HCDR2, HCDR3, LCDR1, LCDR2, and LCDR3 sequences as defined by Chothia numbering, for example SEQ ID NOs: 9, 10, 11, and 22, 23, 24, respectively. In still certain other embodiments, the heavy and light chain sequences further comprise HCDR1, HCDR2, HCDR3, LCDR1, LCDR2, and LCDR3 sequences as defined by combining both Kabat and Chothia, for example SEQ ID NOs: 3, 4, 5, and 16, 17, 18, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 13, 39, 65, 91, 117, 143, 169 and SEQ ID NOs: 26, 52, 78, 104, 130, 156, 182, respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 14, 40, 66, 92, 118, 144, 170, and full length light chains of any of SEQ ID NOs: 27, 53, 79, 105, 131, 157, 183, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences described herein can further be used as a "query sequence" to perform a search against public databases to, for example, identify related sequences. For example, such searches can be performed using the BLAST program (version 2.0) of Altschul, et al., 1990 *J. Mol. Biol.* 215:403-10.

Antibodies with Conservative Modifications

In certain embodiments, an antibody described herein has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the GDF15-binding antibodies described herein.

Accordingly, provided herein is an antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 3, 29, 55, 81, 107, 133, and 159, and conservative modifications thereof; the heavy chain variable region CDR2 amino acid sequences are selected from the group consisting of SEQ ID NOs: 4, 30, 56, 82, 108, 134, and 160, and conservative modifications thereof; the heavy chain variable region CDR3 amino acid sequences are selected from the group consisting of SEQ ID NOs: 5, 31, 57, 83, 109, 135, and 161, and conservative modifications thereof; the light chain variable regions CDR1 amino acid sequences are selected from the group consisting of SEQ ID NOs: 16, 42, 68, 94, 120, 146, and 172, and conservative modifications thereof; the light chain variable regions CDR2 amino acid sequences are selected from the group consisting of SEQ ID NOs: 17, 43, 69, 95, 121, 147, and 173, and conservative modifications thereof; the light chain variable regions of CDR3 amino acid sequences are selected from the group consisting of SEQ ID NOs: 18, 44, 70, 96, 122, 148, and 174, and conservative modifications thereof; and the antibody or antigen binding fragments thereof specifically binds to GDF15.

Accordingly, provided herein is an antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 6, 32, 58, 84, 110, 136, and 162, and conservative modifications thereof; the heavy chain variable region CDR2 amino acid sequences are selected from the group consisting of SEQ ID NOs: 7, 33, 59, 85, 111, 137, and 163, and conservative modifications thereof; the heavy chain variable region CDR3 amino acid sequences are selected from the group consisting of SEQ ID NOs: 8, 34, 60, 86, 112, 138, and 164, and conservative modifications thereof; the light chain variable regions CDR1 amino acid sequences are selected from the group consisting of SEQ ID NOs: 19, 45, 71, 97, 123, 149, and 175, and conservative modifications thereof; the light chain variable regions CDR2 amino acid sequences are selected from the group consisting of SEQ ID NOs: 20, 46, 72, 98, 124, 150, and 176, and conservative modifications thereof; the light chain variable regions of CDR3 amino acid sequences are selected from the group consisting of SEQ ID NOs: 21, 47, 73, 99, 125, 151, and 177, and conservative modifications thereof; and the antibody or antigen binding fragments thereof specifically binds to GDF15.

Accordingly, provided herein is an antibody, or an antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 9, 35, 61, 87, 113, 139, and 165, and conservative modifications thereof; the heavy chain variable region CDR2 amino acid sequences are selected from the group consisting of SEQ ID NOs: 10, 36, 62, 88, 114, 140, and 166, and conservative modifications thereof; the heavy chain variable region CDR3 amino acid sequences are selected from the group consisting of SEQ ID NOs: 11, 37, 63, 89, 115, 141, and 167, and conservative modifications thereof; the light chain variable regions CDR1 amino acid sequences are selected from the group consisting of SEQ ID NOs: 22, 48, 74, 100, 126, 152, and 178, and conservative modifications thereof; the light chain variable regions CDR2 amino acid sequences are selected from the group consisting of SEQ ID NOs: 23, 49, 75, 101, 127, 153, and 179, and conservative modifications thereof; the light chain variable regions of CDR3 amino acid sequences are selected from the group consisting of SEQ ID NOs: 24, 50, 76, 102, 128, 154, and 180, and conservative modifications thereof; and the antibody or antigen binding fragments thereof specifically binds to GDF15.

In other embodiments, the antibody described herein is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the GDF15 binding antibodies described herein. Accordingly, provided herein is an isolated antibody optimized for expression in a mammalian cell consisting of a full length heavy chain and a full length light chain wherein the full length heavy chain has amino acid sequences selected from the group of SEQ ID NOs: 14, 40, 66, 92, 118, 144, and 170, and conservative modifications thereof; and the full length light chain has amino acid sequences selected from the group of SEQ ID NOs: 27, 53, 79, 105, 131, 157, and 183, and conservative modifications thereof; and the antibody specifically binds to GDF15 (e.g., human GDF15).

Antibodies that Bind to the Same Epitope

Provided herein are antibodies that bind to the same epitope as the GDF15 binding antibodies described in Table 1. Additional antibodies can therefore be identified based on their ability to compete (e.g., to competitively inhibit the binding of, in a statistically significant manner) with other antibodies described herein in GDF15 binding assays (such as those described in the Examples). The ability of a test antibody to inhibit the binding of antibodies described herein to a GDF15 protein demonstrates that the test antibody can compete with that antibody for binding to GDF15; such an antibody may, according to non-limiting theory, bind to the same or a related (e.g., a structurally similar or spatially proximal) epitope on the GDF15 protein as the antibody with which it competes. In a certain embodiment, the antibody that binds to the same epitope on GDF15 as the antibodies described herein is a human monoclonal antibody. Such human monoclonal antibodies can be prepared and isolated as described herein. As used herein, an antibody "competes" for binding when the competing antibody inhibits GDF15 binding of an antibody or antigen binding fragment described herein by more than 50% (for example, 80%, 85%, 90%, 95%, 98% or 99%) in the presence of an equimolar concentration of competing antibody.

Engineered and Modified Antibodies

An antibody described herein further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the disclosure pertains to an isolated antibody, or an antigen binding fragment thereof, comprising a heavy chain variable region comprising CDR1 sequences having an amino acid sequence selected from the group consisting of SEQ ID NOs: 6, 32, 58, 84, 110, 136, and 162; CDR2 sequences having an amino acid sequence selected from the group consisting of SEQ ID NOs: 7, 33, 59, 85, 111, 137, and 163; CDR3 sequences having an amino acid sequence selected from the group consisting of SEQ ID NOs: 8, 34, 60, 86, 112, 138, 164, respectively; and a light chain variable region having CDR1 sequences having an amino acid sequence selected from the group consisting of SEQ ID NOs: 19, 45, 71, 97, 123, 149, and 175; CDR2 sequences having an amino acid sequence selected from the group consisting of SEQ ID NOs: 20, 46, 72, 98, 124, 150, and 176; and CDR3 sequences consisting of an amino acid sequence selected from the group consisting of SEQ ID NOs: 21, 47, 73, 99, 125, 151, and 177, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies described herein are those that are structurally similar to the framework sequences used by selected antibodies described herein, e.g., consensus sequences and/or framework sequences used by monoclonal antibodies described herein. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.). Frameworks that can be utilized as scaffolds on which to build the antibodies and antigen binding fragments described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the disclosure relates to isolated GDF15 binding antibodies, or antigen binding fragments thereof, comprising a heavy chain variable region comprising an amino acid sequence selected from the group consisting of SEQ ID NOs: 12, 38, 64, 90, 116, 142, and 168, or an amino acid sequence having one, two, three, four or five amino acid substitutions, deletions or additions in the framework region of such sequences, and further comprising a light chain variable region having an amino acid sequence selected from the group consisting of SEQ ID NOs: 25, 51, 77, 103, 129, 155, and 181, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, provided herein is GDF15-binding antibodies, or antigen binding fragments thereof, consisting of a heavy chain variable region having a VH CDR1 region consisting of an amino acid sequence selected from the group having SEQ ID NOs: 3, 29, 55, 81, 107, 133, and 159 or an amino acid sequence having one, two, three, four or five amino acid substitutions, deletions or additions as compared to SEQ ID NOs: 3, 29, 55, 81, 107, 133, and 159; a VH CDR2 region having an amino acid sequence selected from the group consisting of SEQ ID NOs: 4, 30, 56, 82, 108, 134, and 160 or an amino acid sequence having one, two, three, four or five amino acid substitutions, deletions or additions as compared to SEQ ID NOs: 4, 30, 56, 82, 108, 134, and 160; a VH CDR3 region having an amino acid sequence selected from the group consisting of SEQ ID NOs: 5, 31, 57, 83, 109, 135, and 161, or an amino acid sequence having one, two, three, four or five amino acid substitutions, deletions or additions as compared to SEQ ID NOs: 5, 31, 57, 83, 109, 135, and 161; a VL CDR1 region having an amino acid sequence selected from the group consisting of SEQ ID NOs: 16, 42, 68, 94, 120, 146, and 172, or an amino acid sequence having one, two, three, four or five amino acid substitutions, deletions or additions as compared to SEQ ID NOs: 16, 42, 68, 94, 120, 146, and 172; a VL CDR2 region having an amino acid sequence selected from the group consisting of SEQ ID NOs: 17, 43, 69, 95, 121, 147, and 173, or an amino acid sequence having one, two, three, four or five amino acid substitutions, deletions or additions as compared to SEQ ID NOs: 17, 43, 69, 95, 121, 147, and 173; and a VL CDR3 region having an amino acid sequence selected from the group consisting of SEQ ID NOs: 18, 44, 70, 96, 122, 148, and 174, or an amino acid sequence having one, two, three, four or five amino acid substitutions, deletions or additions as compared to SEQ ID NOs: 18, 44, 70, 96, 122, 148, and 174.

Accordingly, in another embodiment, provided herein are GDF15-binding antibodies, or antigen binding fragments thereof, consisting of a heavy chain variable region having a VH CDR1 region consisting of an amino acid sequence selected from the group having SEQ ID NOs: 6, 32, 58, 84, 110, 136, and 162 or an amino acid sequence having one, two, three, four or five amino acid substitutions, deletions or additions as compared to SEQ ID NOs: 6, 32, 58, 84, 110, 136, and 162; a VH CDR2 region having an amino acid sequence selected from the group consisting of SEQ ID NOs: 7, 33, 59, 85, 111, 137, and 163 or an amino acid sequence having one, two, three, four or five amino acid substitutions, deletions or additions as compared to SEQ ID NOs: 7, 33, 59, 85, 111, 137, and 163; a VH CDR3 region having an amino acid sequence selected from the group consisting of SEQ ID NOs: 8, 34, 60, 86, 112, 138, and 164, or an amino acid sequence having one, two, three, four or five amino acid substitutions, deletions or additions as compared to SEQ ID NOs: 8, 34, 60, 86, 112, 138, and 164; a VL CDR1 region having an amino acid sequence selected from the group consisting of SEQ ID NOs: 19, 45, 71, 97, 123, 149, and 175, or an amino acid sequence having one, two, three, four or five amino acid substitutions, deletions or additions as compared to SEQ ID NOs: 19, 45, 71, 97, 123, 149, and 175; a VL CDR2 region having an amino acid sequence selected from the group consisting of SEQ ID NOs: 20, 46, 72, 98, 124, 150, and 176, or an amino acid sequence having one, two, three, four or five amino acid substitutions, deletions or additions as compared to SEQ ID NOs: 20, 46, 72, 98, 124, 150, and 176; and a VL CDR3 region having an amino acid sequence selected from the group consisting of SEQ ID NOs: 21, 47, 73, 99, 125, 151, and 177, or an amino acid sequence having one, two, three, four or five amino acid substitutions, deletions or additions as compared to SEQ ID NOs: 21, 47, 73, 99, 125, 151, and 177.

Accordingly, in another embodiment, provided herein is GDF15-binding antibodies, or antigen binding fragments thereof, consisting of a heavy chain variable region having a VH CDR1 region consisting of an amino acid sequence selected from the group having SEQ ID NOs: 9, 35, 61, 87, 113, 139, and 165 or an amino acid sequence having one, two, three, four or five amino acid substitutions, deletions or additions as compared to SEQ ID NOs: 9, 35, 61, 87, 113, 139, and 165; a VH CDR2 region having an amino acid sequence selected from the group consisting of SEQ ID NOs: 10, 36, 62, 88, 114, 140, and 166 or an amino acid sequence having one, two, three, four or five amino acid substitutions, deletions or additions as compared to SEQ ID NOs: 10, 36, 62, 88, 114, 140, and 166; a VH CDR3 region having an amino acid sequence selected from the group consisting of SEQ ID NOs: 11, 37, 63, 89, 115, 141, and 167, or an amino acid sequence having one, two, three, four or five amino acid substitutions, deletions or additions as compared to SEQ ID NOs: 11, 37, 63, 89, 115, 141, and 167; a VL CDR1 region having an amino acid sequence selected from the group consisting of SEQ ID NOs: 22, 48, 74, 100, 126, 152, 178, or an amino acid sequence having one, two, three, four or five amino acid substitutions, deletions or additions as compared to SEQ ID NOs: 22, 48, 74, 100, 126, 152, and 178; a VL CDR2 region having an amino acid sequence selected from the group consisting of SEQ ID NOs: 23, 49, 75, 101, 127, 153, 179, or an amino acid sequence having one, two, three, four or five amino acid substitutions, deletions or additions as compared to SEQ ID NOs: 23, 49, 75, 101, 127, 153, and 179; and a VL CDR3 region having an amino acid sequence selected from the group consisting of SEQ ID NOs: 24, 50, 76, 102, 128, 154, and 180, or an amino acid sequence having one, two, three, four or five amino acid substitutions, deletions or additions as compared to SEQ ID NOs: 24, 50, 76, 102, 128, 154, and 180.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to GDF15. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs described herein can be grafted. Known or future non-immunoglobulin frameworks and scaffolds may be employed, as long as they comprise a binding region specific for the target GDF15 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs described herein using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (see e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

Provided herein are fully human antibodies that specifically bind to a GDF15 protein. Compared to the chimeric or humanized antibodies, the human GDF15-binding antibodies described herein have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 *J Biol Chem* 279: 1256-1261; Dumoulin, M. et al., 2003 *Nature* 424: 783-788; Pleschberger, M. et al. 2003 *Bioconjugate Chem* 14: 440-448; Cortez-Retamozo, V. et al. 2002 *Int J Cancer* 89: 456-62; and Lauwereys, M. et al. 1998 *EMBO J* 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized" Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present disclosure is a camelid antibody or nanobody having high affinity for GDF15. In certain embodiments herein, the camelid antibody or nanobody is naturally produced in the camelid animal, i.e., is produced by the camelid following immunization with GDF15 or a peptide fragment thereof, using techniques described herein for other antibodies. Alternatively, the GDF15-binding camelid nanobody is engineered, i.e., produced by selection for example from a library of phage displaying appropriately mutagenized camelid nanobody proteins using panning procedures with GDF15 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies described herein into nanobody or single domain antibody framework sequences, as described for example in PCT/EP93/02214 published as WO94/04678.

Bispecific Molecules and Multivalent Antibodies

In another aspect, the present disclosure features bispecific or multispecific molecules comprising a GDF15-binding antibody, or a fragment thereof, described herein. An antibody described herein, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for GDF15 and a second binding specificity for a second target epitope. For example, the second target epitope is another epitope of GDF15 different from the first target epitope.

Additionally, for the disclosure in which the bispecific molecule is multi-specific, the molecule can further include a third binding specificity, in addition to the first and second target epitope.

In one embodiment, the bispecific molecules described herein comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 *Proc. Natl. Acad. Sci. USA* 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 *Cancer Immunol. Immunother.*, 45(3-4):128-30; Wu et al., 1996 *Immunotechnology*, 2(1):21-36). scDb can be expressed in bacteria in soluble, active monomeric form (see Holliger and Winter, 1997 *Cancer Immunol. Immunother.*, 45(34): 128-30; Wu et al., 1996 *Immunotechnology*, 2(1):21-36; Pluckthun and Pack, 1997 *Immunotechnology*, 3(2): 83-105; Ridgway et al., 1996 *Protein Eng.*, 9(7):617-21). A diabody can be fused to Fc to generate a "di-diabody" (see Lu et al., 2004 *J. Biol. Chem.*, 279(4):2856-65).

Other antibodies which can be employed in the bispecific molecules described herein are murine, chimeric and human monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 *J. Exp. Med.* 160:1686; Liu, M A et al., 1985 *Proc. Natl. Acad. Sci. USA* 82:8648). Other methods include those described in Paulus, 1985 Behring Ins. Mitt. No. 78, 118-132; Brennan et al., 1985 *Science* 229:81-83), and Glennie et al., 1987 *J. Immunol.* 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, provided herein are multivalent compounds comprising at least two identical or different antigen-binding portions of the antibodies described herein binding to GDF15. The antigen-binding portions can be linked together via protein fusion or covalent or non covalent linkage. Alternatively, methods of linkage have been described for the bispecfic molecules. Tetravalent compounds can be obtained for example by cross-linking antibodies of the antibodies described herein with an antibody that binds to the constant regions of the antibodies described herein, for example the Fc or hinge region.

Trimerizing domain are described for example in Borean patent EP 1012280B1. Pentamerizing modules are described for example in PCT/EP97/05897 published as WO 98/18973.

Antibodies with Extended Half Life

Provided herein are antibodies that specifically bind to GDF15 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies described herein. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies described herein. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to GDF15 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

Provided herein are antibodies or fragments thereof that specifically bind to a GDF15 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, provided herein are fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies described herein or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a GDF15 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies described herein or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; and positron emitting metals using various positron emission tomographies, and noradioactive paramagnetic metal ions.

The present disclosure further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alph-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraaza-cyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4(10): 2483-90; Peterson et al., 1999, *Bioconjug. Chem.* 10(4):553-7; and Zimmerman et al., 1999, *Nucl. Med. Biol.* 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, *Immunol. Rev.* 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies

Nucleic Acids Encoding the Antibodies

Provided herein are substantially purified nucleic acid molecules which encode polypeptides comprising segments or domains of the GDF15-binding antibody chains described above. Some of the nucleic acids described herein comprise the nucleotide sequence encoding the heavy chain variable region shown in SEQ ID NO: 13, 39, 65, 91, 117, 143, or 169, and/or the nucleotide sequence encoding the light chain variable region shown in SEQ ID NO: 26, 52, 78, 104, 130, 156, or 182. In a specific embodiment, the nucleic acid molecules are those identified in Table 1. Some other nucleic acid molecules described herein comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting GDF15 antigen binding capacity.

Also provided herein are polynucleotides which encode at least one CDR region and usually all three CDR regions from the heavy or light chain of the GDF15-binding antibody set forth above. Some other polynucleotides encode all or substantially all of the variable region sequence of the heavy chain and/or the light chain of the GDF15-binding antibody set forth above. Because of the degeneracy of the code, a variety of nucleic acid sequences will encode each of the immunoglobulin amino acid sequences.

The nucleic acid molecules described herein can encode both a variable region and a constant region of the antibody. Some of nucleic acid sequences described herein comprise nucleotides encoding a heavy chain sequence that is substantially identical (e.g., at least 80%, 90%, or 99%) to the heavy chain sequence set forth in SEQ ID NO: 14, 40, 66, 92, 118, 144, 170. Some other nucleic acid sequences comprising nucleotide encoding a light chain sequence that is substantially identical (e.g., at least 80%, 90%, or 99%) to the light chain sequence set forth in SEQ ID NO: 27, 53, 79, 105, 131, 157, or 183.

The polynucleotide sequences can be produced by de novo solid-phase DNA synthesis or by PCR mutagenesis of an existing sequence (e.g., sequences as described in the Examples below) encoding a GDF15-binding antibody or its binding fragment. Direct chemical synthesis of nucleic acids can be accomplished by methods known in the art, such as the phosphotriester method of Narang et al., 1979, *Meth. Enzymol.* 68:90; the phosphodiester method of Brown et al., *Meth. Enzymol.* 68:109, 1979; the diethylphosphoramidite method of Beaucage et al., *Tetra. Lett.,* 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., *Nucleic Acids Res.* 19:967, 1991; and Eckert et al., *PCR Methods and Applications* 1:17, 1991.

Also provided herein are expression vectors and host cells for producing the GDF15-binding antibodies described above. Various expression vectors can be employed to express the polynucleotides encoding the GDF15-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the GDF15-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, *Annu. Rev. Microbiol.* 49:807, 1995; and Rosenfeld et al., *Cell* 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a GDF15-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a GDF15-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Enzymol.*, 153:516, 1987). For example, the SV40 enhancer or CMV enhancer may be used to increase expression in mammalian host cells.

The expression vectors may also provide a secretion signal sequence position to form a fusion protein with polypeptides encoded by inserted GDF15-binding antibody sequences. More often, the inserted GDF15-binding antibody sequences are linked to a signal sequences before inclusion in the vector. Vectors to be used to receive sequences encoding GDF15-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the GDF15-binding antibody chains can be either prokaryotic or eukaryotic. *E. coli* is one prokaryotic host useful for cloning and expressing the polynucleotides described herein. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express GDF15-binding polypeptides described herein. Insect cells in combination with baculovirus vectors can also be used.

In some preferred embodiments, mammalian host cells are used to express and produce the GDF15-binding polypeptides described herein. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223, 1997), agent-enhanced uptake of DNA, and ex vivo transduction. For long-term, high-yield production of recombinant proteins, stable expression will often be desired. For example, cell lines which stably express GDF15-binding antibody chains or binding fragments can be prepared using expression vectors described herein which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Framework or Fc Engineering

Engineered antibodies described herein include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the disclosure.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Application Publication No. 20030153043 by Carr et al.

In addition or alternative to modifications made within the framework or CDR regions, antibodies described herein may be engineered to include modifications within the Fc region, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al., 2001 *J. Biol. Chen.* 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen.". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 *J. Biol. Chem.* 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 *Nat. Biotech.* 17:176-180).

Methods of Engineering Altered Antibodies

As discussed above, the GDF15-binding antibodies having VH and VL sequences or full length heavy and light chain sequences shown herein can be used to create new GDF15-binding antibodies by modifying full length heavy chain and/or light chain sequences, VH and/or VL sequences, or the constant region(s) attached thereto. Thus, in another aspect, the structural features of a GDF15-binding antibody described herein are used to create structurally related GDF15-binding antibodies that retain at least one functional property of the antibodies described herein, such as binding to human GDF15 and also inhibiting one or more functional properties of GDF15 (e.g., inhibiting GDF15 binding to the GDF15 receptor, depleting free GDF15 from circulation).

For example, one or more CDR regions of the antibodies described herein, or mutations thereof, can be combined recombinantly with known framework regions and/or other CDRs to create additional, recombinantly-engineered, GDF15-binding antibodies described herein, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, provided herein is a method for preparing a GDF15-binding antibody consisting of a heavy chain variable region antibody sequence having a CDR1 sequence selected from the group consisting of SEQ ID NOs: 3, 29, 55, 81, 107, 133, or 159, a CDR2 sequence selected from the group consisting of SEQ ID NOs: 4, 30, 56, 82, 108, 134, or 160, and/or a CDR3 sequence selected from the group consisting of SEQ ID NOs: 5, 31, 57, 83, 109, 135, or 161; and a light chain variable region antibody sequence having a CDR1 sequence selected from the group consisting of SEQ ID NOs: 16, 42, 68, 94, 120, 146, or 172, a CDR2 sequence selected from the group consisting of SEQ ID NOs: 17, 43, 69, 95, 121, 147, or 173, and/or a CDR3 sequence selected from the group consisting of SEQ ID NOs: 18, 44, 70, 96, 122, 148, or 174; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, provided herein is a method for preparing a GDF15-binding antibody consisting of a heavy chain variable region antibody sequence having a CDR1 sequence selected from the group consisting of SEQ ID NOs: 6, 32, 58, 84, 110, 136, or 162, a CDR2 sequence selected from the group consisting of SEQ ID NOs: 7, 33, 59, 85, 111, 137, or 163, and/or a CDR3 sequence selected from the group consisting of SEQ ID NOs: 8, 34, 60, 86, 112, 138, or 164; and a light chain variable region antibody sequence having a CDR1 sequence selected from the group consisting of SEQ ID NOs: 19, 45, 71, 97, 123, 149, or 175, a CDR2 sequence selected from the group consisting of SEQ ID NOs: 20, 46, 72, 98, 124, 150, or 176, and/or a CDR3 sequence selected from the group consisting of SEQ ID NOs: 21, 47, 73, 99, 125, 151, or 177; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, provided herein is a method for preparing a GDF15-binding antibody consisting of a heavy chain variable region antibody sequence having a CDR1 sequence selected from the group consisting of SEQ ID NOs: 9, 35, 61, 87, 113, 139, or 165, a CDR2 sequence selected from the group consisting of SEQ ID NOs: 10, 36, 62, 88, 114, 140, or 166, and/or a CDR3 sequence selected from the group consisting of SEQ ID NOs: 11, 37, 63, 89, 115, 141, or 167; and a light chain variable region antibody sequence having a CDR1 sequence selected from the group consisting of SEQ ID NOs: 22, 48, 74, 100, 126, 152, or 178, a CDR2 sequence selected from the group consisting of SEQ ID NOs: 23, 49, 75, 101, 127, 153, or 179, and/or a CDR3 sequence selected from the group consisting of SEQ ID NOs: 24, 50, 76, 102, 128, 154, or 180; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, provided herein is a method for preparing a GDF15-binding antibody optimized for expression in a mammalian cell consisting of: a full length heavy chain antibody sequence having a sequence selected from the group of SEQ ID NOs: 14, 40, 66, 92, 118, 144, or 170; and a full length light chain antibody sequence having a sequence selected from the group of 27, 53, 79, 105, 131, 157, or 183; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the GDF15-binding antibodies described herein, which functional properties include, but are not limited to, specifically binding to human, cynomolgus, rat, and/or mouse GDF15; and the antibody inhibit GDF15-dependent cell proliferation in a F36E and/or Ba/F3-GDF15R cell proliferation assay.

In certain embodiments of the methods of engineering antibodies described herein, mutations can be introduced randomly or selectively along all or part of an GDF15- binding antibody coding sequence and the resulting modified GDF15-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments, antibodies have been engineered to remove sites of deamidation. Deamidation is known to cause structural and functional changes in a peptide or protein. Deamindation can result in decreased bioactivity, as well as alterations in pharmacokinetics and antigenicity of the protein pharmaceutical. (*Anal Chem.* 2005 Mar. 1; 77(5):1432-9).

In certain embodiments, the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-GDF15 antibodies, or Fabs, described herein improved their solubility, enabling the antibodies to be formulated at higher concentrations (>100 mg/ml). Formulation of the antibodies at high concentrations (e.g., >100 mg/ml) offers the advantage of being able to administer higher doses of the antibodies into eyes of patients via intravitreal injections, which in turn may enable reduced dosing frequency, a significant advantage for treatment of chronic diseases including wasting disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that bind GDF15 as described herein (e.g., ABGDF15-A, ABGDF15-B, ABGDF15-C, ABGDF15-D, ABGDF15-E, ABGDF15-F, or ABGDF15-G), can be used at a therapeutically useful concentration for the treatment of a disease or disorder associated with GDF15 by administering to a subject in need thereof an effective amount of the antibodies or antigen binding fragments described herein.

The antibodies disclosed herein can be used, inter alia, to prevent treat, prevent, and improve GDF15 associated conditions or disorders. These conditions include but are not limited to those involving wasting disorders such as anorexia cachexia, anorexia of the aged, anorexia nervosa, cachexia associated with cancer, cachexia associated with AIDS, cachexia associated with heart failure, cachexia associated with cystic fibrosis, cachexia associated with rheumatoid arthritis, cachexia associated with kidney disease, cachexia associated with COPD, cachexia associated with ALS, cachexia associated with renal failure or cachexia associated with hip fracture, and the like.

Accordingly, provided herein is a method of treating GDF15-associated disorders, e.g., wasting disorders such as cachexia or sarcopenia by administering to a subject in need thereof an effective amount of the antibodies described herein. Provided herein is a method of treating GDF15-associated disorders by administering to a subject in need thereof an effective amount of the antibodies described herein. Other GDF15-associated diseases or disorders associated with or resulting from elevated GDF15 levels include sarcopenia, i.e., a clinical condition related to cachexia that is characterized by loss of skeletal muscle mass and muscle strength; and starvation. Starvation typically results in a loss of body fat and non-fat mass due to inadequate diet and/or nutritional uptake (Thomas (2007) *Clinical Nutrition* 26:389-399). The effects of starvation often are reversed by improving diet and nutritional, for example, protein, uptake. Still other GDF15-associated diseases or disorders associated with or resulting from elevated GDF15 levels include, but are not limited to, disorders associated with aberrant appetite, fat mass, energy balance, and/or involuntary weight loss, and reduced mortality and morbidity of critically ill patients.

In some embodiments, antibodies disclosed herein can be used to treat any number of conditions or diseases in which the GDF15 protein levels are aberrantly high and/or in which a reduction of GDF15 protein levels is sought. In embodiments, the subject has an elevated circulating level of GDF15, e.g., elevated serum GDF15 levels. For example, a subject afflicted by tumors over-expressing and/or secreting GDF15, and/or a subject afflicted with a cancer associated with elevated serum GDF15 levels, can be treated. Exemplary disorders showing elevated serum GDF15 levels include, but are not limited to, beta-thalassemia, pulmonary embolism, cancer, e.g., prostate, colorectal, pancreatic cancer, severe chronic kidney disease, Anorexia Nervosa, chronic heart failure, obesity, burn patients, and pregnancy. In specific aspects, provided herein are methods of increasing appetite, food intake, body weight and/or muscle mass in a subject in need thereof, said method comprising administering to the subject an effective amount of an anti-GDF15 antibody described herein (e.g., ABGDF15-A, ABGDF15-B, ABGDF15-C, ABGDF15-D, ABGDF15-E, ABGDF15-F, or ABGDF15-G as set out in Table 1). In specific aspects, the subject has been diagnosed with a wasting disorder (e.g., cachexia). In particular embodiments, the subject has been diagnosed with cancer, chronic heart failure, chronic kidney disease, COPD, AIDS, multiple sclerosis, rheumatoid arthritis, sepsis, or tuberculosis. In specific embodiments, the condition/disorder is associated with elevated levels of GDF15, for example, relative to GDF15 levels in a population of healthy subjects.

In particular aspects, provided herein are method of inhibiting or reducing loss of body weight, muscle mass, appetite, or food intake, in a subject in need thereof, said method comprising administering to the subject an effective amount of an anti-GDF15 antibody described herein (e.g., ABGDF15-A, ABGDF15-B, ABGDF15-C, ABGDF15-D, ABGDF15-E, ABGDF15-F, or ABGDF15-G as set out in Table 1). In specific aspects, the subject has been diagnosed with a wasting disorder (e.g., cachexia). In particular embodiments, the subject has been diagnosed with cancer, chronic heart failure, chronic kidney disease, COPD, AIDS, multiple sclerosis, rheumatoid arthritis, sepsis, or tuberculosis. In specific embodiments, the condition/disorder is associated with elevated levels of GDF15, for example, relative to GDF15 levels in a population of healthy subjects. The antibodies disclosed herein can also be used in combination with other agents for the prevention, treatment, or improvement of GDF15 associated disorders. For example, TNFα and IL-1 are cytokines known to be involved in mediation of the proinflammatory response, and which are also implicated in muscle depletion, anorexia and cachexia; therefore, inhibitors of TNFα and/or IL-1 may be used in combination with the GDF15 antibodies and antigen binding fragments described herein for the treatment of patients with GDF15-related disorders (e.g., wasting conditions).

Exemplary disorders are described in more detail below.

The antibodies disclosed herein can be used to treat a variety of disorders, for example, disorders associated with involuntary loss of weight or body mass, e.g., a wasting disorder. In some embodiment, the disorder is a metabolic disorder. In embodiments, the disorder is chosen from cachexia, sarcopenia or starvation. In some embodiments, the antibodies disclosed herein are used to inhibit the loss of muscle mass, for example, the loss of muscle mass associated with an underlying disease. In embodiments, the disorder associated with loss of body weight or body mass include, but are not limited to, cancer, cardiovascular disease (e.g., chronic heart failure), kidney disease (e.g., chronic kidney disease), COPD, AIDS, multiple sclerosis, rheumatoid arthritis, sepsis, or tuberculosis. In one embodiment, the disorder is a Cancer Anorexia-Cachexia Syndrome (CACS).

When administered to a subject, the antibodies disclosed herein can inhibit the loss of muscle mass, for example, the loss of muscle mass associated with an underlying disease. The underlying disease can be selected from the group consisting of cancer, chronic heart failure, chronic kidney disease, COPD, AIDS, multiple sclerosis, rheumatoid arthritis, sepsis, and tuberculosis. In some embodiments, the loss of muscle mass may be accompanied by a loss of fat mass. The disclosed antibodies can also be used to inhibit involuntary weight loss in a mammal. In some embodiments, the disclosed antibodies may also be used to inhibit the loss of organ mass. Further, a method of treating cachexia and/or sarcopenia in a subject comprising administering an effective amount of one or more of the disclosed antibodies to a subject in need thereof is disclosed.

In some embodiments, the disclosed antibodies inhibit a loss of muscle and/or fat mass by at least 20%, 30%, 40%, 50%, 60%, 70%, 80%, 90%, 95%, 98%, 99%, or 100%. In some embodiments, the disclosed antibodies inhibit loss of organ mass by at least 20%, 30%, 40%, 50%, 60%, 70%, 80%, 90%, 95%, 98%, 99%, or 100%. In some embodiments, loss of organ mass is observed in heart, liver, kidney, and/or spleen. In some embodiments, the loss of organ mass in accompanied by a loss of muscle mass, a loss of fat mass and/or involuntary weight loss.

Involuntary weight loss can be categorized into three primary etiologies that include cachexia, sarcopenia and starvation, described below.

Cachexia is a wasting/metabolic disorder involving involuntary weight loss that may be associated with numerous diseases, including cancer, AIDS, chronic heart failure (also known as congestive heart failure), chronic obstructive pulmonary disease (COPD), chronic kidney disease, tuberculosis, sepsis, systemic inflammation and/or an acute inflammatory response. (Thomas (2007) *Clin. Nutr* 26: 389-399). Cachexia varies in its manifestations, but generally involves involuntary loss of skeletal muscle mass and some form of underlying illness (Evans et al. (2008) *Clin. Nutr.* 27: 793-799). Loss of fat mass and muscle mass is a prominent clinical feature of cachexia. In several cases, cachexia progresses through stages that have been designated precachexia, cachexia and refractory cachexia (Fearon et al. (2011) *Lancet Onc.* 12: 489-495). Two different, but sometimes overlapping, processes appear to be involved in the development and progression of cachexia: (a) metabolic processes that act directly on muscle, reducing its mass and function; and (b) reduced food intake, which leads to loss of both fat and muscle (Tsai et al. (2012) *J. Cachexia Sarcopenia Muscle* 3:239-243). Weight loss resulting from cachexia is associated with poor prognosis in various diseases (Evans et al., supra), and cachexia and its consequences are considered to be the direct cause of death in about 20% of cancer deaths (Tisdale (2002) *Nat. Rev. Cancer* 2:862-871).

Sarcopenia is a clinical condition related to cachexia that is characterized by loss of skeletal muscle mass and muscle strength. The decrease in muscle mass can lead to functional impairment, with loss of strength, increased likelihood of falls, and loss of autonomy. Respiratory function may also be impaired with a reduced vital capacity. During metabolic stress, muscle protein is rapidly mobilized in order to provide the immune system, liver and gut with amino acids, particularly glutamine. Sarcopenia is often a disease of the elderly; however, its development may also be associated with muscle disuse and malnutrition, and may coincide with cachexia. Sarcopenia can be diagnosed based upon functional observations such as low muscle weight and low gait speed. See, e.g., Muscaritoli et al. (2010) *Clin. Nutrition* 29: 154-159. In certain embodiments, therefore, one or more of the anti-GDF antibodies disclosed herein can be used to treat a subject suffering from, or who has been diagnosed with, sarcopenia, a muscle wasting disorder and/or significant muscle weight loss, whether or not the subject has, or has been diagnosed with, cachexia or decreased appetite. Such a method comprises administering a therapeutically effective amount of one or more antibodies disclosed herein to the subject in need thereof.

Cancers

In embodiments, the antibodies disclosed herein can be used to treat a subject having a cancer associated with progressive or involuntary weight loss. Advanced cancer patients can experience progressive weight loss associated with anorexia, malnutrition, anemia, inflammation and suppression of immune functions. Collectively, this series of complex and inter-related symptoms have been described as Cancer Anorexia-Cachexia Syndrome (CACS). CACS is associated with muscle and fat mass loss, decreased quality of life, reduced response to anti-cancer therapies, increased treatment toxicity and reduced survival. Further, certain chemotherapeutic treatments used to treat various cancers have been shown to induce or contribute to cachexia. For example, subjects treated with platinum-based therapies, such as carboplatin and oxaliplatin, may experience dose-limiting, harmful, and sometimes fatal cachexia.

Examples of anti-cancer agents whose treatment and effects can benefit from combination with one or more anti-GDF15 antibodies are platinum-based therapeutics such as cisplatin, carboplatin and oxaliplatin. Other anti-cancer agents whose treatment and effects can benefit from combination with one or more anti-GDF15 antibodies include: capecitabine, doxorubicin, and gemcitabine.

The methods disclosed herein may also be useful for enhanced therapeutic treatment regimens and/or increase of overall survival in subjects treated with other anti-cancer agents, including alkylating agents, antimetabolites, antitumor antibiotics, topoisomerase inhibitors, mitotic inhibitors, corticosteroids, targeted therapies, hormone therapy, immunotherapy, and cancer vaccines.

Accordingly, the use of an anti-GDF15 antibody, in combination with one or more anti-cancer agents is disclosed.

Exemplary anti-cancer agents include, but are not limited to: anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-4S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB lestaurtinib (CEP-701), neratinib (HKI-272), nilotinib (TASIGNA®), semaxanib (semaxinib, SUM16), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib.

Exemplary indications for the methods disclosed herein include the following tumors and cancers: breast cancer; lung cancer (including small cell and non-small cell lung cancer); anal, colon, rectal and colorectal cancer; liver cancer; kidney and renal cancer (including renal cell carcinoma); head and neck cancer; pancreatic cancer; bone cancer; cervical, ovarian, vaginal and vulvar cancer; prostate, penile and testicular cancer; anal cancer; bladder cancer; leukemia (including AML; CML; ALL and CLL); stomach cancer (including gastrointestinal stromal tumors) and gastric cancer; brain tumors; gliomas; neuroblastomas and retinoblastomas; thyroid cancer; skin cancer (including melanoma); multiple myeloma (and other plasma cell neoplasms); lymphoma (including Hodgkin's and non-Hodgkin's); sarcoma; myeloproliferative neoplasms; malignant mesothelioma; adult/childhood soft tissue sarcoma; AIDS related Kaposi Sarcoma; endometrial cancer; gestational trophoblastic disease; malignant mesothelioma; multicentric Castleman Disease; myeloproliferative neoplasms; rhabdomyosarcoma; basal cell carcinoma; Wilms tumor and other childhood kidney cancers.

In certain embodiments, one or more anti-cachexia agents can be used in addition to the antibodies disclosed herein. Anti-cachexia agents that may be useful include megestrol acetate (Agiles et al. (2013) *Clinical Nutrition* 32:319-324); corticosteroids or glucocorticoids (such as dexamethasone, prednisone, methyl prednisolone); cannabinoids (such as dronabinol); ghrelin and anamorelin; melanocortin antagonists; anti-IL6 monoclonal antibodies; selective androgen receptor modulators (SARS); thalidomide; oxandrolone; activin receptor II; GDF8 (myostatin); and IL-la inhibitors.

In certain embodiments, the subject is treated with capecitabine (for example, Xeloda®) for cancer of the colon or rectum that has spread to other parts of the body (metastatic colorectal cancer), or cancer of the colon after surgery. Prior to, concomitant with, or subsequent to treatment with capecitabine, the subject is treated with anti-GDF 15 antibody as described herein.

In other embodiments, the subject is treated with capecitabine in combination with, or after treatment with, docetaxel (e.g., Taxotere®) for breast cancer that has spread to other parts of the body (metastatic breast cancer). Prior to, concomitant with, or subsequent to treatment with capecitabine, the subject is treated with anti-GDF15 antibody as described herein. Dosage and administration of capecitabine may be determined by the skilled clinician. A typical regimen may comprise administration of 1250 mg/ml$^2$ administered orally twice per day for two weeks, followed by a one week resting period, as a three week cycle. When used in combination with docetaxel, a typical regimen for docetaxel is 75 mg/ml$^2$ as one hour intravenous infusion every 3 weeks.

In certain embodiments, the subject is treated with gemcitabine (for example, Gemzar®), for pancreatic cancer; for ovarian in combination with carboplatin; for breast cancer in combination with paclitaxel; for non-small cell lung cancer (NSCLC) in combination with cisplatin. Prior to, concomitant with, or subsequent to treatment with gemcitabine, the subject is treated with anti-GDF15 antibody as described herein. Dosage and administration of gemcitabine may be determined by the skilled clinician. A typical regimen may comprise administration of between 1000 and 1250 mg/ml$^2$ administered intravenously over 30 minutes on days 1 and 8 of each 21 day cycle; or days 1, 8 and 15 of each 28 day cycle.

In certain embodiments, the subject is treated with doxorubicin (for example, Adriamycin®) for cancer of the colon or rectum that has spread to other parts of the body (metastatic colorectal cancer), or cancer of the colon after surgery. Prior to, concomitant with, or subsequent to treatment with capecitabine, the subject is treated with anti-GDF15 antibody as described herein.

Doxorubicin (for example Doxil®) is also approved for treatment of ovarian cancer, AIDS-related Kaposi's Sarcoma; and multiple myeloma, in combination with bortezomib, as well as for acute lymphoblastic lymphoma (ALL); acute myeloblasts lymphoma (AML); neuroblastoma; breast carcinoma; ovarian carcinoma; Hodgkin's Disease; malignant lymphoma; and bronchogenic carcinoma in which the small cell type is the most responsive compared to other cell types. Prior to, concomitant with, or subsequent to treatment with doxorubicin, the subject is treated with anti-GDF antibody as described herein. Dosage and administration of doxorubicin may be determined by the skilled clinician. A typical regimen may comprise administration of between 50 mg/ml$^2$ administered intravenously every 4 weeks, for four courses minimum (ovarian cancer); 20 mg/ml$^2$ administered intravenously every three weeks for treatment of AIDS-related Kaposi's Sarcoma. In multiple myeloma, a typical regimen is administration of bortezomib at 1.3 mg/ml$^2$, administered as an intravenous bolus injection on days 1, 4, 8 and 11 every 3 weeks, and administration of doxorubicin at 30 mg/ml$^2$, administered intravenously on day 4 following the administration of bortezomib.

In certain embodiments, the subject is treated with carboplatin, for example, Paraplatin®, for ovarian cancer. In other embodiments, the subject is treated with carboplatin in combination with, or after treatment with cyclophosphamide for advanced ovarian cancer. Prior to, concomitant with, or subsequent to treatment with carboplatin, the subject is treated with anti-GDF 15 antibody as described herein. Dosage and administration of carboplatin may be determined by the skilled clinician. A typical regimen may comprise administration 300-360 mg/ml$^2$ intravenous on day 1 every 4 weeks for approximately 6 cycles. When cyclophosphamide is co-administered, a typical regimen may be 300 mg/ml$^2$ intravenous infusion of carboplatin one day every 4 weeks for 6 cycles, combined with 600 mg/ml$^2$ intravenous infusion of cyclophosphamide one day every 4 weeks for 6 cycles.

In certain embodiments, the subject is treated with cisplatin, for example, Platinol®, for the treatment of metastatic testicular tumors, metastatic ovarian tumors, or advanced bladder cancer. In other embodiments, the subject is treated with cisplatin in combination with, or after treatment with cyclophosphamide Prior to, concomitant with, or subsequent to treatment with cisplatin, the subject is treated with anti-GDF15 antibody as described herein. Dosage and administration of cisplatin may be determined by the skilled clinician. A typical regimen may comprise administration 20 mg/ml$^2$ intravenous daily for 5 days per cycle for metastatic testicular tumors. For advanced bladder cancer, a typical regimen for cisplatin may comprise 50-70 mg/ml$^2$ intravenous infusion once every 3 to 4 weeks, depending upon the extent of prior exposure to radiation therapy and/or prior chemotherapy. For heavily pretreated patients, a dose of 50 mg/ml$^2$ intravenous once every 4 weeks is typical. For treatment of metastatic ovarian tumors, 75 to 100 mg/ml$^2$ intravenous per cycle once every 4 weeks is typical. When cisplatin administration is combined with cyclophosphamide, cisplatin injection and cyclophosphamide should be administered sequentially. A typical regimen may be 600 mg/ml$^2$ intravenous infusion of cyclophosphamide on day 1 every 4 weeks.

In certain embodiments, the subject is treated with oxaliplatin, for example Eloxatin®, in combination with 5-fluorouracil and/or leucovorin, for treatment of cancer of the colon or advanced colorectal cancer, or cancer of the colon after surgery. Prior to, concomitant with, or subsequent to treatment with oxaliplatin, the subject is treated with anti-GDF15 antibody as described herein. Dosage and administration of oxaliplatin may be determined by the skilled clinician. A typical regimen may comprise administration 85 mg/ml$^2$ intravenous infusion of oxaliplatin in 250-500 ml 5% dextrose, over 120 minutes, at the same time as 200 mg/ml$^2$ intravenous infusion of leucovorin, followed by 400 mg/ml$^2$ of 5-fluorouracil intravenous bolus given over 4-6 minutes.

Cardiovascular Disease

Cachexia, chronic kidney disease, anemia, iron deficiency and hypertension can be associated with congestive or chronic heart failure (CHF). Accordingly, the antibodies described herein can be used to increase cardiac function in a subject in need thereof. In embodiments, method comprising administering an effective amount of an anti-GDF15 antibody to increase cardiac function in a subject is disclosed. In some embodiments, the subject suffers from cardiac dysfunction or CHF, and may optionally exhibit one or more of cachexia, chronic kidney disease, anemia, iron deficiency or hypertension.

In other embodiments, provided herein is a method of treating a cardiovascular disease using the anti-GDF15 antibodies disclosed. In some embodiments, the cardiovascular disease includes but is not limited to, congestive or chronic heart failure (CHF), myocardial hypertrophy or hypotrophy, acute coronary syndrome, angina, or other cardiac disorder or condition. In some embodiments, the subject treated has suffered a cardiac event such as a myocardial infarction, or has had, or is diagnosed as needing, a cardiac intervention, such as percutaneous coronary intervention, coronary artery bypass grafting, coronary angioplasty or stent placement.

In certain embodiments, the invention comprises a method of treating a subject exhibiting one or more cardiac related symptoms, which can be symptoms of cardiovascular disease or dysfunction, congestive or chronic heart failure, cardiac myopathies, cardiac hypertrophy, ischemic/reperfusion injury, dyspnea, idiopathic pulmonary arterial hypertension, ST-segment elevation myocardial infarction (STEMI), or other cardiac disorder or condition. Such cardiac-related symptoms are disclosed in WO 2015/196142, incorporated herein by reference. In some embodiments, the subject can be monitored in response to treatment with a GDF antibody as described herein, and to modify the dosing regimen if deemed clinically appropriate.

In certain embodiments, the subject having a cardiovascular disease or cardiac disorder, such as congestive or chronic heart failure (CHF), has previously been treated with a known cardiac treatment, but persists in exhibiting one or more symptoms. Thus, provided herein are methods and compositions for avoiding or reducing the occurrence and/or severity of at least one of the above cardiac-related symptoms, and may also avoid or reduce the need for one of the cardiac interventions described above.

Kidney Disease

The methods and compositions disclosed herein can also be useful for detecting, preventing, and treating conditions and disorders that involve disease, dysfunction, hypertrophy or hypotrophy of kidneys or renal tissue. Such conditions include, but are not limited to, chronic kidney or end stage renal failure, uremic syndrome, anemia, and/or reduced erythropoietin production from the kidneys, diabetes, insulin resistance and reduced kidney function or kidney size.

In some embodiments, the subject exhibits one or more additional symptoms of chronic kidney disease (CKD). In embodiments, the subject has CKD with anorexia and/or elevated plasma levels of GDF15. Said CKD symptoms can include one or more of the following indicators of chronic kidney disease, renal failure or kidney dysfunction: increased serum creatinine levels, decreased serum bilirubin levels, increased urine albumin concentration, increased urinary creatinine levels, increased urinary albumin-to-creatinine ratio (albumin-to-creatinine ratio of 25 mg/g or higher in women and 17 mg/g or higher in men, with a value of 30 mg/g indicative of serious CKD), increased urinary protein-to-creatinine ratio (protein-to-creatinine ratio of 200 mg/g is considered to be too high and indicative of CKD), hypertension (defined as systolic blood pressure of 140 mm Hg or above; diastolic blood pressure of 90 mm Hg or above; or undergoing current antihypertensive drug treatment), diabetes mellitus (defined as fasting glucose level of 126 mg/dL or higher; or the use of insulin or oral hypoglycemic medications); appearance of cystatin C in the urine or plasma, urinary C-reactive protein (uCRP), urinary retinol-binding protein (uRBP), hepcidin, increased serum levels of creatinine, hemojuvelin; uric acid and/or urea; beta trace protein; kidney injury molecule-1 (KIM-1); urinary N-acetyl-beta-(D)-glucosaminidase (NAG); urinary interleukin-18 (uIL-18); liver fatty acid binding protein-1 (L-FABP-1); blood urea nitrogen (BUN); micro-RNA 21 (miRNA-21); and electrolytes.

Additional symptoms, biochemical and physiological parameters that can be used to diagnose and/or monitor subjects for kidney disease are disclosed in WO 2015/196145, incorporated herein by reference.

In embodiments, the antibodies described herein can be used to reduce, e.g., deplete, GDF15 during a treatment of a subject with a kidney disease, e.g., dialysis.

Additional indications and dosages that can be used to treat the disorders with the antibodies disclosed herein are described in WO/2014/100689, WO 2016/049470, WO 2015/196142, and WO 2015/196145, the contents of all of which are hereby incorporated by reference.

Pharmaceutical Compositions

Provided herein is pharmaceutical compositions comprising the GDF15-binding antibodies (intact or binding fragments) formulated together with a pharmaceutically acceptable carrier. The compositions can additionally contain one or more other therapeutic agents that are suitable for treating or preventing, for example, wasting disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition described herein can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions described herein can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the GDF15-binding antibody is employed in the pharmaceutical compositions described herein. The GDF15-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies described herein employed in the pharmaceutical composition at levels lower than that required to achieve the desired therapeutic effect and gradually increase the dosage until the desired effect is achieved. In general, effective doses of the compositions described herein, for the treatment of a wasting disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of GDF15-binding antibody in the patient. In addition alternative dosing intervals can be determined by a physician and administered monthly or as necessary to be efficacious. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, human antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the disclosure but not to limit its scope. Other variants of the disclosure will be readily apparent to one of ordinary skill in the art and are encompassed by the appended claims.

Example 1: Preparation of Purified Recombinant His-GDF15 for Use as an Antigen

E. coli BL21 (DE3) transformed with a construct of His-GDF15 was grown in a Luria Broth medium. His-GDF15-containing inclusion bodies (IBs) were solubilized in a buffer containing 6 M guanidine and 20 mM beta-mercaptoethanol. The solubilized IBs were further purified on Ni-NTA-column followed by reverse phase chromatography. His-GDF15 containing pool was diluted 15-20 folds in a refolding buffer and gently stirred for days at 4° C. The refolded His-GDF15 was further purified by preparative reverse phase chromatography. Purified His-GDF15 pool was lyophilized and reconstituted in 30 mM sodium acetate buffer.

Example 2: Human Fab Phage Library Panning

For phage display, biotinylated human GDF15 was mixed with the MorphoSys's HuCAL (Human Combinatorial Antibody Library) phage library, allowed to bind for 1 hour. GDF15/phage complex was captured on Dynal M280 streptavidin beads for 10 minutes. After iterative rounds of panning, the pooled plasmid DNA was purified and digested with restriction enzymes EcoRI and XbaI. Plasmid DNA was separated by agarose gel electrophoresis and the 1.5 kB insert containing two gene segments (immunoglobulin heavy chain (VH/CH) and light chain (VL/CL)) was excised and purified. This 1.5 kB fragment (Fab insert) was subcloned into the Morphosys expression vector pMORPHX9_FH and transformed into electrocompetent TG-1 cells. Individual colonies were picked and master plates were prepared. Daughter plates inoculated from the master plates were re-grown in low glucose media and Fab expression was induced by culture in the presence of IPTG overnight. Cell pellets were frozen, lysed with lysozyme and cleared lysates were evaluated by ELISA on plates coated with PEO-biotinylated GDF15 coated on neutravidin-coated wells (negative control neutravidin alone). ELISA positives were retested following restreaking of master plate onto agar plates and picking of 3 individual colonies for retesting. Plasmid DNA from GDF15 Fab clones was also prepared for DNA sequencing. Fabs from unique clones were prepared in liter scale cultures induced with IPTG and then purified sequentially by IMAC and size exclusion chromatography. Protein concentrations were determined by absorbance at A280 nm coupled with SDS-PAGE.

Example 3: IgG Expression and Purification

VH and VL domains of anti-GDF15 Fabs were subcloned into an appropriate vector with human IgG constant region (CX28-98GC, pPL1551).

The integrity of the resulting clones was confirmed by DNA sequencing, and plasmid DNA of each construct was prepared for expression of the full IgGs by transient transfection of HEK-293T cells. Cell culture supernatants were harvested on day 7 after transfection and then purified on HiTrap Protein A.

Example 4: Antibody Engineering (Germling and Post-Translational-Modification (PTM) Sites Removal In silico germlining has been done by selecting the closest human germline sequence to the given VH and VL domain sequences. Positions in the framework regions of the given antibodies that appear to be different from the closest human germline sequence have been replaced with the human residue. Germlined sequences are then recombinantly produced and tested using standard molecular biology techniques.

The VH and VL domain sequences of antibodies were scanned by the presence of PTM motifs, e.g., NS, NG, DG or N×S/T. Identified PTMs can be removed by mutating the critical residue, e.g., N or G in the NG motif. The residue for the replacement is chosen following different criteria, e.g., the most frequent residues in that particular position in the VH/VL sequences of the same family or the closest residue in term of biophysical properties. The variants were then recombinantly produced and tested for activity and binding.

Example 5: Antibody Affinity

Biacore assay is based on surface plasmon resonance (SPR) and were used to determine the binding affinity of antibodies to GDF15.

Anti-human Fc capture antibody was immobilized at 0.5 µg/ml on CMS chip in all four flow cells to achieve 8000 to 12,000 resonance units (RU) on the surface. Anti-hGDF15 antibodies were captured at flow rate 10 µl/sec, at 0.25 to 0.5 µg/ml on the chip to get about 30 RU in flow cells 2, 3 and 4. GDF15 ligand was flowed at 45 µl/sec over captured antibodies and reference flow cell 1 for 600 and 1200 seconds contact time. Eight doses serially diluted 1 to 2, ranging from 20 to 0.156 nM, were tested. All cycles were repeated twice, regenerated between cycles with 3M $MgCl_2$ at flow 10 µl/sec, 20 seconds contact time. Data were normalized by subtracting reference flow cell results. Data were fit with 1:1 Kinetics model with RI (bulk refractive index) set constant at 0.

The results of Kd are shown in Table 2.

Example 6: Epitope Mapping

Antibody epitope was determined by a direct ELISA method with GDF15 mutants. Albumin fusion GDF15 mutants were coated in wells of a 96-well EIA plate. After blocking, serially diluted anti-hGDF15 human antibodies were added to the GDF15-coated wells, followed by incubation at an ambient temperature for a few hours. Antibody binding was detected using an anti-human IgG antibody conjugated with horseradish peroxidase (HRP) and HRP substrate.

FIG. 6 is a summary of the epitope mapping of anti-GDF15 antibodies based on loss-of-binding, or partially inhibited binding, to GDF15 fragments and mutations in using ELISA. The antibodies tested were ABGDF15-A, -B, -C, -D, -E, -F and -G, and Hu01G06 (a humanized antibody of anti-GDF15 antibody 01G06 (see WO2014/100689)) shown in the first column; The following wild-type and mutant GDF15 variants were tested: Wild-type human GDF15, rodent GDF15, cyno GDF15, N-terminal-truncated hGDF15 (having amino acids 211-308), GDF15 mutants having a mutation in the knuckle region (L294R, I285R, or S231R), wrist region, (Q247R, W228R, or M253R), finger tip region (D289R), and back-of-hand (S278R). "Knuckle," "wrist," "finger tip" and "back-of-hand" are 3-dimensional domains (not precise linear AA peptides), termed based on homologous crystal structures of all TGFβ family proteins (ref. Mueller and Nickel (2012) *Promiscuity and specificity in BMP receptor activation. FEBS Letters* 586: 1846-1859. ABGDF15-A, -B, -C, -D, -E, -F and -G all bind to the knuckle domain, as Knuckle domain associated mutations such as L294R, I285R and S231R, resulted in loss-of-binding or partially inhibited binding. In contrast, the L294R mutation did not affect binding by Hu01G06, a previously described humanized anti-GDF15 antibody.

Example 7: Effect of Anti-GDF15 Antibodies on Body Weight

The effect of anti-GDF15 antibodies on body weight was studied in a mouse anorexia model.

Thirteen-week old DIO mice were purchased from Taconic and maintained on high-fat diet throughout the study. Mice were single housed with normal light cycle (06:00-18:00), under ACUC protocol. At the beginning of the study, animals were weighed and grouped based on body weight so that the average weight was matched between negative control and treatment groups. Food weight was also recorded. On day 0, mice were injected via tail vain with 0.3 µg of an empty vector as negative control, or human full-length GDF15 expression vector by DNA hydrodynamic injection (HDI) (ref: Bonamassa et al. (2011) Hydrodynamic gene delivery and its applications in pharmaceutical research. Pharm Res:694-701). HDI led to hydrodynamic transfection of hepatocytes of the gene of interest in the expression vector. Plasma hGDF15 levels were determined on day 6. On day 7 weight and food weight were recorded. Mice were re-grouped based on comparable average hGDF15 levels and BW, and administered with therapeutic antibodies or an irrelevant antibody as negative control, respectively. Body weight and food weight were recorded several times a week and plasma were collected at the termination of the study.

Figure 1B:
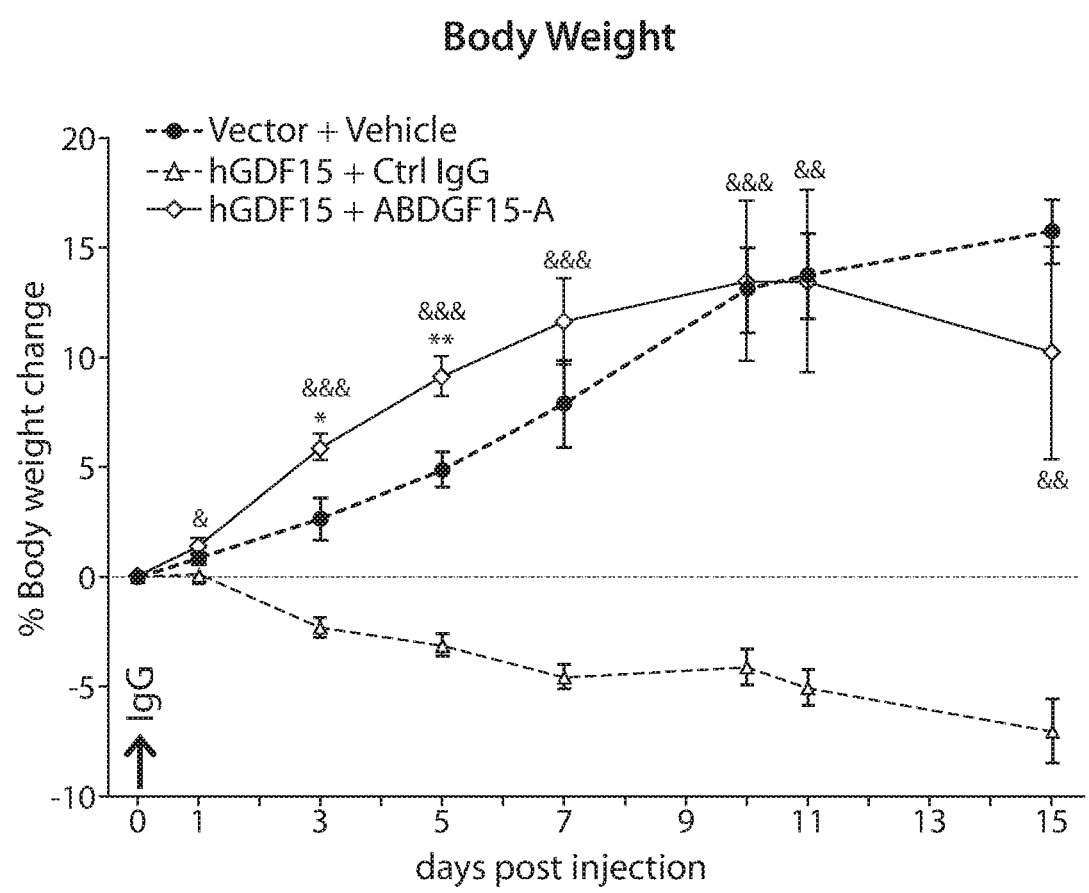

A time course of the effects of ABGDF15-A in blocking GDF15-mediated suppression of food intake and weight loss in diet-induced obesity (DIO) mice is shown in FIGS. 1A-1B. Human GDF15 was expressed in liver by hydrodynamic injection (HDI) of a human full-length GDF15 expression vector, leading to ~10% weight loss by day 7, prior to anti-GDF15 antibody administration (day 0 in the figure). One group of mice were injected with empty vector as negative control (Vector). Body weight and plasma human GDF15 levels were determined for individual mice and the animals were divided into two groups based on comparable average body weight and GDF15 levels. Antibodies (ABGDF15-A or an irrelevant control Ab) were administered intravenously at 10 mg/kg, and food intake and body weight were monitored.

FIG. 1A is a bar graph depicting the daily food intake (grams) after days post injection (1, 3, 5, 7, 10, 11 and 15 days). Measurements for three groups are provided for each time post antibody injection, from left to right: Vector+Vehicle; hGDF15+Control IgG; and hGDF15+ABGDF15-A.

FIG. 1B is a linear graph depicting the percent changes in body weight after days post injection (1, 3, 5, 7, 10, 11 and 15 days). Measurements for three groups are provided for each time post injection tested: Vector+Vehicle; hGDF15+Control IgG; and hGDF15+ABGDF15-A.

Statistical analysis was conducted using Student's t-Test for both studies, wherein *, **: p<0.05 and 0.01, ABGDF15-A vs. Vehicle; &, &&, &&&: p<0.05, 0.01 and 0.001, ABGDF15-A vs. Ctrl IgG.

Figure 2A:
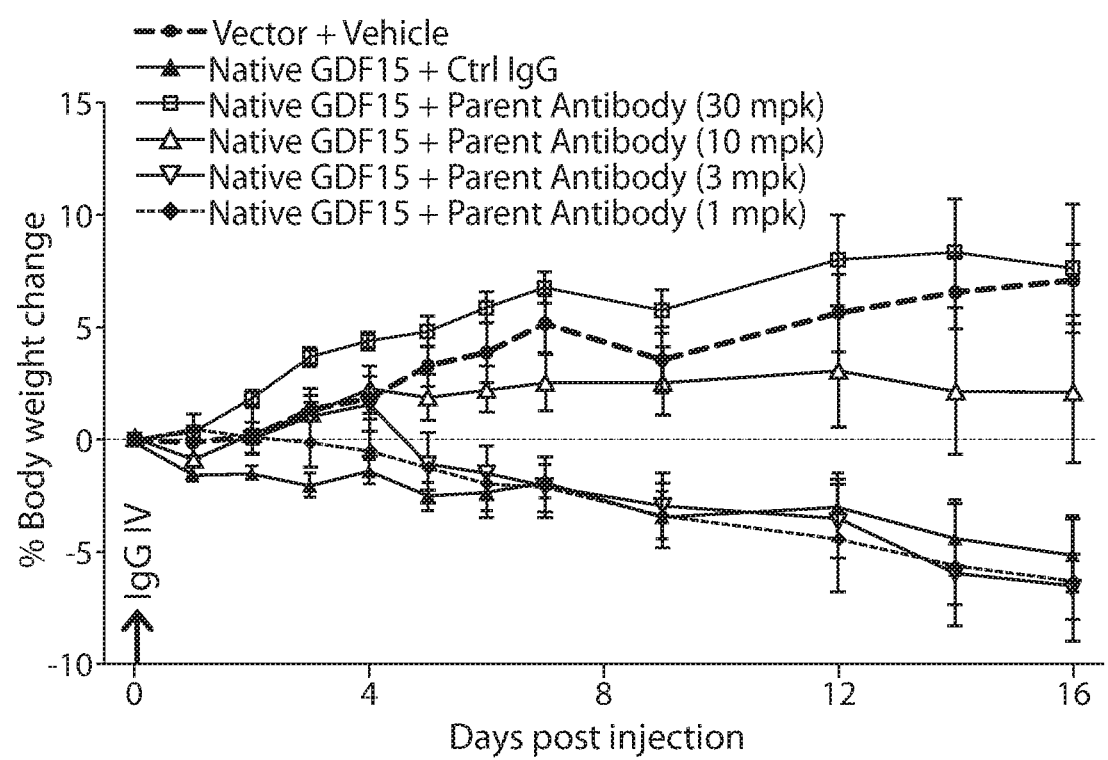
FIGS. 2A-2B depict a time course and dose-responsiveness of the effects of a parent antibody to ABGDF15-B and -C in blocking GDF15-mediated anorexia in an HD1 model. Human GDF15 was expressed in liver by HDI injection, leading to ~10% weight loss by day 7, prior to anti-GDF15 antibody administration (day 0 in the figure). The parent antibody, or a negative control antibody, were injected at the indicated concentrations; food intake and body weight were monitored.
Figure 2B:
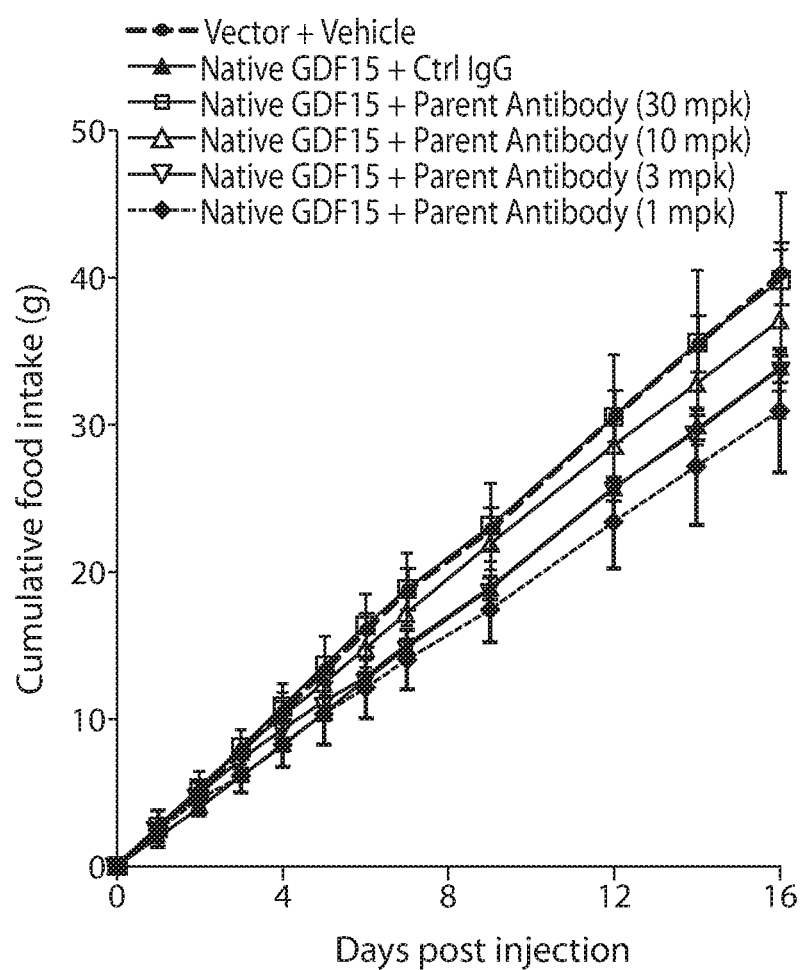

A time course and dose-responsiveness of the effects of ABGDF15-B in blocking GDF15-mediated anorexia in an HD1 model is depicted in FIGS. 2A-2B. Human GDF15 was expressed in liver by HDI injection, leading to ~10% weight loss by day 7, prior to anti-GDF15 antibody administration (day 0 in the figure). A parent antibody to ABGDF15-B and -C, or a negative control Ab. were injected at the indicated concentrations; food intake and body weight were monitored. FIGS. 2A-2B are linear graphs depicting the cumulative food intake (grams) and percent changes in body weight, respectively, after days post antibody injection (1, 4, 8, 12 and 16 days). The following treatment groups were illustrated in FIGS. 2A-2B: Vector+Vehicle; hGDF15+Control IgG; hGDF15+parent antibody (30 mg/kg); hGDF15+parent antibody (10 mg/kg); hGDF15+parent antibody (3 mg/kg); and hGDF15+parent antibody (1 mg/kg). Parent antibody dose-dependently reversed GDF15-mediated anorexic effects.

The parent antibody tested shares identical heavy chain and light chain CDRs with ABGDF15-B and -C, with some differences in the framework region. The amino acid sequence of the light chain of the parent antibody is as follows:

(SEQ ID NO: 187)
DIELTQPPSVSVSPGQTASITCSGDNIGSHIVSWYQQKPGQAPVLVIYD

KSNRPSGIPERFSGSNSGNTATLTISGTQAEDEADYYCQTWDSIGSVVF

GGGTKLTVLGQPKAAPSVTLFPPSSEELQANKATLVCLISDFYPGAVTV

AWKADSSPVKAGVETTTPSKQSNNKYAASSYLSLTPEQWKSHRSYSCQV

THEGSTVEKTVAPTECS

Figure 3A:
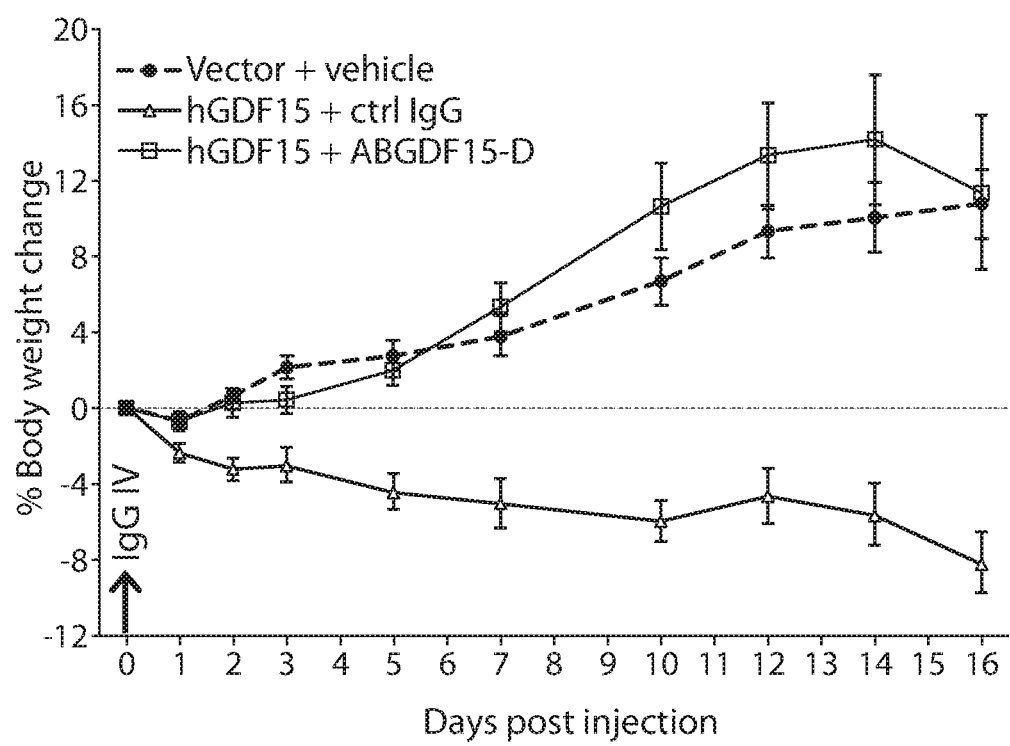
FIGS. 3A-3B depict a time course of the effects of ABGDF15-D in blocking human GDF15-mediated anorexia in an HD1 model. Human GDF15 was expressed in liver by HDI injection, leading to ~10% weight loss by day 7, prior to anti-GDF15 antibody administration (day 0 in the figure). The ABGDF15-D or a negative control Ab were injected at 20 mg/kg; food intake and body weight were monitored.
Figure 3B:
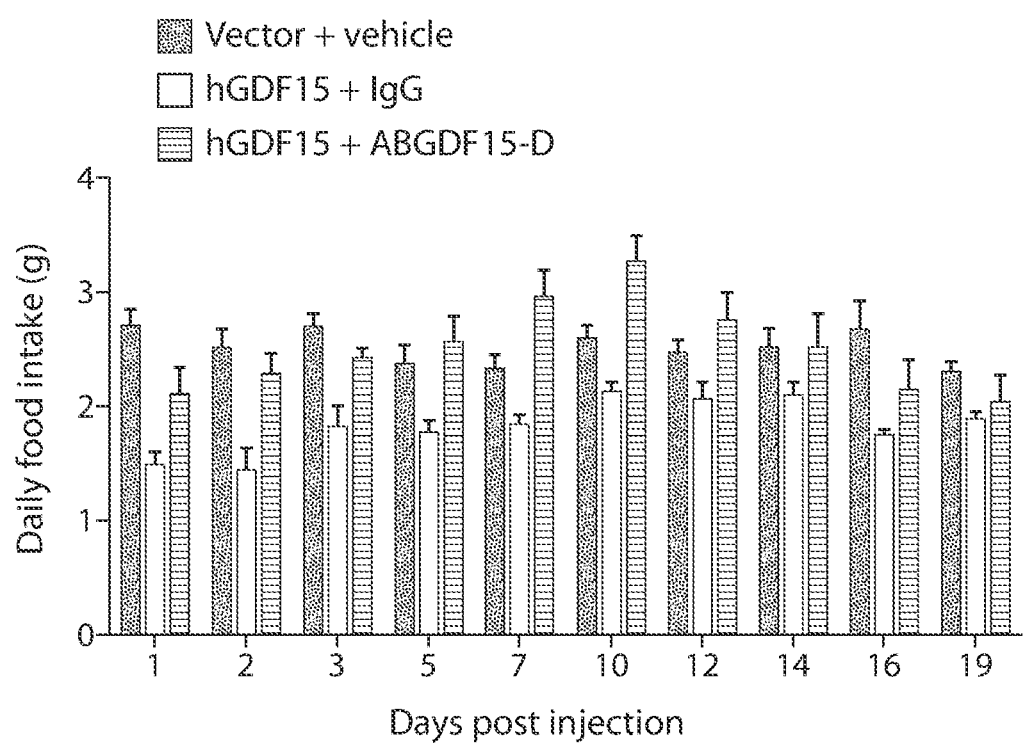

A time course of the effects of ABGDF15-D in blocking native GDF15-mediated anorexia in an HD1 model in FIGS. 3A-3B. Human GDF15 was expressed in liver by HDI injection, leading to ~10% weight loss by day 7, prior to anti-GDF15 antibody administration (day 0 in the figure). The ABGDF15-D or a negative control Ab were injected at 20 mg/kg; food intake and body weight were monitored. FIGS. 3A-3B are a linear graph and bar graph depicting daily food intake (grams) and the percent changes in body weight, respectively, after days post injection. The following groups were illustrated in FIGS. 3A-3B: Vector+Vehicle; hGDF15+Control IgG; hGDF15+ABGDF15-D for each time point. ABGDF15-D reversed GDF15-mediated anorexic effects.

Figure 4:
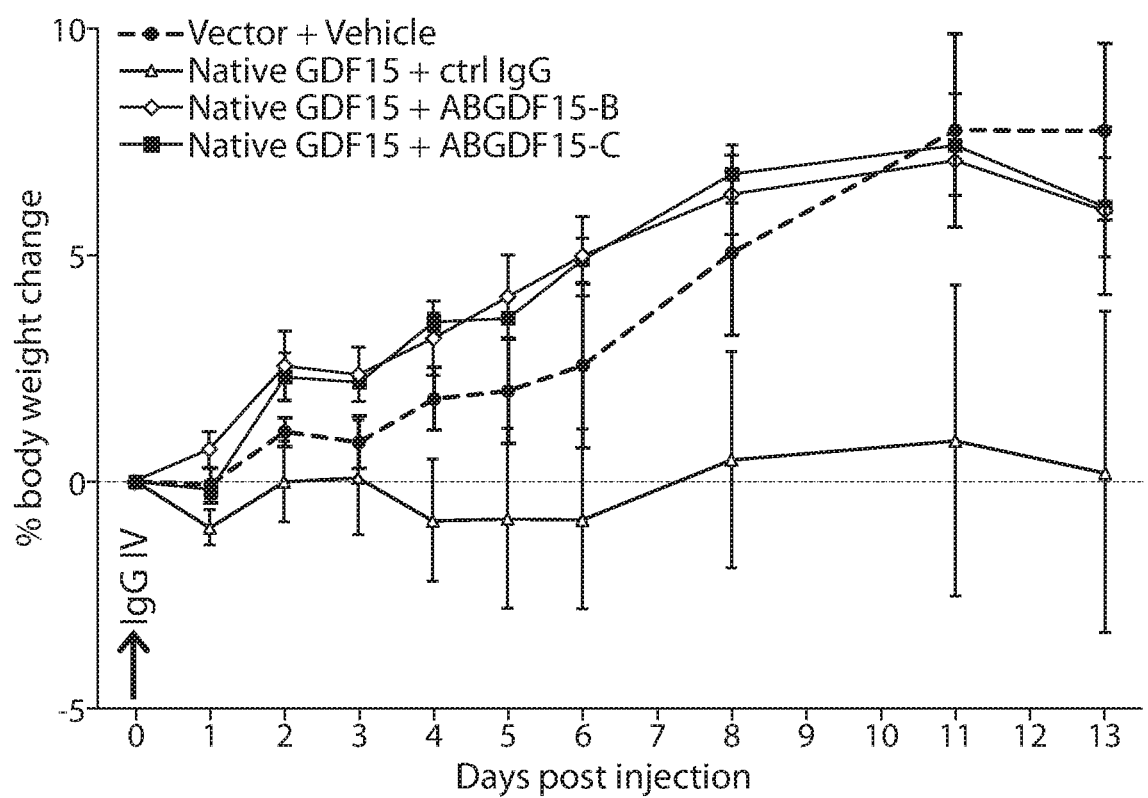
FIG. 4 is a linear graph depicting a time course of the effects of ABGDF15-B and -C in blocking human GDF15-mediated weight loss in DIO mice. GDF15 was overexpressed by HDI injection in DIO mice. The anti-GDF15 antibodies were administered intravenously at 20 mg/kg, and body weight was monitored. The following groups were compared: Vector+Vehicle; hGDF15+Control IgG; hGDF15+ABGDF15-B, and hGDF15+ABGDF15-C for each time point. Both ABGDF15-B and -C reversed GDF15-mediated weight loss.

FIG. 4 is a linear graph depicting a time course of the effects of ABGDF15-B and -C in blocking human GDF15-mediated weight loss in DIO mice. GDF15 was overexpressed by HDI injection in DIO mice. The anti-GDF15 antibodies were administered intravenously at 20 mg/kg, and body weight was monitored. The following groups were compared: Vector+Vehicle; hGDF15+Control IgG; hGDF15+ABGDF15-B, and hGDF15+ABGDF15-C for each time point. Both ABGDF15-B and -C reversed GDF15-mediated weight loss.

Figure 5:
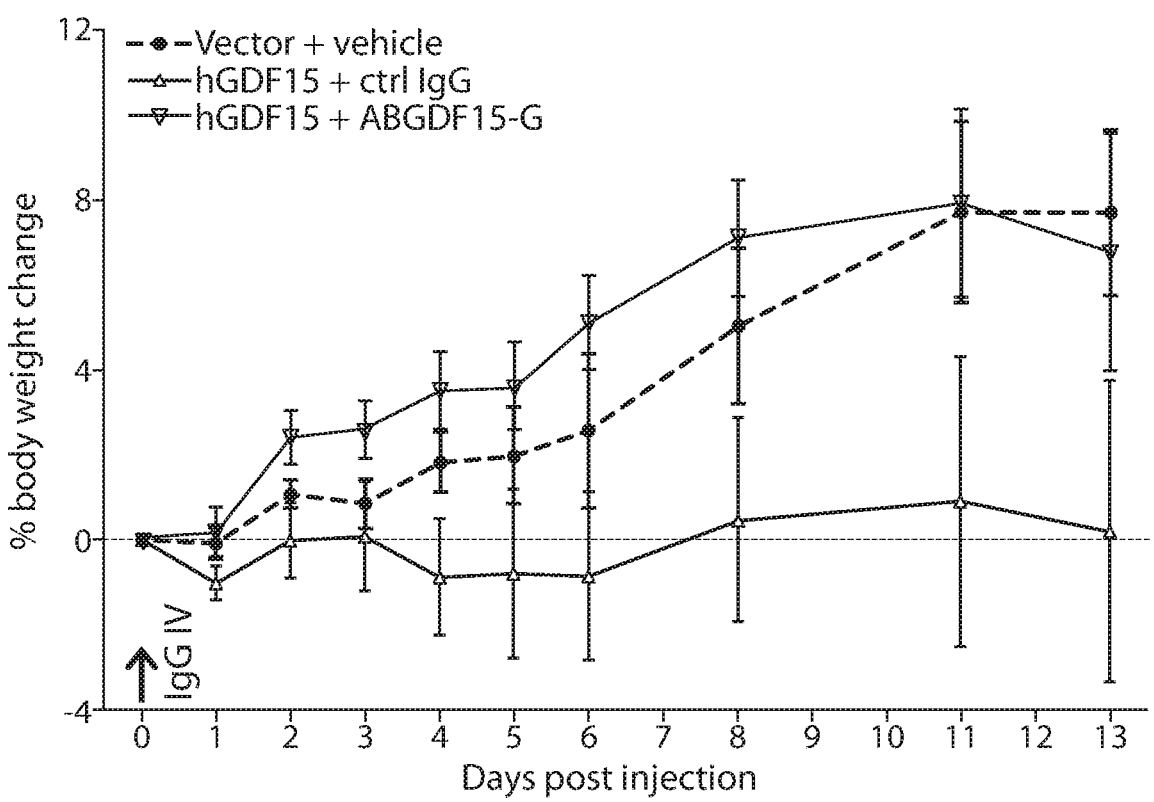
FIG. 5 is a linear graph depicting a time course of the effects of ABGDF15-G in blocking human GDF15-mediated weight loss in DIO mice. GDF15 was overexpressed continuously by HDI injection in DIO mice. ABGDF15-G was administered intravenously at 20 mg/kg, and body weight was monitored. The following groups were illustrated: Vector+Vehicle; hGDF15+Control IgG; and hGDF15+ABGDF15-G, for each time point. ABGDF15-G reversed GDF15-mediated weight loss.

FIG. 5 is a linear graph depicting a time course of the effects of ABGDF15-G in blocking human GDF15-mediated weight loss in DIO mice. GDF15 was overexpressed continuously by HDI injection in DIO mice. ABGDF15-G was administered intravenously at 20 mg/kg, and body weight was monitored. The following groups were illustrated: Vector+Vehicle; hGDF15+Control IgG; and hGDF15+ABGDF15-G, for each time point. ABGDF15-G reversed GDF15-mediated weight loss.

The table below provides a summary of head-to-head comparison of the percent changes in body weight, and in weight gain relative to the control IgG in mice after antibody treatment, in a similar HDI experiments described above.

This in vivo model was used to compare the activity of the anti-GDF15 antibodies.

|  | Weight change (%) | Weight gain vs GDF15 + ctrl IgG (%) | SD |
| --- | --- | --- | --- |
| hGDF15 + ctrl IgG | −5.0 |  |  |
| hGDF15 + ABGDF15-A | 9.0 | 14.0 | 4.8 |
| hGDF15 + ABGDF15-D | 4.2 | 9.2 | 2.8 |
| hGDF15 + ABGDF15-C | 2.4 | 7.4 | 2.9 |
| hGDF15 + ABGDF15-B | 1.3 | 6.3 | 4.3 |
| hGDF15 + ABGDF15-F | −0.5 | 4.5 | 2.9 |
| hGDF15 + ABGDF15-G | −1.3 | 3.7 | 5.1 |
| hGDF15 + ABGDF15-E | −1.4 | 3.6 | 4.4 | n = 6/group
on day 7 post Ab administration

In summary, anti-GDF15 antibodies tested herein, e.g., ABGDF15-A, -B, -C, -D, -E, -F, and -G, were able to reverse GDF15-mediated suppression of food intake and body weight loss in these mouse models.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention. It will be appreciated, however, that no matter how detailed the foregoing may appear in text, the invention may be practiced in many ways and the invention should be construed in accordance with the appended claims and any equivalents thereof.

What is claimed is:

1. An antibody, or antigen binding fragment thereof, that binds to human growth differentiation factor-15 (GDF15), comprising:
(i)
a heavy chain variable region (VH) CDR1 (HCDR1) comprising the amino acid sequence of SEQ ID NO: 6,
a VH CDR2 (HCDR2) comprising the amino acid sequence of SEQ ID NO: 7,
a VH CDR3 (HCDR3) comprising the amino acid sequence of SEQ ID NO: 8,
a light chain variable region (VL) CDR1 (LCDR1) comprising the amino acid sequence of SEQ ID NO: 19,
a VL CDR2 (LCDR2) comprising the amino acid sequence of SEQ ID NO: 20, and
a VL CDR3 (LCDR3) comprising the amino acid sequence of SEQ ID NO: 21; or
(ii)
a VH CDR1 (HCDR1) comprising the amino acid sequence of SEQ ID NO: 9,
a VH CDR2 (HCDR2) comprising the amino acid sequence of SEQ ID NO: 10,
a VH CDR3 (HCDR3) comprising the amino acid sequence of SEQ ID NO: 11,
a VL CDR1 (LCDR1) comprising the amino acid sequence of SEQ ID NO: 22,
a VL CDR2 (LCDR2) comprising the amino acid sequence of SEQ ID NO: 23, and
a VL CDR3 (LCDR3) comprising the amino acid sequence of SEQ ID NO: 24; or
(iii)
a VH CDR1 (HCDR1) comprising the amino acid sequence of SEQ ID NO: 3,
a VH CDR2 (HCDR2) comprising the amino acid sequence of SEQ ID NO: 4,
a VH CDR3 (HCDR3) comprising the amino acid sequence of SEQ ID NO: 5,
a VL CDR1 (LCDR1) comprising the amino acid sequence of SEQ ID NO: 16,
a VL CDR2 (LCDR2) comprising the amino acid sequence of SEQ ID NO: 17, and
a VL CDR3 (LCDR3) comprising the amino acid sequence of SEQ ID NO: 18.

2. The antibody or antigen binding fragment thereof according to claim 1, comprising:
(i)
a heavy chain variable region (VH) CDR1 (HCDR1) consisting of the amino acid sequence of SEQ ID NO: 6,
a VH CDR2 (HCDR2) consisting of the amino acid sequence of SEQ ID NO: 7,
a VH CDR3 (HCDR3) consisting of the amino acid sequence of SEQ ID NO: 8,
a light chain variable region (VL) CDR1 (LCDR1) consisting of the amino acid sequence of SEQ ID NO: 19,
a VL CDR2 (LCDR2) consisting of the amino acid sequence of SEQ ID NO: 20, and
a VL CDR3 (LCDR3) consisting of the amino acid sequence of SEQ ID NO: 21; or
(ii)
a VH CDR1 (HCDR1) consisting of the amino acid sequence of SEQ ID NO: 9,
a VH CDR2 (HCDR2) consisting of the amino acid sequence of SEQ ID NO: 10,
a VH CDR3 (HCDR3) consisting of the amino acid sequence of SEQ ID NO: 11,
a VL CDR1 (LCDR1) consisting of the amino acid sequence of SEQ ID NO: 22,
a VL CDR2 (LCDR2) consisting of the amino acid sequence of SEQ ID NO: 23, and
a VL CDR3 (LCDR3) consisting of the amino acid sequence of SEQ ID NO: 24; or
(iii)
a VH CDR1 (HCDR1) consisting of the amino acid sequence of SEQ ID NO: 3,
a VH CDR2 (HCDR2) consisting of the amino acid sequence of SEQ ID NO: 4,
a VH CDR3 (HCDR3) consisting of the amino acid sequence of SEQ ID NO: 5,
a VL CDR1 (LCDR1) consisting of the amino acid sequence of SEQ ID NO: 16,
a VL CDR2 (LCDR2) consisting of the amino acid sequence of SEQ ID NO: 17, and
a VL CDR3 (LCDR3) consisting of the amino acid sequence of SEQ ID NO: 18.

3. The antibody or antigen-binding fragment thereof according to claim 1, comprising a VH with the amino acid sequence of SEQ ID NO: 12; and/or a VL with the amino acid sequence of SEQ ID NO: 25; or for each sequence the amino acid sequence with 97-99% identity thereof.

4. The antibody or antigen-binding fragment thereof according to claim 1, comprising:
a VH with the amino acid sequence of SEQ ID NO: 12; and
a VL with the amino acid sequence of SEQ ID NO: 25.

5. The antibody or antigen-binding fragment thereof according to claim 1, having two, three, four, five, six, seven, eight, or all of the following properties:
(i) binds specifically to one or more amino acids in the knuckle domain of GDF15;
(ii) has a $K_D$ value of less than or equal to 150 pM, as determined by Biacore;
(iii) is cross-reactive with two, three or all of human GDF15, cynomolgus GDF15, mouse GDF15, or rat GDF15;
(iv) has an isoelectric point (pI) of between 8 and 10;
(v) reduces the level of GDF15 in a subject;
(vi) reduces GDF15-mediated suppression of food intake;
(vii) reduces GDF15-mediated suppression of weight loss; or
(viii) reduces GDF15-mediated anorexia.

6. The antibody or antigen-binding fragment thereof according to claim 1, which has a $K_D$ for human GDF15 of less than or equal to 115 pM, as measured by Biacore, or less than or equal to 120 pM, as measured by solution equilibrium titration assay (SET).

7. The antibody or antigen-binding fragment thereof according to claim 1, which binds to one, two or all of amino acids 231, 285, or 294 of SEQ ID NO:1.

8. The antibody or antigen-binding fragment thereof according to claim 1, which binds to amino acids 285 and 294 of SEQ ID NO:1, or amino acids 231 and 285 of SEQ ID NO:1.

9. A pharmaceutical composition comprising an antibody or fragment thereof according to claim 1 and a pharmaceutically acceptable carrier.

10. An isolated nucleic acid molecule comprising a first nucleotide sequence that encodes a VH, and/or a second nucleotide sequence that encodes a VL of an antibody or antigen-binding fragment thereof according to claim 1.

11. A vector comprising the isolated nucleic acid molecule of claim 10.

12. A host cell comprising the isolated nucleic acid molecule of claim 10.

13. A method of producing an antibody, comprising culturing the host cell of claim 12 under conditions suitable for gene expression.

14. A method of treating a GDF15-associated disorder comprising administering to a subject in need thereof an antibody or antigen-binding fragment thereof according to claim 1, wherein the GDF15-associated disorder is associated with decreased appetite, progressive and/or involuntary weight loss, or cachexia.

15. The method of claim 14, wherein the disorder is anorexia, sarcopenia, cachexia, cancer, heart failure, COPD, renal failure, and/or a wasting disorder.

16. The method of claim 15, wherein the cachexia is cachexia associated with aging or cachexia associated with cancer.

17. A method of increasing one or more of: appetite, food intake, or body weight comprising administering to a subject in need thereof an antibody or antigen-binding fragment thereof according to claim 1.

18. A method of inhibiting or reducing one or more of: loss of body weight, muscle mass, appetite, or food intake comprising administering to a subject in need thereof an antibody or antigen-binding fragment thereof according to claim 1.

19. The method of claim 17, wherein the subject has a wasting disorder, a cancer, chronic heart failure, a chronic kidney disease, COPD, AIDS, multiple sclerosis, rheumatoid arthritis, sepsis, and/or tuberculosis.

20. The method of claim 18, wherein the subject has a wasting disorder, a cancer, chronic heart failure, a chronic kidney disease, COPD, AIDS, multiple sclerosis, rheumatoid arthritis, sepsis, and/or tuberculosis.

* * * * *